(12) United States Patent
Kato et al.

(10) Patent No.: US 9,382,206 B2
(45) Date of Patent: Jul. 5, 2016

(54) NITROGEN-CONTAINING AROMATIC HETEROCYCLIC DERIVATIVE AND ORGANIC ELECTROLUMINESCENCE DEVICE USING THE SAME

(75) Inventors: Tomoki Kato, Sodegaura (JP); Kazuki Nishimura, Sodegaura (JP); Chishio Hosokawa, Sodegaura (JP); Masaki Numata, Sodegaura (JP); Hideaki Nagashima, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 632 days.

(21) Appl. No.: 13/496,995

(22) PCT Filed: Aug. 24, 2011

(86) PCT No.: PCT/JP2011/004700
§ 371 (c)(1),
(2), (4) Date: Mar. 19, 2012

(87) PCT Pub. No.: WO2012/029253
PCT Pub. Date: Mar. 8, 2012

(65) Prior Publication Data
US 2012/0181524 A1 Jul. 19, 2012

(30) Foreign Application Priority Data
Aug. 31, 2010 (JP) ................. 2010-194904

(51) Int. Cl.
| | |
|---|---|
| *H01L 51/54* | (2006.01) |
| *C09K 11/06* | (2006.01) |
| *C07D 209/86* | (2006.01) |
| *C07D 219/02* | (2006.01) |
| *C07D 401/14* | (2006.01) |
| *C07D 403/14* | (2006.01) |
| *C07D 405/14* | (2006.01) |
| *H05B 33/14* | (2006.01) |
| *C09B 15/00* | (2006.01) |
| *C09B 17/00* | (2006.01) |
| *C09B 19/00* | (2006.01) |
| *C09B 21/00* | (2006.01) |
| *C09B 57/00* | (2006.01) |
| *H01L 51/00* | (2006.01) |
| *H01L 51/50* | (2006.01) |

(52) U.S. Cl.
CPC .......... *C07D 209/86* (2013.01); *C07D 219/02* (2013.01); *C07D 401/14* (2013.01); *C07D 403/14* (2013.01); *C07D 405/14* (2013.01); *C09B 15/00* (2013.01); *C09B 17/00* (2013.01); *C09B 19/00* (2013.01); *C09B 21/00* (2013.01); *C09B 57/00* (2013.01); *C09K 11/06* (2013.01); *H01L 51/0071* (2013.01); *H01L 51/0072* (2013.01); *H05B 33/14* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1088* (2013.01); *C09K 2211/1092* (2013.01); *H01L 51/0059* (2013.01); *H01L 51/0085* (2013.01); *H01L 51/5012* (2013.01)

(58) Field of Classification Search
None
See application file for complete search history.

(56) References Cited

U.S. PATENT DOCUMENTS

| | | | | |
|---|---|---|---|---|
| 6,720,573 | B2 * | 4/2004 | Son et al. ................... | 257/40 |
| 2002/0045061 | A1 * | 4/2002 | Hosokawa ................... | 428/690 |
| 2005/0127823 | A1 | 6/2005 | Iwakuma et al. | |
| 2005/0221124 | A1 * | 10/2005 | Hwang et al. ................ | 428/690 |
| 2006/0180806 | A1 * | 8/2006 | Arakane et al. ............. | 257/40 |

(Continued)

FOREIGN PATENT DOCUMENTS

| | | |
|---|---|---|
| EP | 1 961 741 A1 | 8/2008 |
| EP | 2 492 985 A1 | 8/2012 |

(Continued)

OTHER PUBLICATIONS

Vaitkeviciene et al. Synthetic Metals 2008, 158, 383-390. Date of online publication: Apr. 15, 2008.*

(Continued)

*Primary Examiner* — Andrew K Bohaty
(74) *Attorney, Agent, or Firm* — Oblon, McClelland, Maier & Neustadt, L.L.P.

(57) ABSTRACT

A nitrogen-containing aromatic heterocyclic derivative represented by the following formula, wherein $X_1$ to $X_3$ are a single bond, CRaRb, NRc, an oxygen atom or a sulfur atom, and when all of $X_1$ to $X_3$ is a single bond, at least one of Ara, Arb and Arc is an aryl group having 6 to 20 ring carbon atoms substituted with a heteroaryl group, an aryloxy group or a heteroaryloxy group, or a substituted or unsubstituted heteroaryl group having 5 to 20 ring atoms.

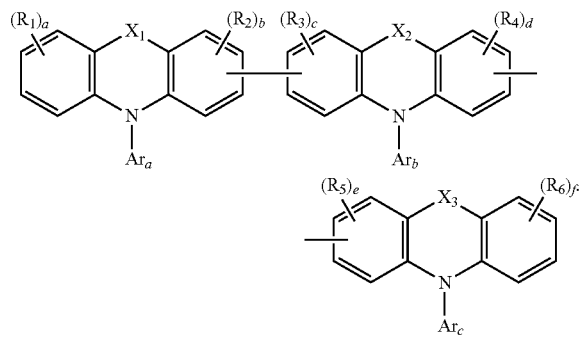

17 Claims, No Drawings

(56) References Cited

U.S. PATENT DOCUMENTS

| | | |
|---|---|---|
| 2008/0254318 A1 | 10/2008 | Nakashima et al. |
| 2009/0017331 A1* | 1/2009 | Iwakuma et al. ............ 428/690 |
| 2009/0045726 A1 | 2/2009 | Miki et al. |
| 2009/0167165 A1 | 7/2009 | Otsu et al. |
| 2009/0179554 A1* | 7/2009 | Kuma et al. ................ 313/504 |
| 2009/0206736 A1 | 8/2009 | Kuma et al. |
| 2009/0243473 A1 | 10/2009 | Iwakuma et al. |
| 2009/0302745 A1 | 12/2009 | Otsu et al. |
| 2012/0085997 A1 | 4/2012 | Sugita et al. |
| 2012/0273767 A1* | 11/2012 | Yokoyama et al. ............ 257/40 |

FOREIGN PATENT DOCUMENTS

| | | | |
|---|---|---|---|
| EP | 2 492 986 A1 | | 8/2012 |
| JP | 8-3547 A | | 1/1996 |
| JP | 2006-298898 A | | 11/2006 |
| JP | 2007-288035 A | | 11/2007 |
| JP | 2007-311460 A | | 11/2007 |
| JP | 2008-135498 A | | 6/2008 |
| JP | 2008135498 A | * | 6/2008 |
| JP | 2009292806 A | * | 12/2009 |
| KR | 10-2009-0028943 A | | 3/2009 |
| KR | 2009028943 A | * | 3/2009 |
| WO | WO 03/078541 A1 | | 9/2003 |
| WO | WO 2007/069607 A1 | | 6/2007 |
| WO | WO 2007/132678 A1 | | 11/2007 |
| WO | WO 2007/132704 A1 | | 11/2007 |
| WO | WO 2008/015949 A1 | | 2/2008 |
| WO | WO 2010/002848 A1 | * | 1/2010 |
| WO | WO 2010/150593 A1 | | 12/2010 |
| WO | WO 2011/048821 A1 | | 4/2011 |
| WO | WO 2011/048822 A1 | | 4/2011 |
| WO | WO 2011/071255 A1 | | 6/2011 |

OTHER PUBLICATIONS

Kwon et a. SID 09 Digest 2009, 23.4 pp. 317-320. Year of publication: 2009.*

Machine translation of JP2008-135498. Date of Publication: Jun. 12, 2008.*

Brunner et al. J. Am. Chem. Soc. 2004, 126, 6035-6042. Date of online publication: Apr. 23, 2004.*

Supporting Information for Brunner et al. J. Am. Chem. Soc. 2004, 126, 6035-6042. pp. 1-12. Date of online publication: Apr. 23, 2004.*

Machine translation of KR2009-028943. Date of publication: Mar. 20, 2009.*

Machine translation of JP2009-292806. Date of publication: Dec. 17, 2009.*

International Search Report issued Nov. 8, 2011 in PCT/JP2011/004700.

Guo-Liang Feng, et al., "Synthesis and Optical Properties of Starburst Carbazoles Based on 9-Phenylcarbazole Core", Synlett, No. 17, 2006, pp. 2841-2845.

Extended European Search Report issued Jan. 21, 2014 in Patent Application No. 11802255.7.

* cited by examiner

NITROGEN-CONTAINING AROMATIC HETEROCYCLIC DERIVATIVE AND ORGANIC ELECTROLUMINESCENCE DEVICE USING THE SAME

This application is a National Stage of PCT/JP11/004700 filed Aug. 24, 2011 and claims the benefit of JP 2010-194904 filed Aug. 31, 2010.

TECHNICAL FIELD

The invention relates to a nitrogen-containing aromatic heterocyclic derivative and an organic electroluminescence device using the same.

BACKGROUND ART

An organic electroluminescence device (organic EL device) is a promising solid-state emitting type inexpensive and large full-color display device, and has been extensively developed. In general, an organic EL device includes an emitting layer and a pair of opposing electrodes holding the emitting layer therebetween. When an electric field is applied between the electrodes, electrons are injected from a cathode and holes are injected from an anode. The electrons recombine with the holes in the emitting layer to produce an excited state, and energy is emitted as light when the excited state returns to the ground state.

In addition, a phosphorescent organic EL device has been proposed wherein an organic phosphorescent material is used for an emitting layer of the organic EL device. In the phosphorescent organic EL device, high luminous efficiency is achieved by utilizing a singlet state and a triplet state of the excited state of the organic phosphorescent material. When an electron and a hole are recombined in the organic EL device, since it is believed that singlet exciton and triplet exciton are generated at a rate of 1:3 due to the difference in spin multiplicity, three to four times greater luminous efficiency is considered to be achieved if a phosphorescent emitting material is used, in comparison with a device using a fluorescent material only.

Early organic EL devices are insufficient in driving voltage, luminous efficiency and durability, and various technical improvements have been made for the problems.

The improvements of luminous efficiency and lifetime of the organic EL device are important subjects which lead to a low power consumption of display and improvement of durability. Therefore, further improvement is required. In addition, a variety of studies have been carried out to improve luminous efficiency and life time of an organic EL device using a phosphorescent emitting material.

To solve the problems, Patent Document 1 discloses a biscarbazole derivative which can be used as a hole-transporting material. This biscarbazole skeleton has a function to improve heat resistance. Patent Document 2 discloses a biscarbazole derivative which can be used as a phosphorescent emitting host material.

Patent Documents 3 and 4 disclose compounds having carbazole, dibenzofuran, and dibenzothiophene skeletons for a phosphorescent emitting host material.
[Patent Document 1] JP-A-H8-3547
[Patent Document 2] JP-A-2008-135498
[Patent Document 3] JP-A-2007-288035
[Patent Document 4] JP-A-2007-311460

DISCLOSURE OF THE INVENTION

Although Patent Document 1 describes that a biscarbazole derivative is a hole-transporting material having high Tg and excellent heat resistance, there is no description suggesting a combination with a phosphorescent emitting layer.

In addition, in the invention of Patent Document 2, a biscarbazole derivative is used as a phosphorescent emitting host material, and there is concern that luminous efficiency will significantly be deteriorated.

Although Patent Document 3 and Patent Document 4 describe derivatives having carbazole, dibenzofuran, and dibenzothiophene skeletons as a phosphorescent emitting host material, they do not suggest a function as a hole-transporting material.

An object of the invention is to provide a novel compound which can be used for an organic EL device. Another object of the invention is to provide an organic EL device which has high luminous efficiency and a long life time, and which can be driven at a low voltage.

According to the invention, the following nitrogen-containing aromatic heterocyclic derivative and the like are provided.

1. A nitrogen-containing aromatic heterocyclic derivative represented by the following formula (1):

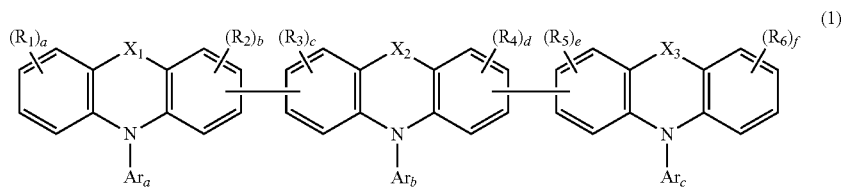

wherein $X_1$ to $X_3$ are independently a single bond, CRaRb, NRc, an oxygen atom or a sulfur atom, Ra, Rb and Rc are independently a linear or branched alkyl group having 1 to 15 carbon atoms, a cycloalkyl group having 3 to 15 carbon atoms, an aryl group having 6 to 20 carbon atoms that form a ring (hereinafter referred to as "ring carbon atoms") or a heteroaryl group having 5 to 20 atoms that form a ring (hereinafter referred to as "ring atoms").

$Ar_a$, $Ar_b$ and $Ar_c$ are independently a substituted or unsubstituted aryl group having 6 to 20 ring carbon atoms or a substituted or unsubstituted heteroaryl group having 5 to 20 ring atoms, when all of $X_1$ to $X_3$ is a single bond, at least one of $Ar_a$, $Ar_b$ and $Ar_c$ is an aryl group having 6 to 20 ring carbon atoms substituted with a heteroaryl group, an aryloxy group or a heteroaryloxy group, or a substituted or unsubstituted heteroaryl group having 5 to 20 ring atoms, $R_1$ to $R_6$ are independently a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group, two adjacent groups of $R_1$ to $R_6$ may be saturated or unsaturated divalent groups that are bonded each other to form a ring, a and f are independently an integer of 0 to 4, and b, c, d and e are independently an integer of 0 to 3.

2. The nitrogen-containing aromatic heterocyclic derivative according to 1, represented by the following formula (2):

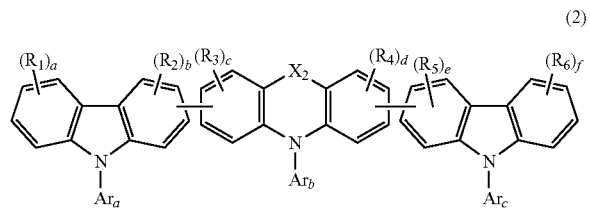

(2)

wherein $X_2$ is a single bond, CRaRb, NRc, an oxygen atom or a sulfur atom,

Ra, Rb and Rc are independently a linear or branched alkyl group having 1 to 15 carbon atoms, a cycloalkyl group having 3 to 15 carbon atoms, an aryl group having 6 to 20 ring carbon atoms or a heteroaryl group having 5 to 20 ring atoms, $Ar_a$, $Ar_b$ and $Ar_c$ are independently a substituted or unsubstituted aryl group having 6 to 20 ring carbon atoms or a substituted or unsubstituted heteroaryl group having 5 to 20 ring atoms, when $X_2$ is a single bond, at least one of $Ar_a$, $Ar_b$ and $Ar_c$ is an aryl group having 6 to 20 ring carbon atoms substituted with a heteroaryl group, an aryloxy group or a heteroaryloxy group, or a substituted or unsubstituted heteroaryl group having 5 to 20 ring atoms, $R_1$ to $R_6$ are independently a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group, two adjacent groups of $R_1$ to $R_6$ may be saturated or unsaturated divalent groups that are bonded each other to form a ring, a and f are independently an integer of 0 to 4, and b, c, d and e are independently an integer of 0 to 3.

3. The nitrogen-containing aromatic heterocyclic derivative according to 1, represented by the following formula (3):

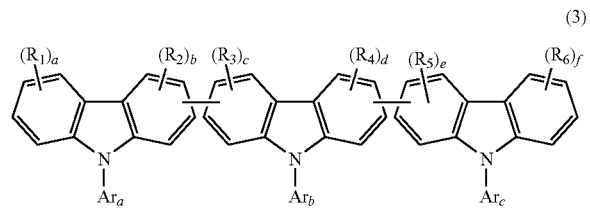

(3)

wherein $Ar_a$, $Ar_b$ and $Ar_c$ are independently a substituted or unsubstituted aryl group having 6 to 20 ring carbon atoms or a substituted or unsubstituted heteroaryl group having 5 to 20 ring atoms, at least one of $Ar_a$, $Ar_b$ and $Ar_c$ is an aryl group having 6 to 20 ring carbon atoms substituted with a heteroaryl group, an aryloxy group or a heteroaryloxy group, or a substituted or unsubstituted heteroaryl group having 5 to 20 ring atoms, $R_1$ to $R_6$ are independently a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group, two adjacent groups of $R_1$ to $R_6$ may be saturated or unsaturated divalent groups that are bonded each other to form a ring, a and f are independently an integer of 0 to 4, and b, c, d and e are independently an integer of 0 to 3.

4. The nitrogen-containing aromatic heterocyclic derivative according to 1, represented by the following formula (4):

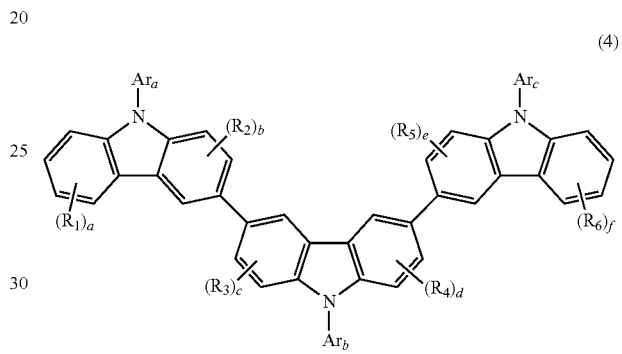

(4)

wherein $Ar_a$, $Ar_b$ and $Ar_c$ are independently a substituted or unsubstituted aryl group having 6 to 20 ring carbon atoms or a substituted or unsubstituted heteroaryl group having 5 to 20 ring atoms, at least one of $Ar_a$, $Ar_b$ and $Ar_c$ is an aryl group having 6 to 20 ring carbon atoms substituted with a heteroaryl group, an aryloxy group or a heteroaryloxy group, or a substituted or unsubstituted heteroaryl group having 5 to 20 ring atoms, $R_1$ to $R_6$ are independently a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group, two adjacent groups of $R_1$ to $R_6$ may be saturated or unsaturated divalent groups that are bonded each other to form a ring, a and f are independently an integer of 0 to 4, and b, c, d and e are independently an integer of 0 to 3.

5. The nitrogen-containing aromatic heterocyclic derivative according to any one of 1 to 4, wherein $Ar_a$, $Ar_b$ and $Ar_c$ are independently a phenyl group or a group represented by any of the following formulas (5-1) to (5-3):

(5-1)

(5-2)

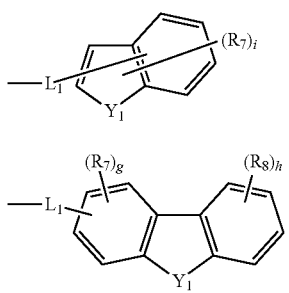

(5-3)

(10)

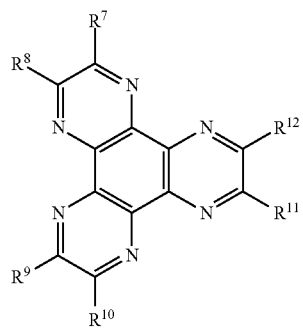

wherein $R_7$ and $R_8$ are independently are a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group, two adjacent $R_7$ and $R_8$ may be saturated or unsaturated divalent groups that are bonded each other to form a ring, $Y_1$ is an oxygen atom, a sulfur atom or NRd, Rd is a substituted or unsubstituted aryl group having 6 to 20 ring carbon atoms, or a substituted or unsubstituted heteroaryl group having 5 to 20 ring atoms, a substituent of Rd is a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group, $L_1$ is a single bond, a substituted or unsubstituted arylene group having 6 to 20 ring carbon atoms, or a substituted or unsubstituted heteroarylene group having 5 to 20 ring atoms, h is an integer of 0 to 4, g is an integer of 0 to 3, and i is an integer of 0 to 6.

6. The nitrogen-containing aromatic heterocyclic derivative according to any one of 1 to 5, which is a material for an organic electroluminescence device.

7. The nitrogen-containing aromatic heterocyclic derivative according to any one of 1 to 5, which is a hole-transporting material for an organic electroluminescence device.

8. An organic electroluminescence device comprising:
   a cathode;
   an anode; and
   one or more organic thin film layers between the cathode and the anode, wherein one or more of the organic thin film layers comprise the nitrogen-containing aromatic heterocyclic derivative according to any one of 1 to 7.

9. The organic electroluminescence device according to 8, wherein the one or more organic thin film layers comprise a hole-transporting layer and/or a hole-injecting layer, and the hole-transporting layer and/or the hole-injecting layer comprises the nitrogen-containing aromatic heterocyclic derivative.

10. The organic electroluminescence device according to 9, wherein the hole-transporting layer and/or the hole-injecting layer is in contact with a layer comprising a compound represented by the following formula (10):

wherein $R^7$ to $R^{12}$ are independently a cyano group, —$CONH_2$, a carboxy group or —$COOR^{13}$ wherein $R^{13}$ is an alkyl group having 1 to 20 carbon atoms, or $R^7$ and $R^8$, $R^9$ and $R^{10}$, or $R^{11}$ and $R^{12}$ are bonded each other to form —CO—O—CO—.

11. The organic electroluminescence device according to any one of 8 to 10, wherein the one or more organic thin film layers comprise an emitting layer, and the emitting layer comprises a phosphorescent emitting material.

12. The organic electroluminescence device according to any one of 8 to 10, wherein the one or more organic thin film layers comprise an emitting layer, and the emitting layer comprises a phosphorescent emitting material and the nitrogen-containing aromatic heterocyclic derivative as a host material.

13. The organic electroluminescence device according to 11 or 12, wherein the phosphorescent emitting material is an ortho-metalated complex of iridium (Ir), osmium (Os) or platinum (Pt) metal.

14. The organic electroluminescence device according to any one of 8 to 13, wherein the one or more organic thin film layers comprise an electron transporting layer, and the electron transporting layer comprises a nitrogen-containing aromatic heterocyclic derivative represented by any one of the following formulas:

(60)

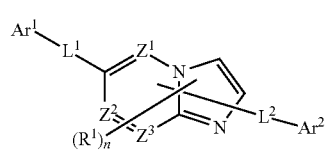

(61)

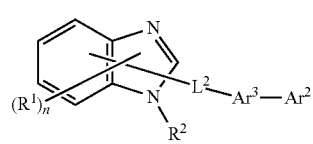

(62)

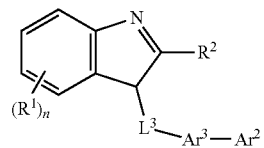

wherein $Z^1$, $Z^2$ and $Z^3$ are independently a nitrogen atom or a carbon atom, $R^1$ and $R^2$ are independently a substituted or unsubstituted aryl group having 6 to 50 ring carbon atoms, a substituted or unsubstituted heteroaryl group having 3 to 50 ring atoms, an alkyl group having 1 to 20 carbon atoms, an alkyl group having 1 to 20 carbon atoms substituted with a halogen atom, or an alkoxy group having 1 to 20 carbon atoms, n is an integer of 0 to 4, when n is an integer of 2 or more, R's may be the same or different, or two adjacent R's may be bonded each other to form a substituted or unsubstituted aromatic hydrocarbon ring, $Ar^1$ is a substituted or unsubstituted aryl group having 6 to 50 ring carbon atoms, or a substituted or unsubstituted heteroaryl group having 3 to 50 ring atoms, $Ar^2$ is a hydrogen atom, an alkyl group having 1 to 20 carbon atoms, an alkyl group having 1 to 20 carbon atoms substituted with a halogen atom, an alkoxy group having 1 to 20 carbon atoms, a substituted or unsubstituted aryl group having 6 to 50 ring carbon atoms, or a substituted or unsubstituted heteroaryl group having 3 to 50 ring atoms, in the formula (60), one of $Ar^1$ and $Ar^2$ is a substituted or unsubstituted fused aromatic hydrocarbon ring group having 10 to 50 ring carbon atoms, or a substituted or unsubstituted fused aromatic heterocyclic group having 9 to 50 ring atoms, $Ar^3$ is a substituted or unsubstituted arylene group having 6 to 50 ring carbon atoms, or a substituted or unsubstituted heteroarylene group having 3 to 50 ring atoms, and $L^1$, $L^2$ and $L^3$ are independently a single bond, a substituted or unsubstituted arylene group having 6 to 50 ring carbon atoms, or a substituted or unsubstituted hetero fused ring group having 9 to 50 ring atoms.

According to the invention, a novel compound which can be used for an organic EL device can be provided. When the compound of the invention is used for a host-transporting material and the like, an organic EL device having high luminous efficiency, low-voltage driving, and a long life time can be achieved.

MODE FOR CARRYING OUT THE INVENTION

The nitrogen-containing aromatic heterocyclic derivative of the invention is represented by the following formula (1):

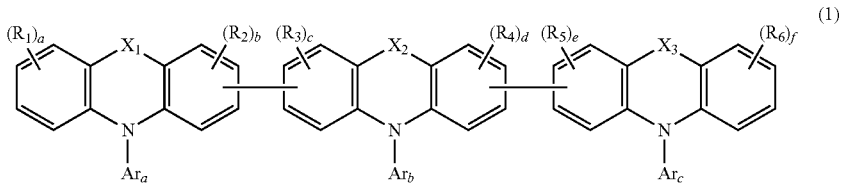

In the formula (1), $X_1$ to $X_3$ are independently a single bond, CRaRb, NRc, an oxygen atom or a sulfur atom.

Ra, Rb and Rc are independently a linear or branched alkyl group having 1 to 15 carbon atoms, a cycloalkyl group having 3 to 15 carbon atoms, an aryl group having 6 to 20 ring carbon atoms or a heteroaryl group having 5 to 20 ring atoms.

$Ar_a$, $Ar_b$ and $Ar_c$ are independently a substituted or unsubstituted aryl group having 6 to 20 ring carbon atoms or a substituted or unsubstituted heteroaryl group having 5 to 20 ring atoms.

When all of $X_1$ to $X_3$ is a single bond, at least one of $Ar_a$, $Ar_b$ and $Ar_c$ is an aryl group having 6 to 20 ring carbon atoms substituted with a heteroaryl group, an aryloxy group or a heteroaryloxy group, or a substituted or unsubstituted heteroaryl group having 5 to 20 ring atoms.

A substituent of $Ar_a$, $Ar_b$ and $Ar_c$ includes a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group.

$R_1$ to $R_6$ are independently a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group. Two adjacent groups of $R_1$ to $R_6$ may be saturated or unsaturated divalent groups that are bonded each other to form a ring.

a and f are independently an integer of 0 to 4.

b, c, d and e are independently an integer of 0 to 3.

In this specification, the "ring carbon atom" means a carbon atom which constitutes a saturated ring, an unsaturated ring or an aromatic ring. The "ring atom" means a carbon atom or a hetero atom which constitutes these rings.

The "unsubstituted" means a substitution with a hydrogen atom, and the hydrogen atom of the invention includes light hydrogen, deuterium and tritiated hydrogen.

The aryl group includes a monocyclic aromatic hydrocarbon ring (also referred to simply as an aromatic hydrocarbon ring) and a fused aromatic hydrocarbon ring. The heteroaryl group includes a monocyclic aromatic heterocyclic ring (also referred to simply as an aromatic heterocyclic ring) and a fused aromatic heterocyclic ring. Preferably, the aryl group and the heteroaryl group are one monocyclic ring or one fused ring.

As shown by the formula (1), the nitrogen-containing aromatic heterocyclic derivative of the invention is characterized in having the structure wherein three nitrogen-containing aromatic heterocyclic rings are connected each other via an endocyclic benzene ring.

When nitrogen-containing aromatic heterocyclic rings are connected each other via an endocyclic benzene ring, an unshared electron pair of nitrogen atom in the heterocyclic ring has an electron-donating effect due to its existing in the same planar surface as the endocyclic benzene ring. Therefore, the nitrogen-containing aromatic heterocyclic ring functions as an electron-donating substituent and increases an electron density in the whole molecule.

Further, due to the fact that three nitrogen-containing aromatic heterocyclic rings are connected via an endocyclic benzene ring, an electron density in the whole molecule is much more increased and Ip (ionization potential) is decreased. Accordingly, by use of the nitrogen-containing aromatic heterocyclic derivative of the invention as a hole-transporting layer in contact with an emitting layer, an injection of a hole into the emitting layer is facilitated, and in the result, a driving voltage of the organic EL device can be reduced.

When $X_1$ to $X_3$, which are the cites for crosslinking benzene rings in the nitrogen-containing aromatic heterocyclic ring, are any of CRaRb (C is a carbon atom), NRc (N is a nitrogen atom), an oxygen atom and a sulfur atom, an electron density in the ring is increased and Ip is decreased compared with the case where they are single bonds.

On the other hand, when all of $X_1$ to $X_3$ is a single bond, by introducing into at least one of $Ar_a$, $Ar_b$ and $Ar_c$ an aryl group having 6 to 20 ring carbon atoms substituted by a heteroaryl group, an aryloxy group or a heteroaryloxy group, or a substituted or unsubstituted heteroaryl group having 5 to 20 ring atoms, an effect by a hetero atom contained in such substituents increases an electron density and decreases Ip.

The nitrogen-containing aromatic heterocyclic derivative of the invention has increased singlet energy gap and triplet energy gap as a result of being constituted with nitrogen-containing aromatic heterocyclic rings only, compared with the conventional hole-transporting material having a triphenylamine structure such as NPD and the like. Therefore, use of the derivative as a hole-transporting material in contact with an emitting layer enables charge and exciton to be effectively enclosed within the emitting layer, thereby improving luminous efficiency. In particular, since triplet energy gap is greater, the derivative can be used effectively in combination with a phosphorescent emitting layer.

Further, the nitrogen-containing aromatic heterocyclic derivative of the invention can be used for a phosphorescent host.

In addition, since singlet energy gap is greater, Af (affinity) is reduced and electron resistance is improved, and therefore, a life time of the organic EL device can be improved.

The nitrogen-containing aromatic heterocyclic derivative of the invention is preferably represented by the following formula (2):

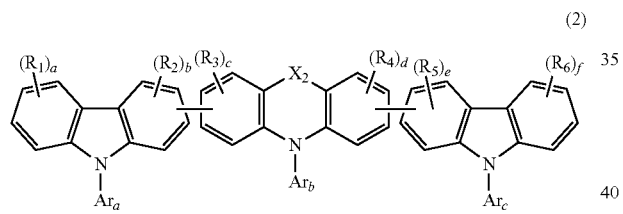

(2)

In the formula (2), $X_2$, $R_1$ to $R_6$, $Ar_a$, $Ar_b$, $Ar_c$ and a to f are the same as those in the formula (1).

When $X_2$ is a single bond, at least one of $Ar_a$, $Ar_b$ and $Ar_c$ is an aryl group having 6 to 20 ring carbon atoms substituted with a heteroaryl group, an aryloxy group or a heteroaryloxy group, or a substituted or unsubstituted heteroaryl group having 5 to 20 ring atoms.

The nitrogen-containing aromatic heterocyclic derivative of the invention is more preferably represented by the following formula (3):

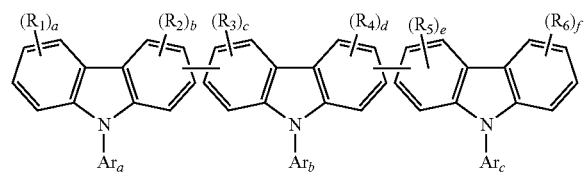

(3)

In the formula (3), $R_1$ to $R_6$, $Ar_a$, $Ar_b$, $Ar_c$ and a to f are the same as those in the formula (1).

At least one of $Ar_a$, $Ar_b$ and $Ar_c$ is an aryl group having 6 to 20 ring carbon atoms substituted with a heteroaryl group, an aryloxy group or a heteroaryloxy group, or a substituted or unsubstituted heteroaryl group having 5 to 20 ring atoms.

The nitrogen-containing aromatic heterocyclic derivative of the invention is more preferably represented by the following formula (4):

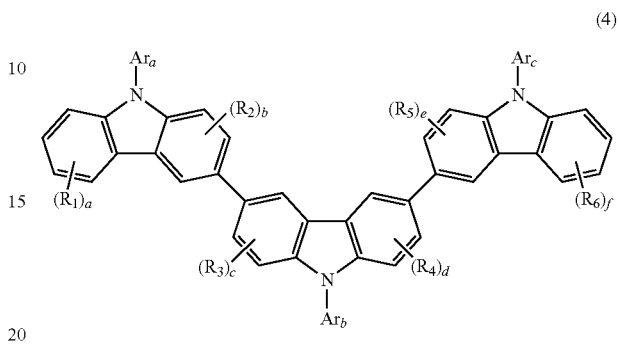

(4)

In the formula (4), $R_1$ to $R_6$, $Ar_a$, $Ar_b$, $Ar_c$ and a to f are the same as those in the formula (1).

At least one of $Ar_a$, $Ar_b$ and $Ar_c$ is an aryl group having 6 to 20 ring carbon atoms substituted with a heteroaryl group, an aryloxy group or a heteroaryloxy group, or a substituted or unsubstituted heteroaryl group having 5 to 20 ring atoms.

In the formulas (1) to (4), $Ar_a$, $Ar_b$ and $Ar_c$ are preferably independently a phenyl group or a group represented by any of the following formulas (5-1) to (5-3), except for a case that all of $Ar_a$, $Ar_b$ and $Ar_c$ is a phenyl group. When all of $X_1$ to $X_3$ is a single bond, it is preferable that $Ar_a$ and $Ar_c$ be a phenyl group and $Ar_b$ be any of the following formulas (5-1) to (5-3) (more preferably the formula (5-3)).

(5-1)

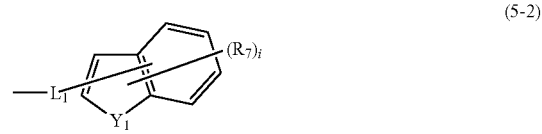

(5-2)

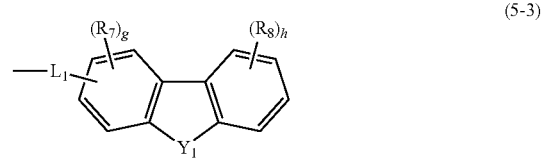

(5-3)

In the formulas (5-1) to (5-3), $R_7$ and $R_8$ are independently a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group. Two adjacent $R_7$ and $R_8$ may be saturated or unsaturated divalent groups that are bonded each other to form a ring.

$Y_1$ is an oxygen atom, a sulfur atom or NRd. Rd is a substituted or unsubstituted aryl group having 6 to 20 ring carbon atoms, or a substituted or unsubstituted heteroaryl group having 5 to 20 ring atoms. A substituent of Rd is a linear or branched alkyl group having 1 to 15 carbon atoms, a cycloalkyl group having 3 to 15 carbon atoms, a substituted or unsubstituted silyl group, an aryl group having 6 to 20 ring carbon atoms, a heteroaryl group having 5 to 20 ring atoms, a halogen atom or a cyano group.

$L_1$ is a single bond, a substituted or unsubstituted arylene group having 6 to 20 ring carbon atoms, or a substituted or unsubstituted heteroarylene group having 5 to 20 ring atoms.

h is an integer of 0 to 4, g is an integer of 0 to 3, and i is an integer of 0 to 6.

Each group in the formulas above and substituents thereof will be specified in detail below.

As the alkyl group, a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group and the like can be given.

The alkyl group preferably has 1 to 15 carbon atoms, more preferably 1 to 10 carbon atoms, and further preferably 1 to 6 carbon atoms. Of these, a methyl group, an ethyl group, a propyl group, an isopropyl group, a n-butyl group, a s-butyl group, an isobutyl group, a t-butyl group, a n-pentyl group and a n-hexyl group are preferable.

As the cycloalkyl group, a cyclopropyl group, a cyclobutyl group, a cyclopentyl group, a cyclohexyl group, an adamantyl group, a norbornyl group and the like can be given. The cycloalkyl group preferably has 3 to 10 ring carbon atoms, and more preferably 3 to 8 ring carbon atoms.

As the aryl group, a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a naphthacenyl group, a pyrenyl group, a chrysenyl group, a benzo[c]phenanthryl group, a benzo[g]chrysenyl group, a triphenylenyl group, a 1-fluorenyl group, a 2-fluorenyl group, a 3-fluorenyl group, a 4-fluorenyl group, a 9-fluorenyl group, a benzofluorenyl group, a dibenzofluorenyl group, a 2-biphenylyl group, a 3-biphenylyl group, a 4-biphenylyl group, a terphenyl group, a fluoranthenyl group and the like can be given.

As the arylene group, a divalent group corresponding to each of the above aryl groups can be given.

The aryl group preferably has 6 to 20 ring carbon atoms, and more preferably 6 to 12 ring carbon atoms. Of the foregoing aryl groups, a phenyl group, a biphenyl group, a tolyl group, a xylyl group and a 1-naphthyl group are particularly preferable.

As the heteroaryl group, a pyrrolyl group, a pyrazinyl group, a pyridinyl group, an indolyl group, an isoindolyl group, an imidazolyl group, a furyl group, a benzofuranyl group, an isobenzofuranyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a quinolyl group, an isoquinolyl group, a quinoxalinyl group, a 1-carbazolyl group, a 2-carbazolyl group, a 3-carbazolyl group, a 4-carbazolyl group, a 9-carbazolyl group, a phenanthridinyl group, an acrydinyl group, a phenanthrolinyl group, a phenadinyl group, a phenothiazinyl group, a phenoxazinyl group, an oxazolyl group, an oxadiazolyl group, a furazanyl group, a thienyl group, a benzothiophenyl group and the like can be given.

The heteroaryl group preferably has 5 to 20 ring atoms, and more preferably 5 to 14 ring atoms.

Preferably, the heteroaryl group is a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-carbazolyl group, a 2-carbazolyl group, a 3-carbazolyl group, a 4-carbazolyl group, or a 9-carbazolyl group.

As the substituted silyl group, an alkylsilyl group having 3 to 30 carbon atoms (for example, a trialkylsilyl group having 3 to 10 carbon atoms), an arylsilyl group having 8 to 30 carbon atoms (for example, a triarylsilyl group having 18 to 30 carbon atoms), and an alkylarylsilyl group having 8 to 15 carbon atoms (the ring carbon atoms of the aryl part can be 6 to 14) can be given, and for example, a trimethylsilyl group, a triethylsilyl group, a t-butyldimethylsilyl group, a vinyldimethylsilyl group, a propyldimethylsilyl group, a triisopropylsilyl group, a triphenylsilyl group and the like can be given.

As the halogen atom, fluorine, chlorine, bromine, iodine and the like can be given, and the halogen atom is preferably a fluorine atom.

The aryloxy group is represented by —OZ, and examples of Z are the same as those of the aryl group.

The aryl group contained in the aryloxy group preferably has 6 to 20 ring carbon atoms, and more preferably 6 to 12 ring carbon atoms. Of the foregoing aryl groups, a phenyl group, a biphenyl group, a tolyl group, a xylyl group and a 1-naphthyl group are particularly preferable.

The heteroaryloxy group is represented by —OY, and examples of Y are the same as those of the heteroaryl group.

The heteroaryl group contained in the heteroaryloxy group preferably has 5 to 20 ring atoms, and more preferably 5 to 14 ring atoms. A 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl, and a 4-dibenzothiophenyl group are particularly preferable.

As the aryl group having 6 to 20 carbon atoms substituted with an aryloxy group, a phenoxyphenyl group, a phenoxynaphthyl group, a naphthoxyphenyl group, a biphenyloxyphenyl group and the like can be given.

As the aryl group having 6 to 20 carbon atoms substituted with an heteroaryloxy group, a dibenzofuran-1-yloxyphenyl group, a dibenzofuran-2-yloxyphenyl group, a dibenzofuran-3-yloxyphenyl group, a dibenzofuran-4-yloxyphenyl group, a dibenzothiophen-1-yloxyphenyl group, a dibenzothiophen-2-yloxyphenyl group, a dibenzothiophen-3-yloxyphenyl group, a dibenzothiophen-4-yloxyphenyl group, a benzofuran-2-yloxyphenyl group, a benzofuran-3-yloxyphenyl group, a benzothiophen-2-yloxyphenyl group, a benzothiophen-3-yloxyphenyl group, a 1-phenylindole-2-yloxyphenyl group, a 1-phenylindole-3-yloxyphenyl group and the like can be given.

The aryloxy group and the heteroaryloxy group are stable against an oxidizing condition relative to the alkoxy group, and improve a life time of the organic EL device.

As the aryl group having 6 to 20 carbon atoms substituted with an heteroaryl group, a dibenzofuran-1-ylphenyl group, a dibenzofuran-2-ylphenyl group, a dibenzofuran-3-ylphenyl group, a dibenzofuran-4-ylphenyl group, a dibenzothiophen-1-ylphenyl group, a dibenzothiophen-2-ylphenyl group, a dibenzothiophen-3-ylphenyl group, a dibenzothiophen-4-ylphenyl group, a carbazole-9-ylphenyl group, a benzofuran-2-ylphenyl group, a benzofuran-3-ylphenyl group, a benzothiophen-2-ylphenyl group, a benzothiophen-3-ylphenyl group, a 1-phenylindole-2-ylphenyl group, a 1-phenylindole-3-ylphenyl group, a 5-phenylfuran-2-ylphenyl group, a 5-phenylthiophen-2-ylphenyl group and the like can be given.

Specific examples of the nitrogen-containing aromatic heterocyclic derivative of the invention are given below.

-continued
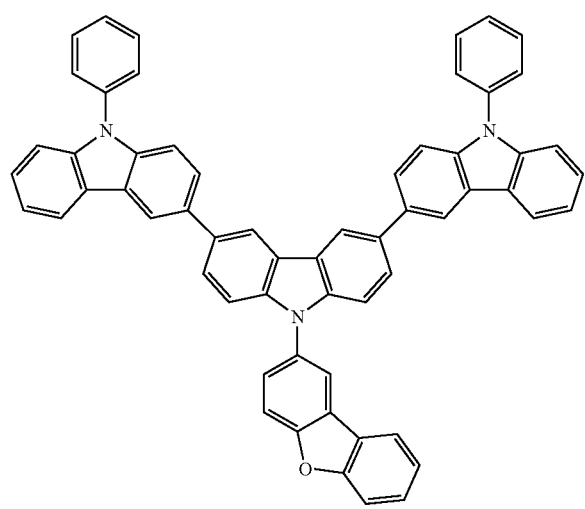
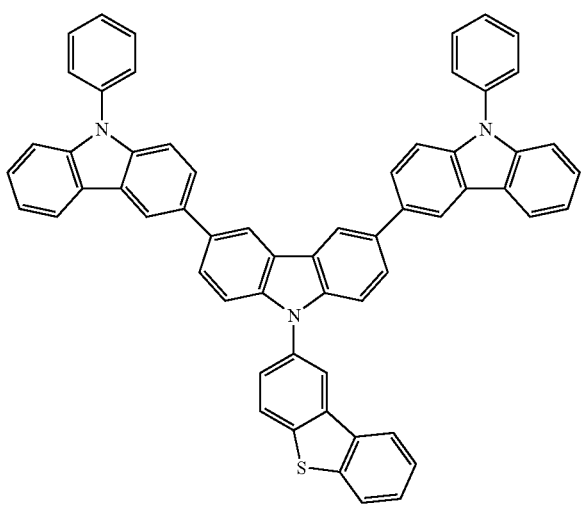
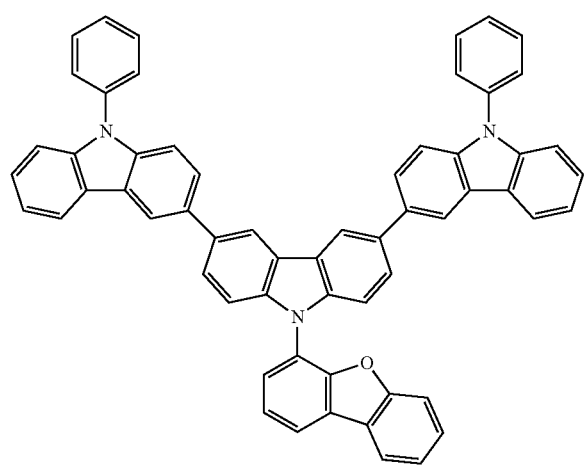
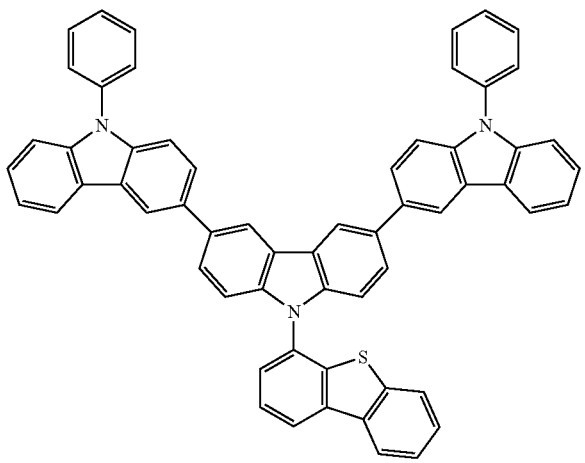

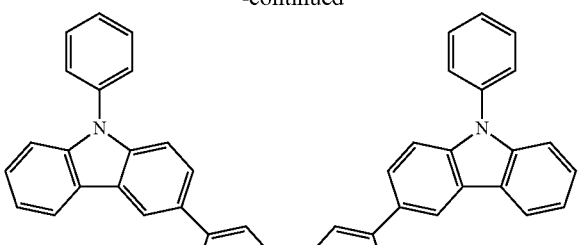
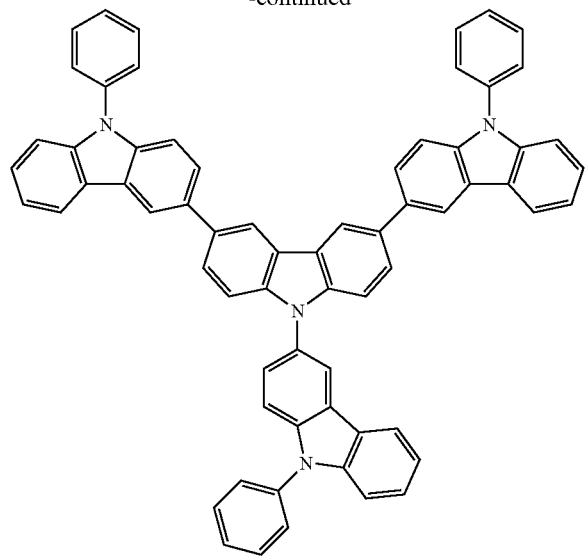
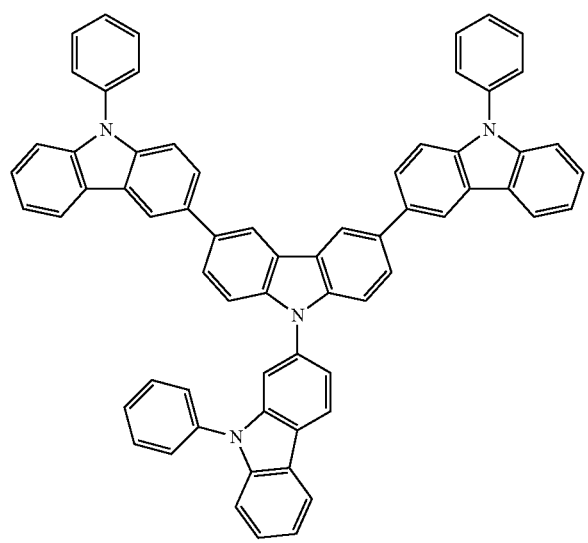
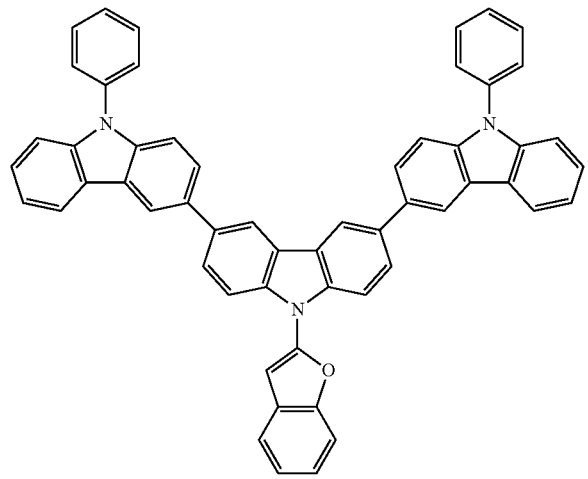

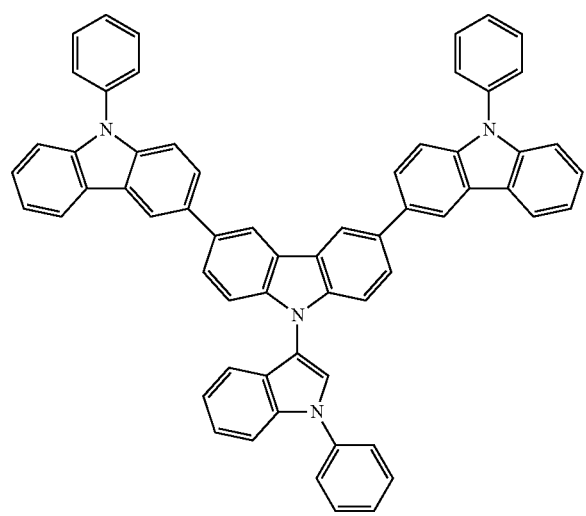
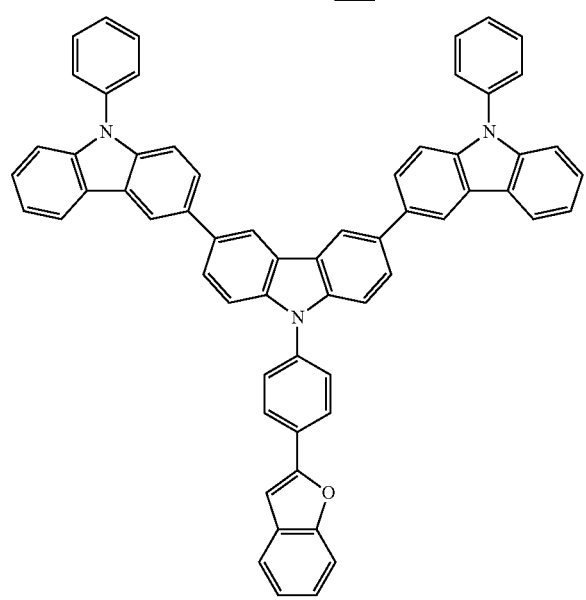
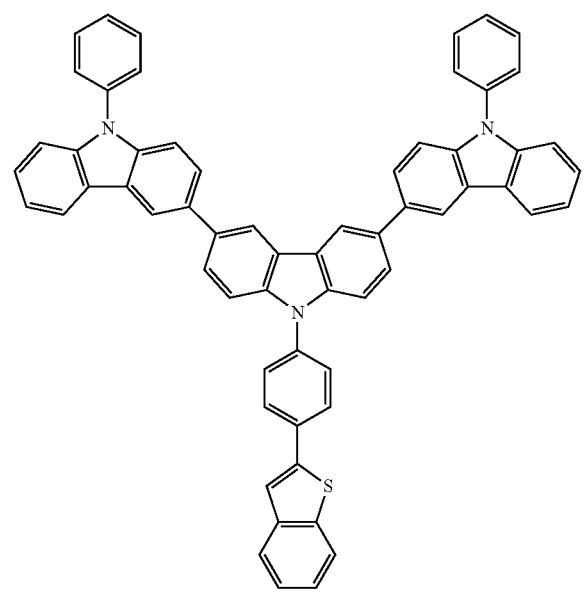
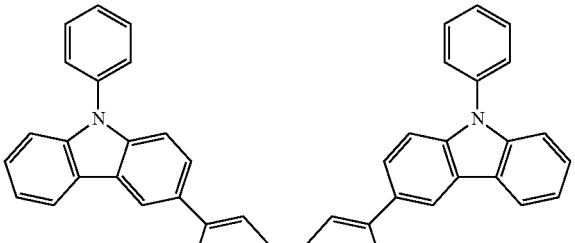
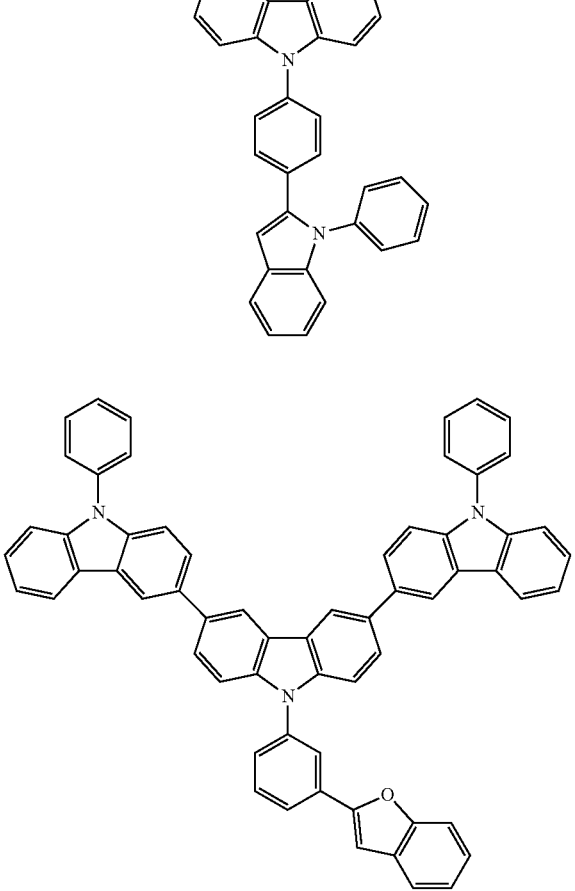
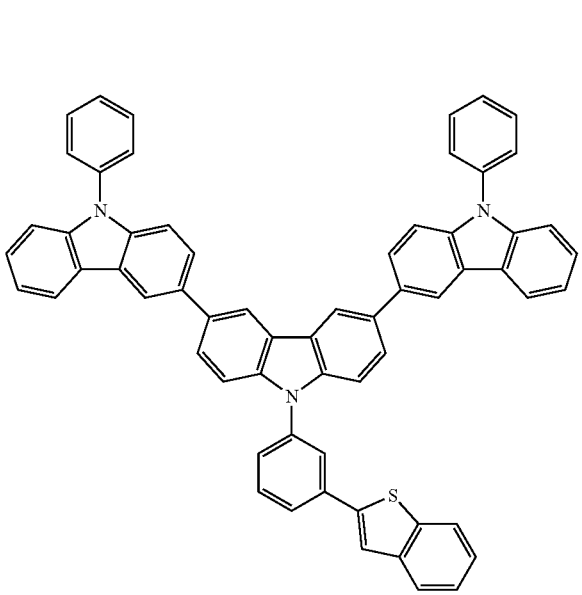

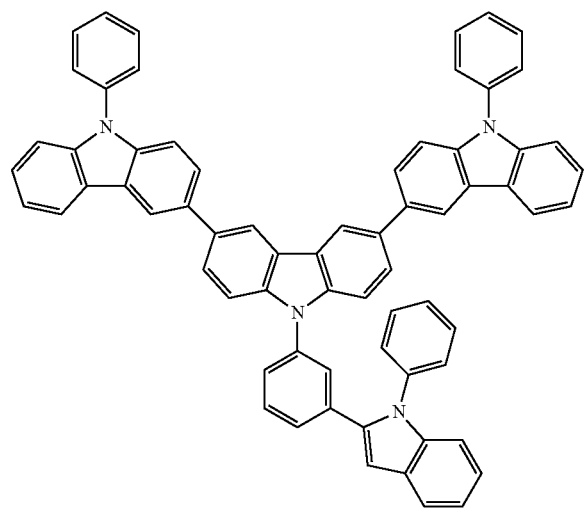
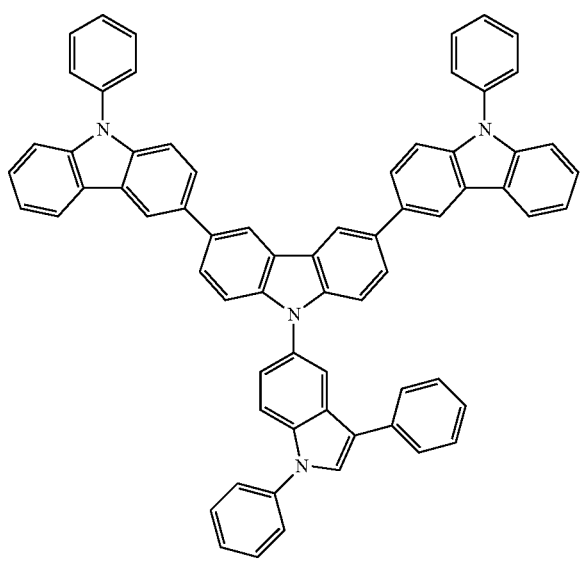
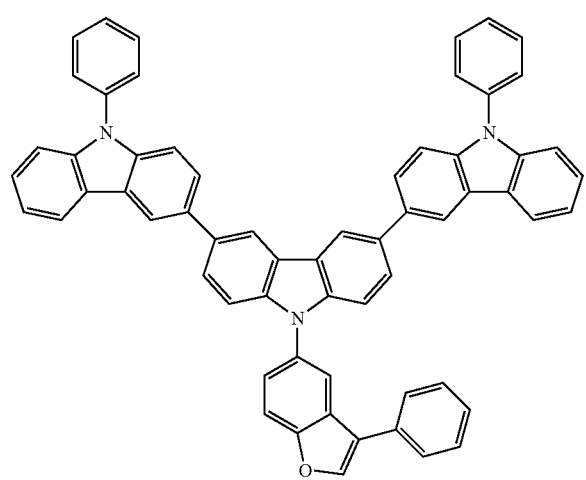
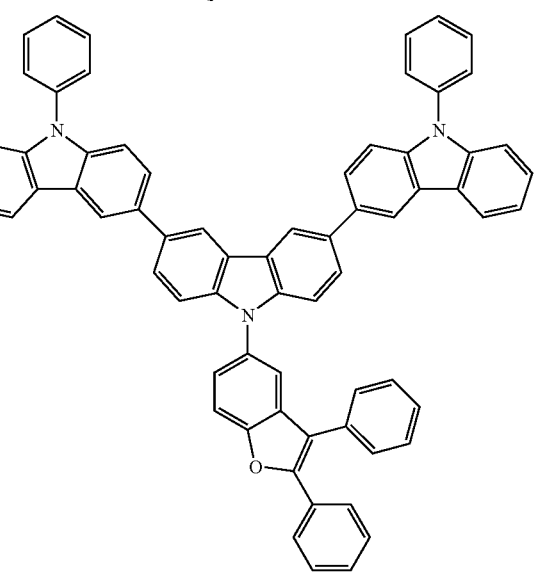
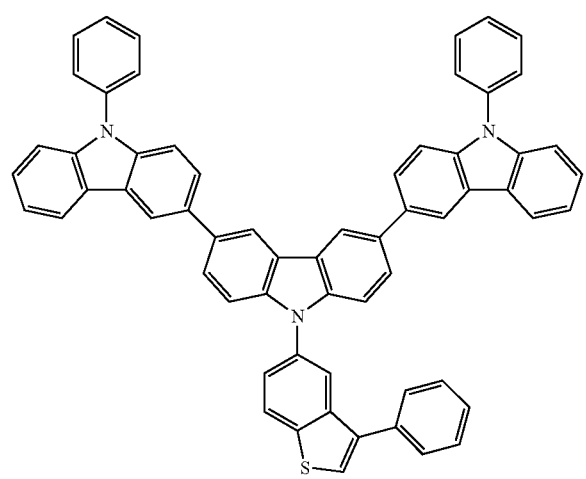
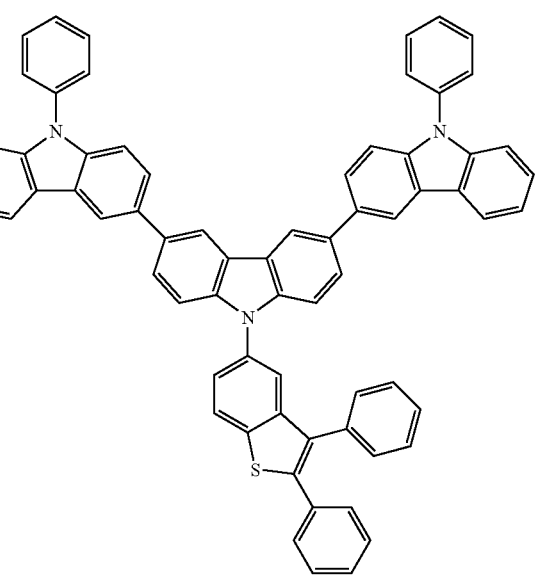

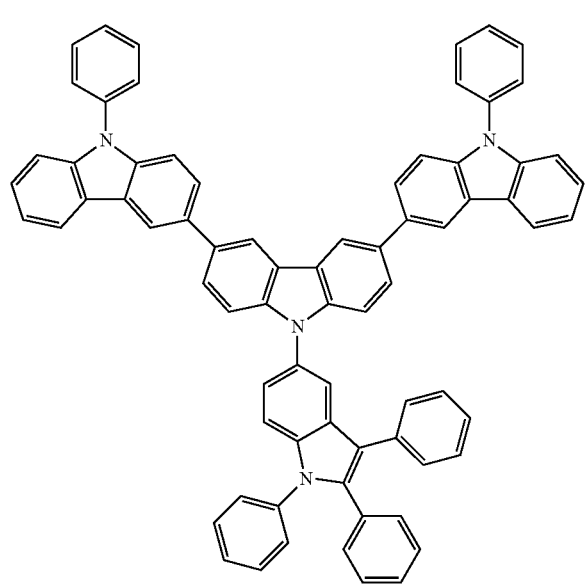
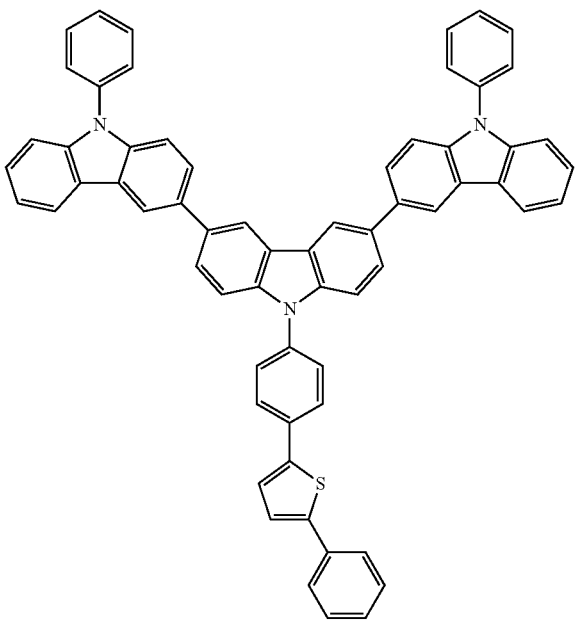
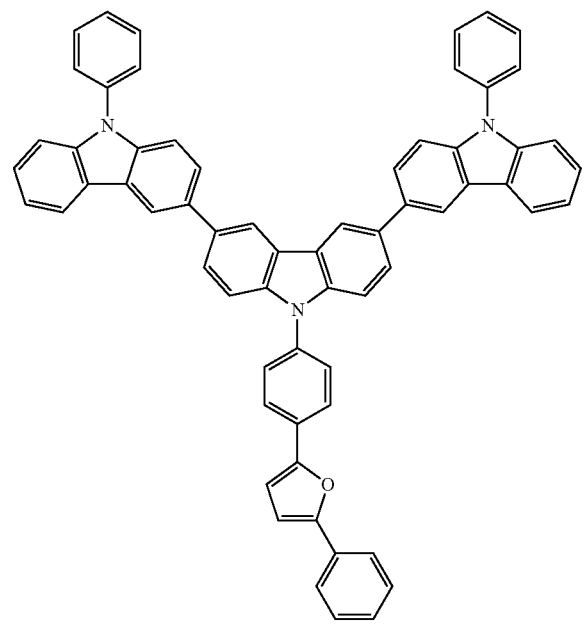
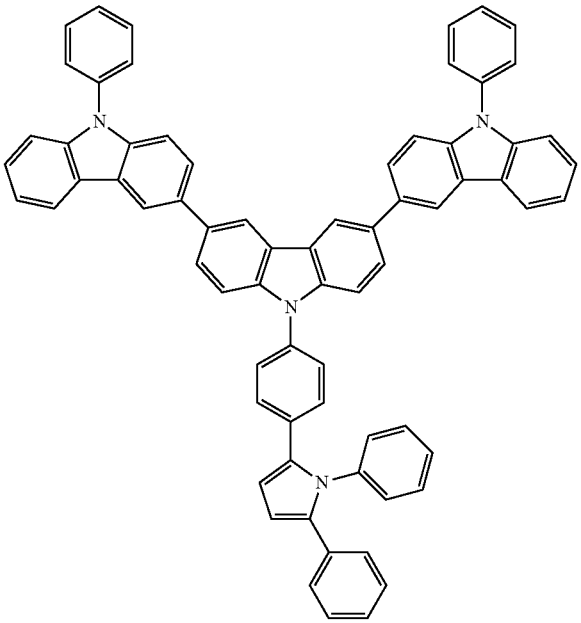

-continued
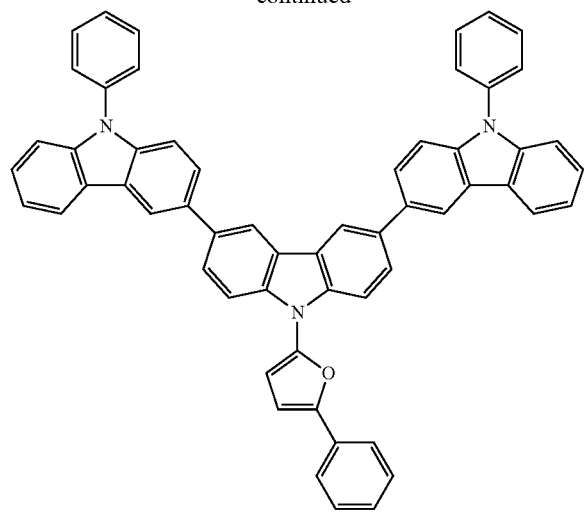
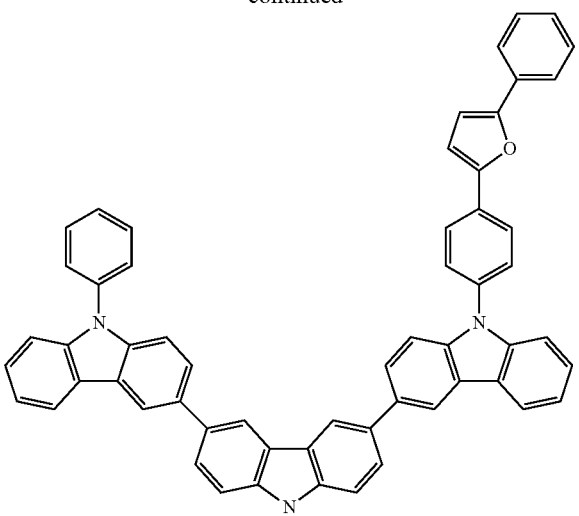
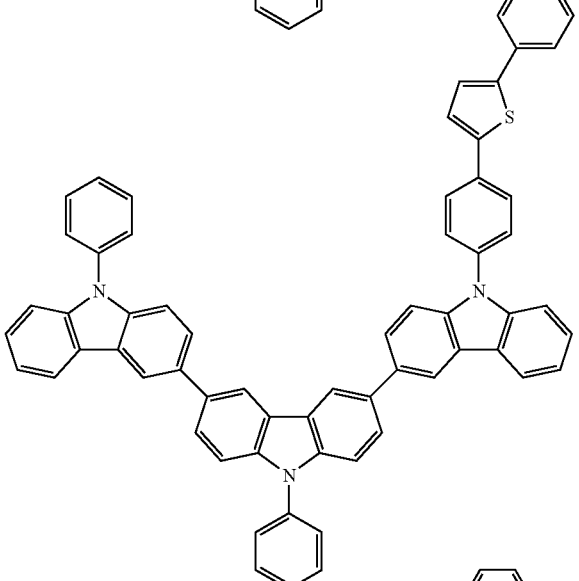
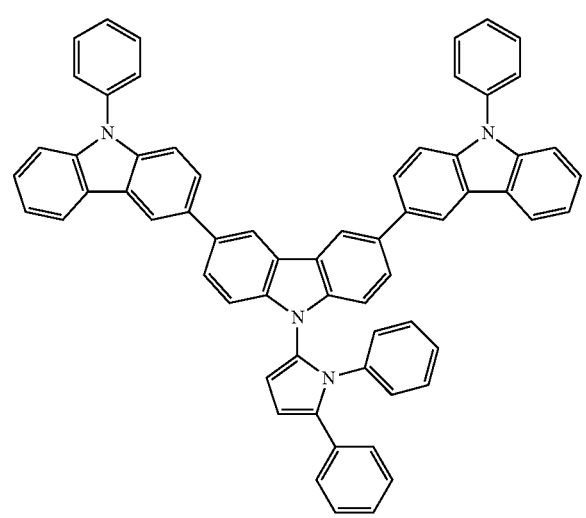
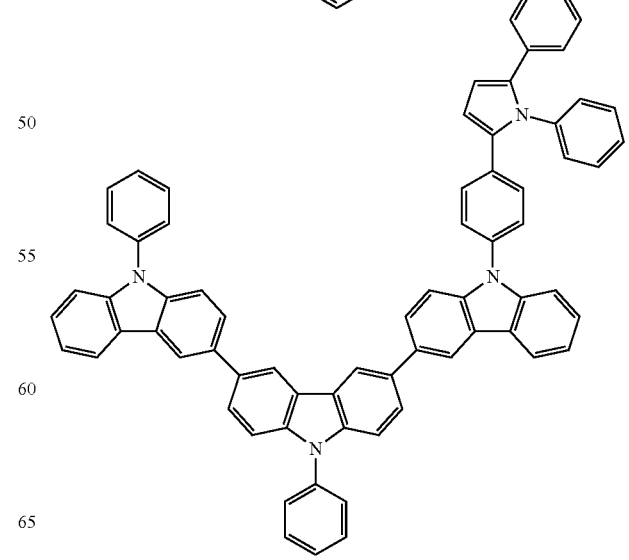

-continued
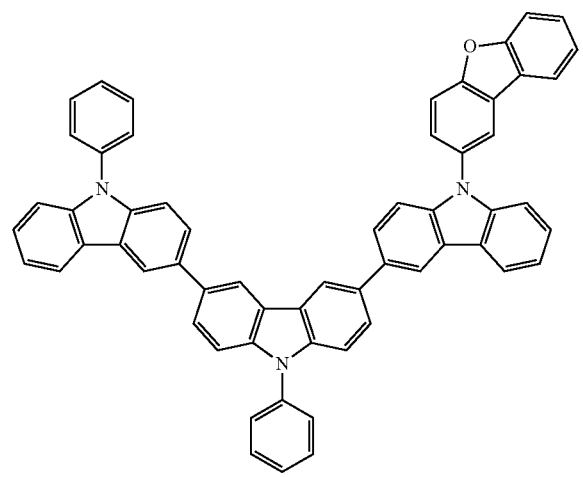
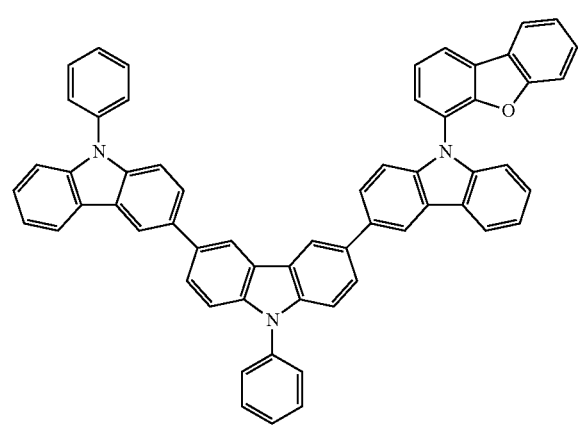
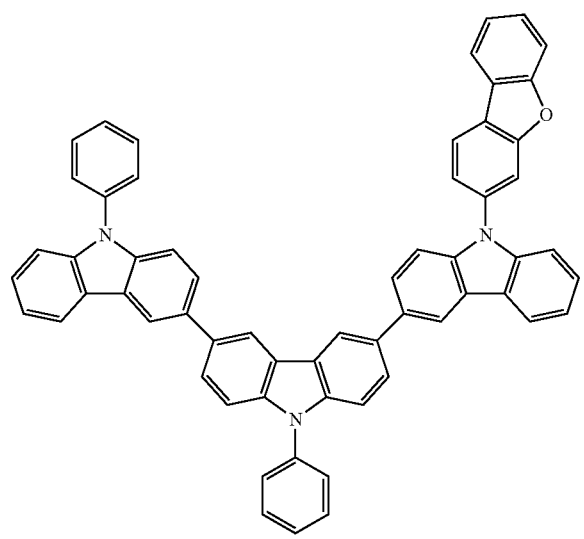
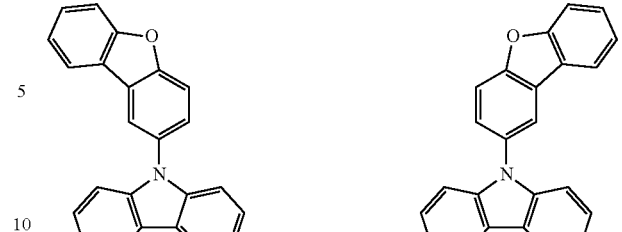
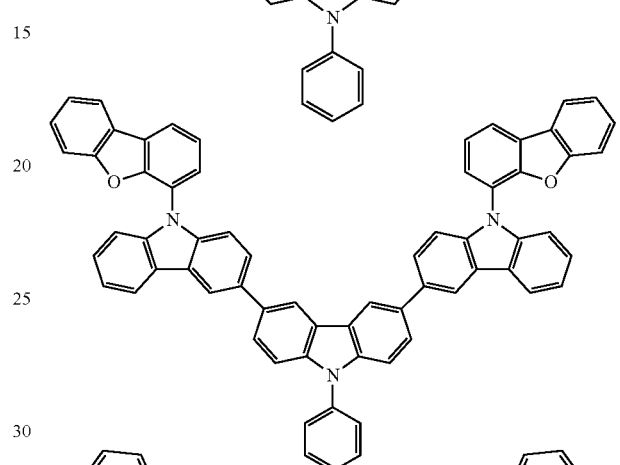
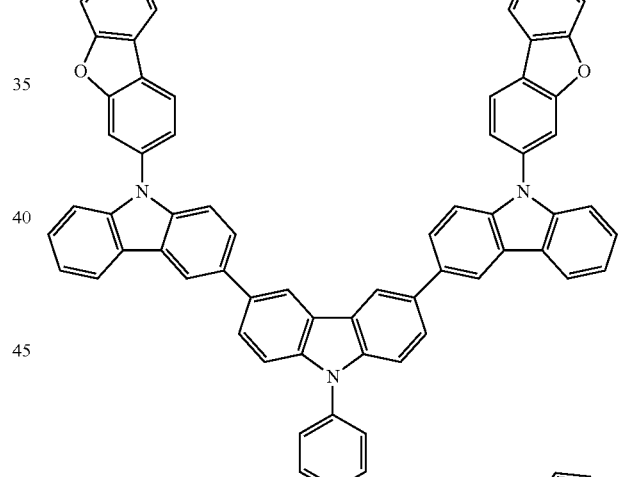
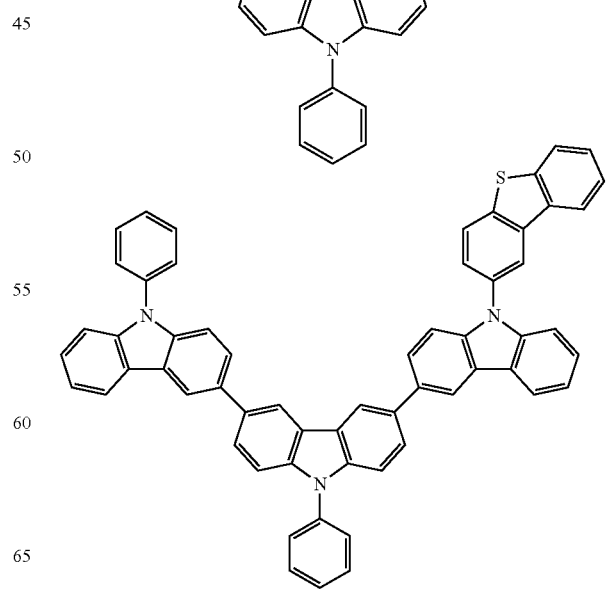

-continued
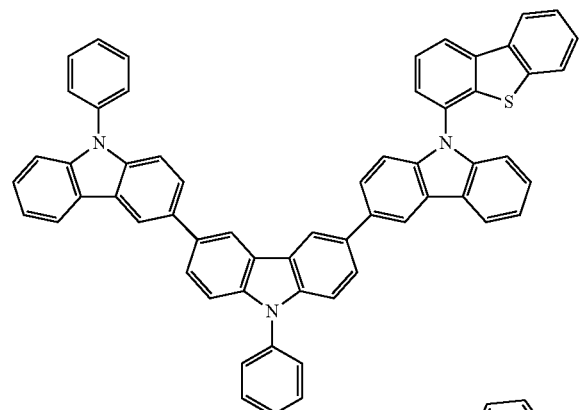
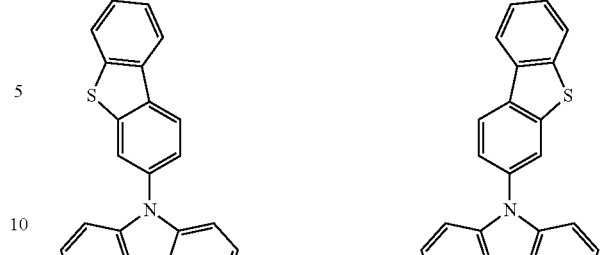
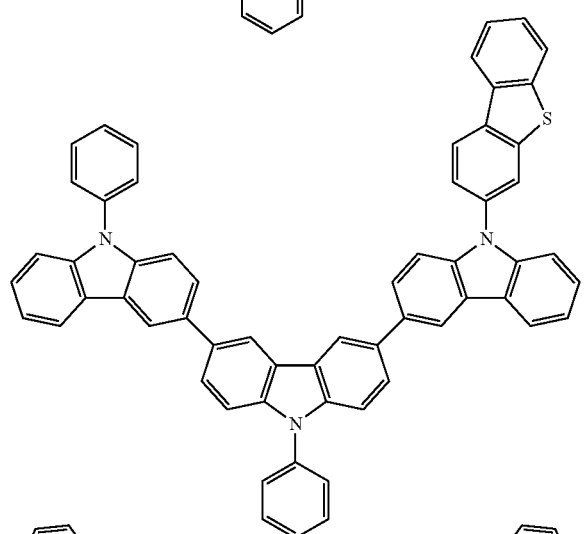
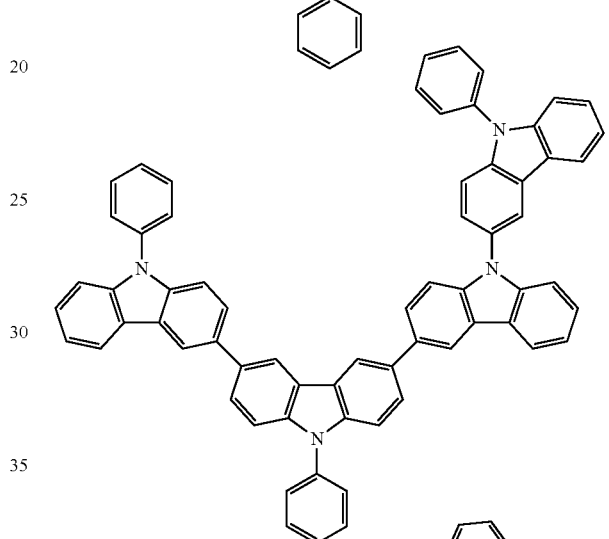
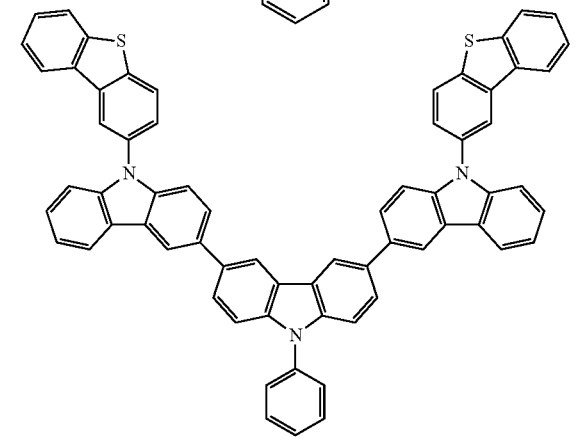
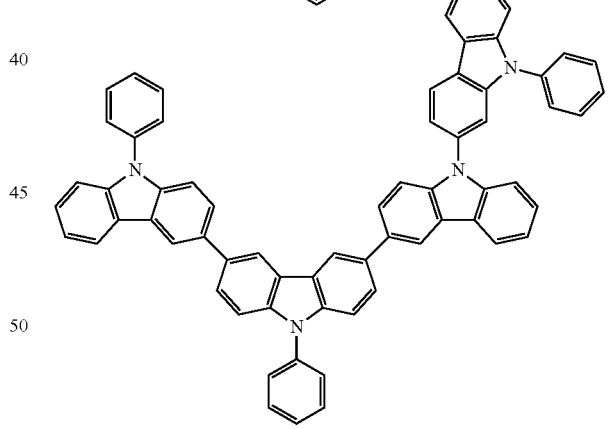
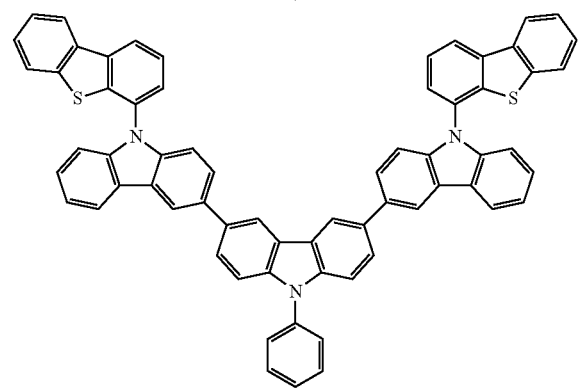
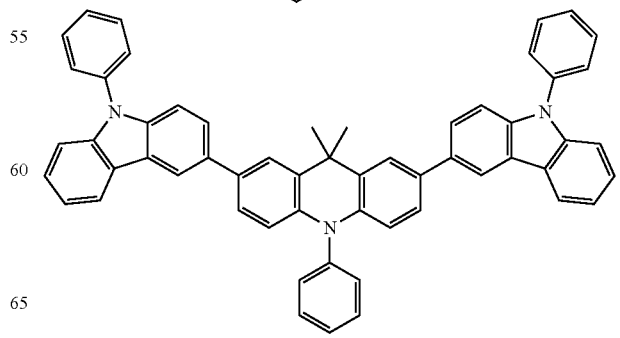

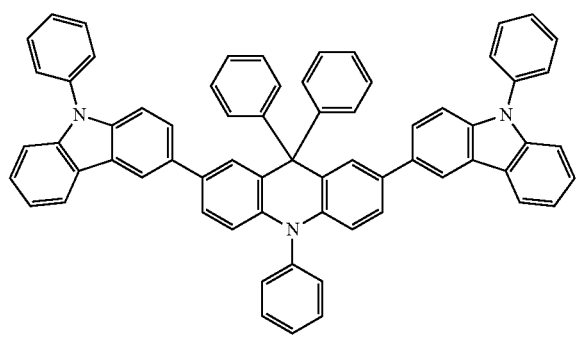
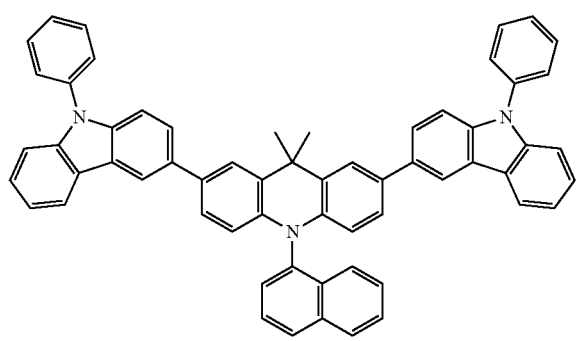
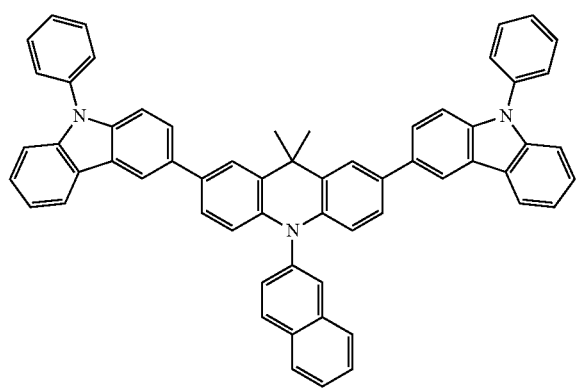
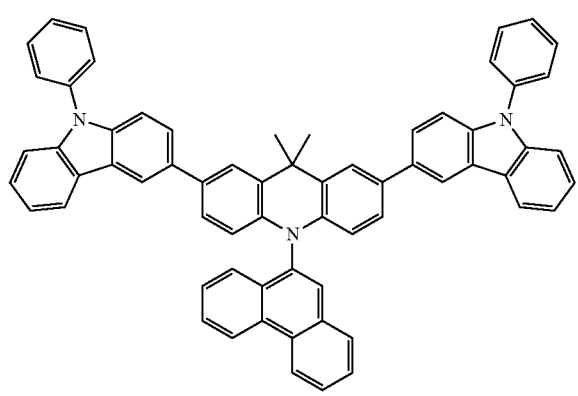
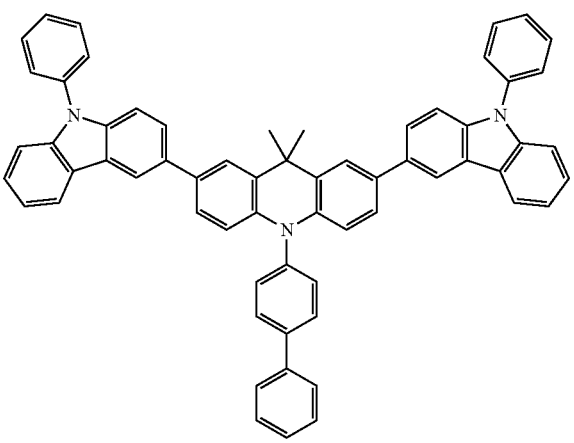
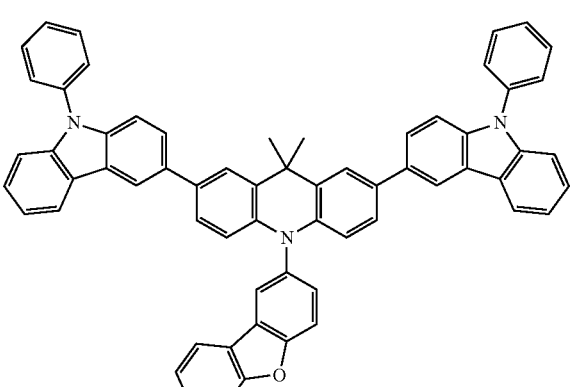
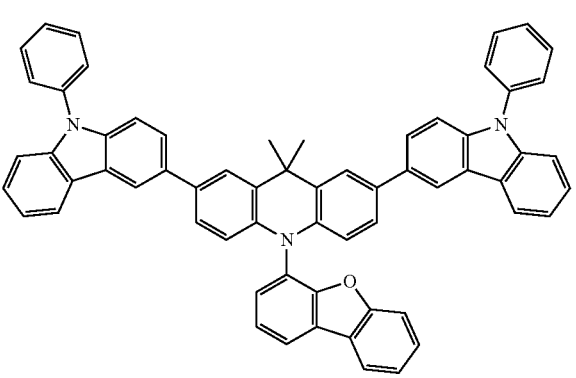

31
-continued
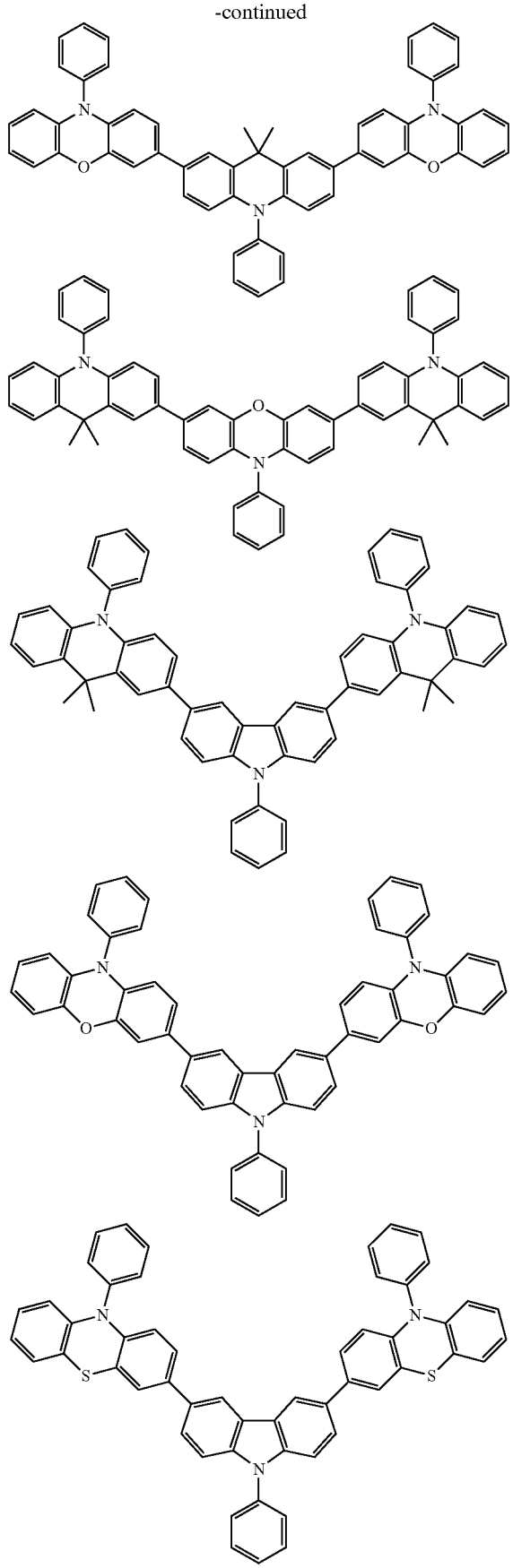
32
-continued
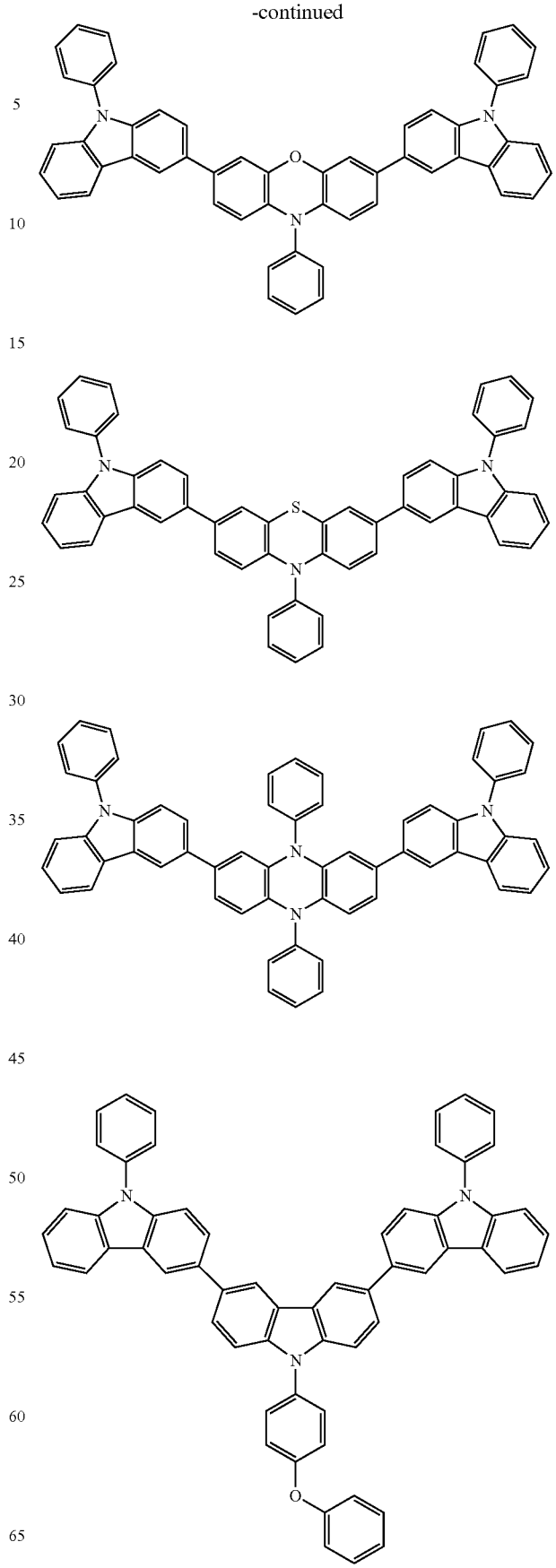

33
-continued
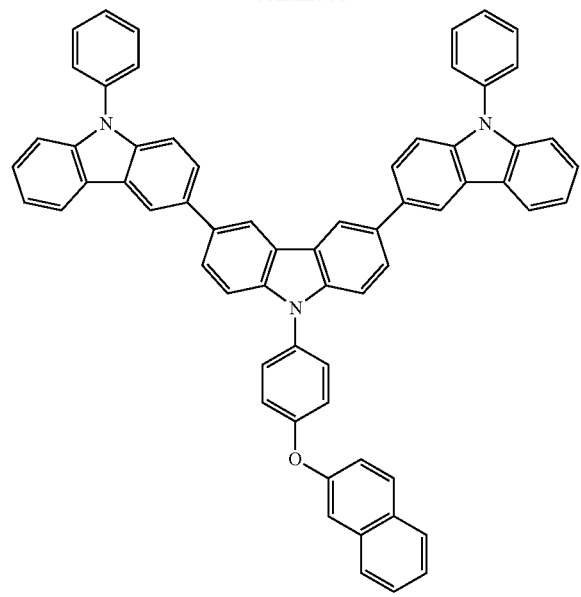
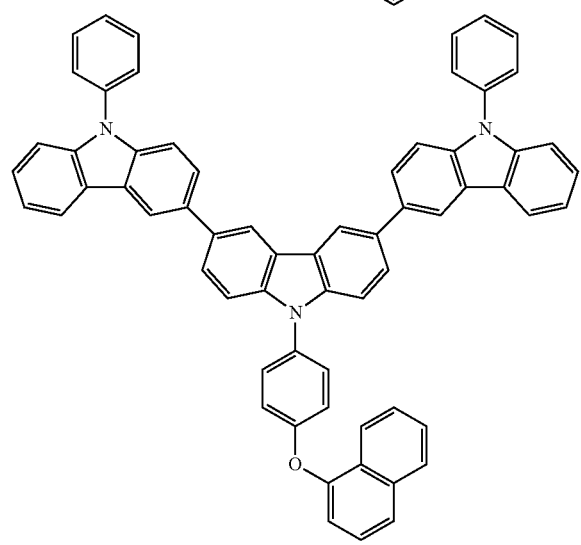
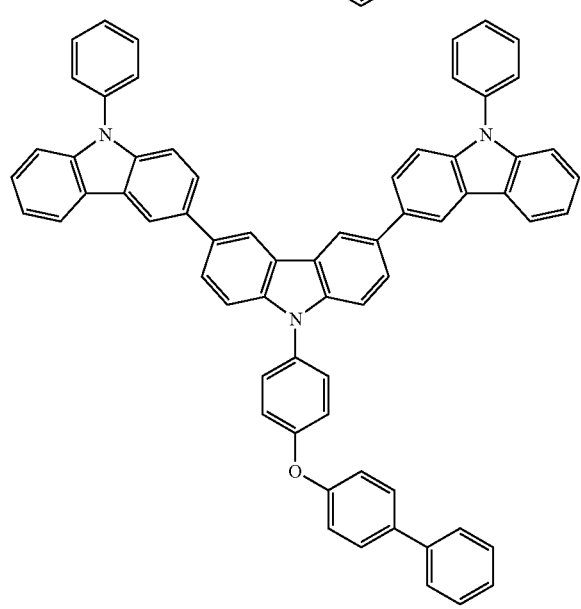
34
-continued
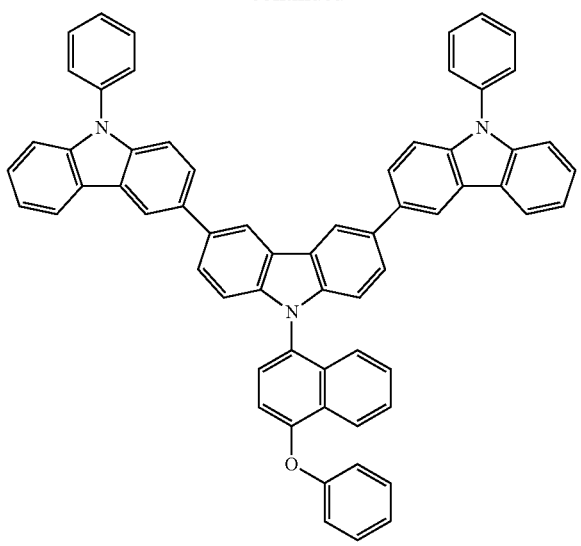
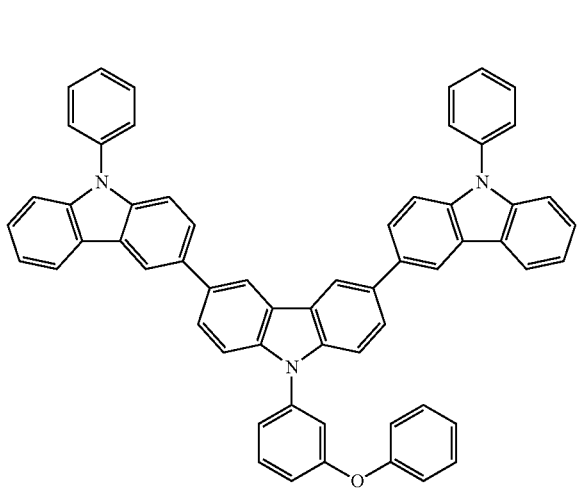
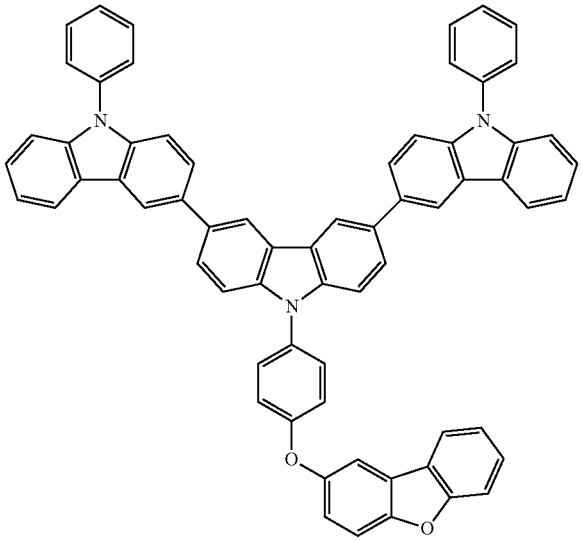

35
-continued
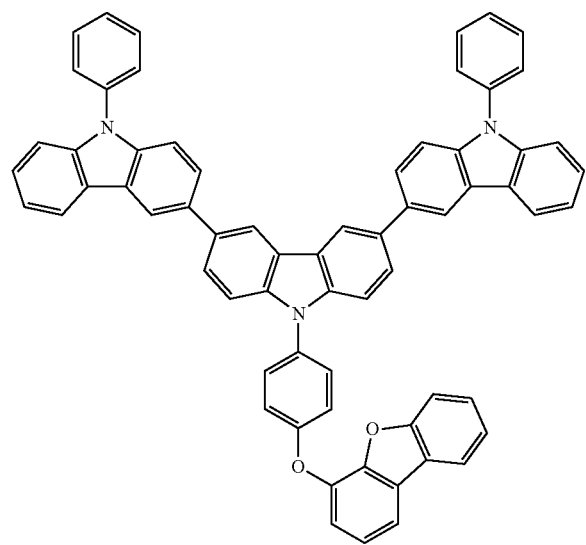
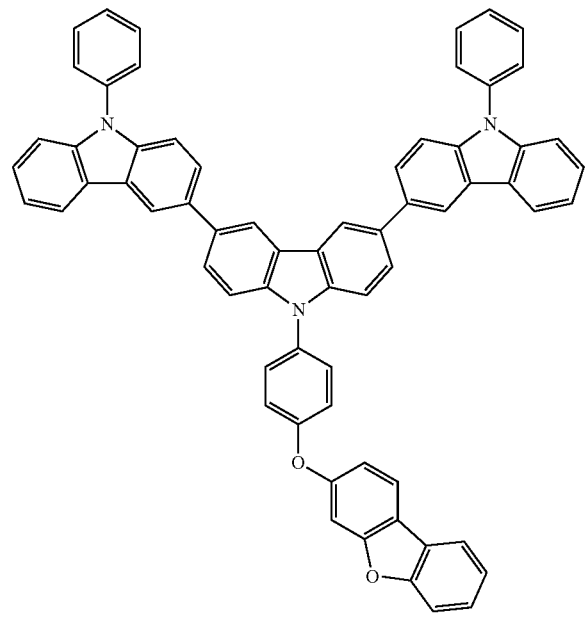
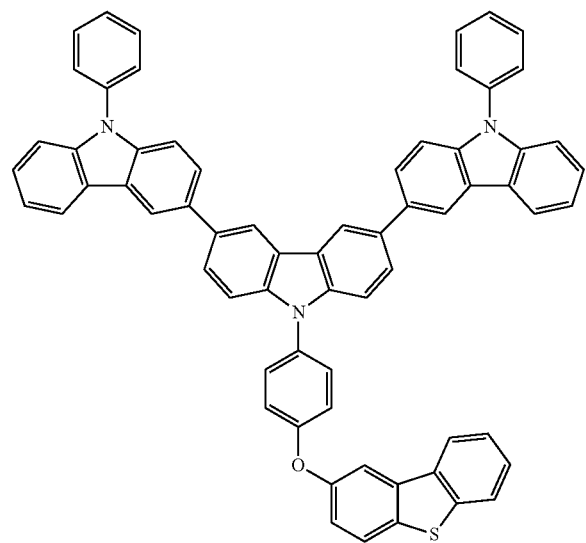
36
-continued
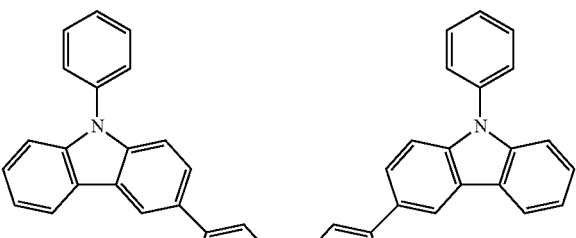
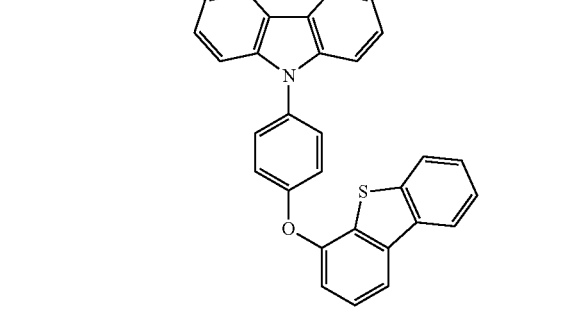
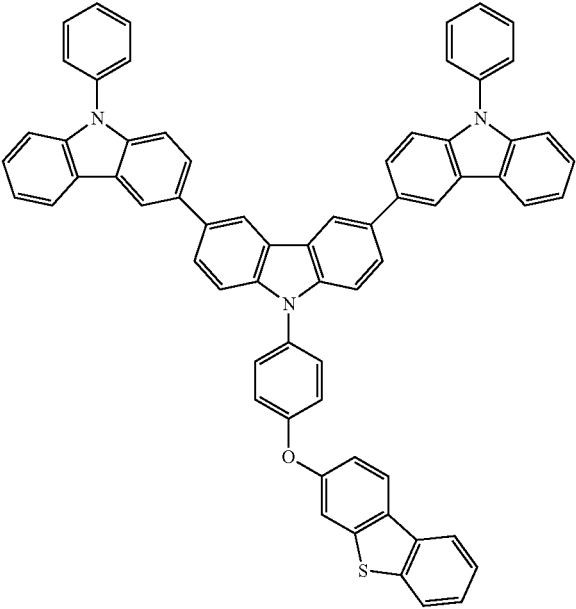
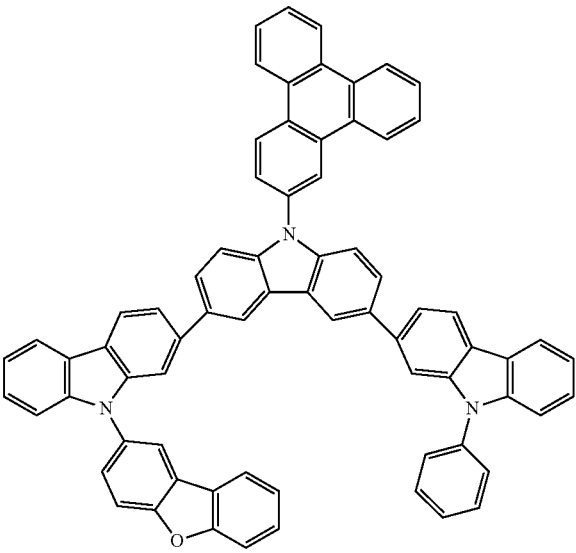

37
-continued
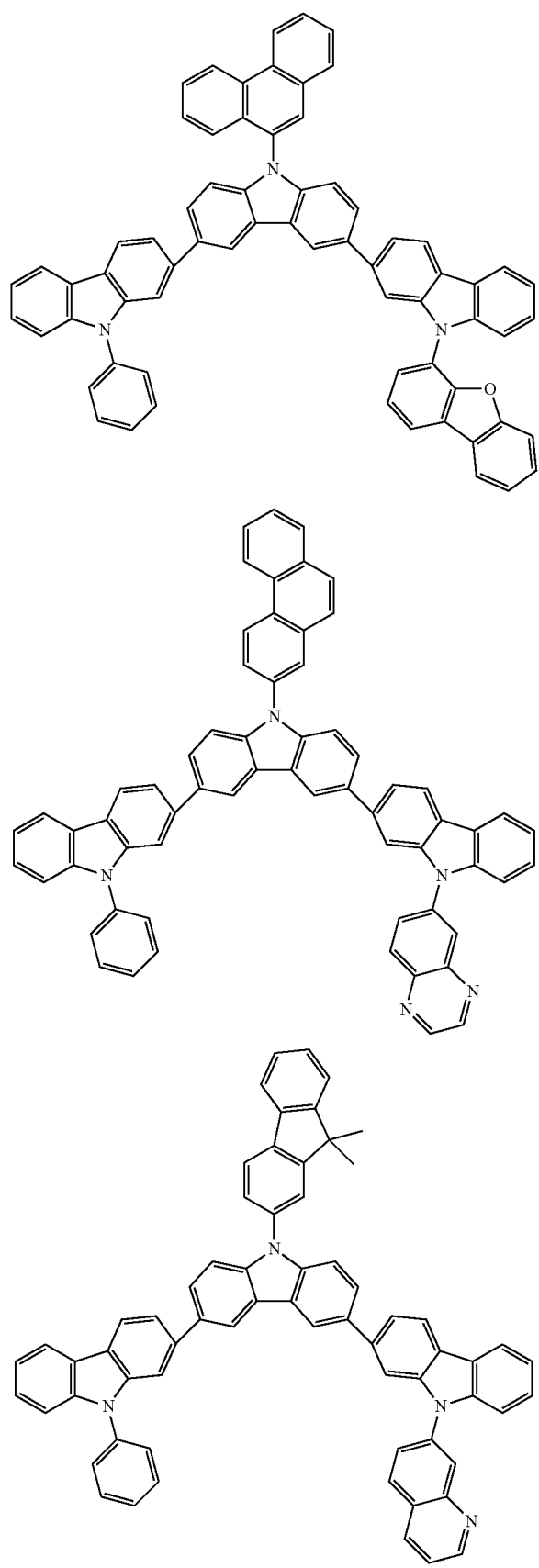
38
-continued
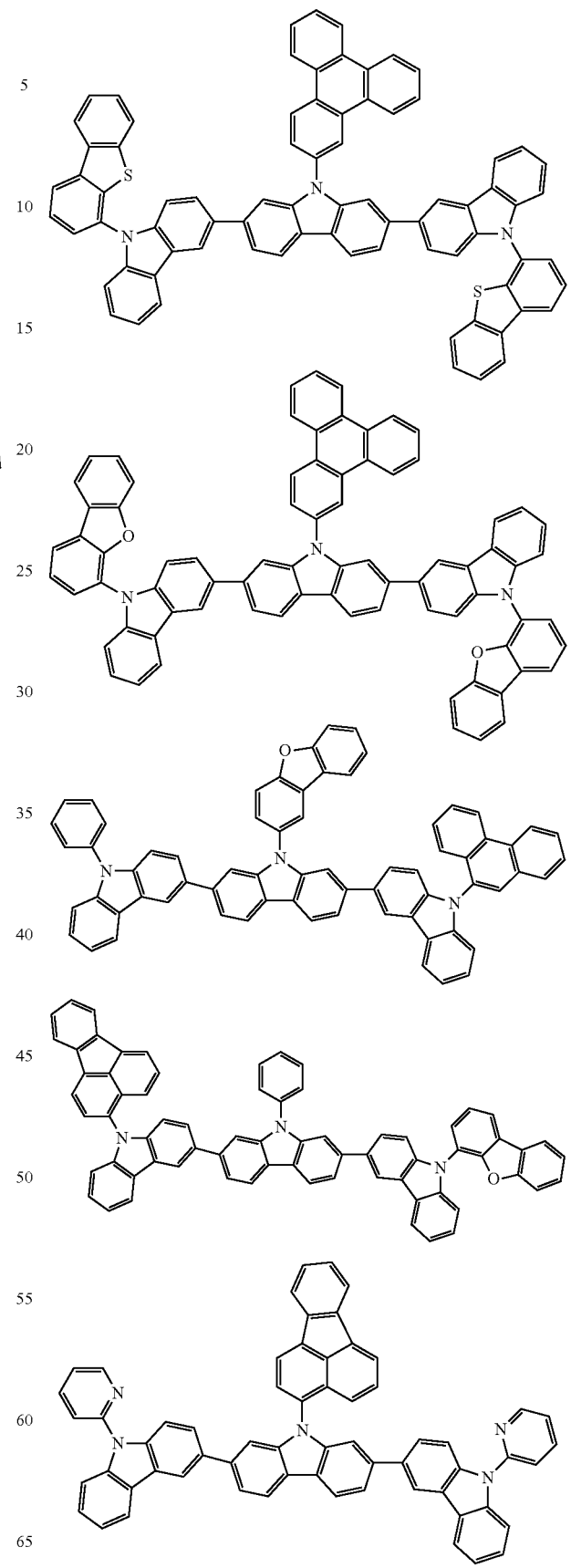

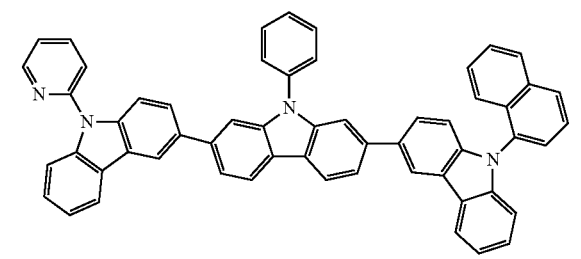
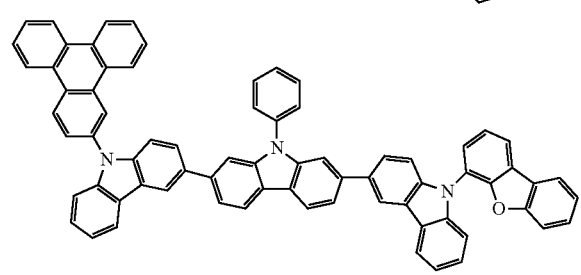
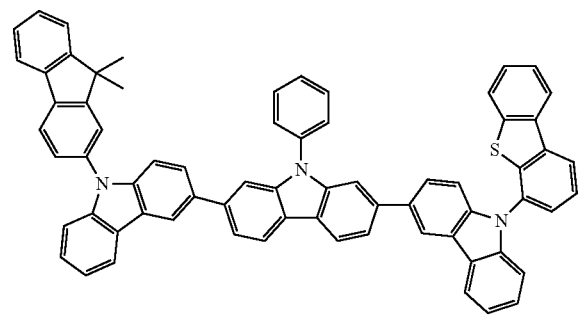
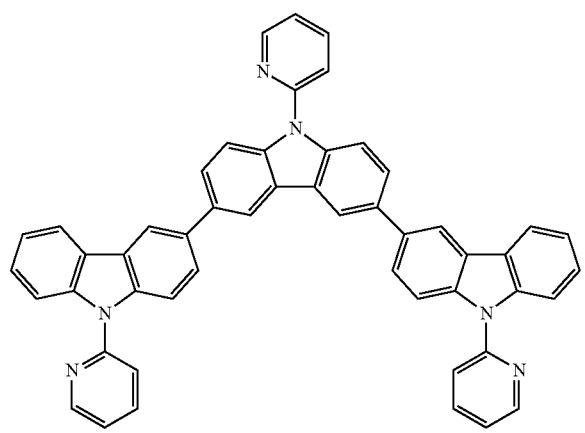
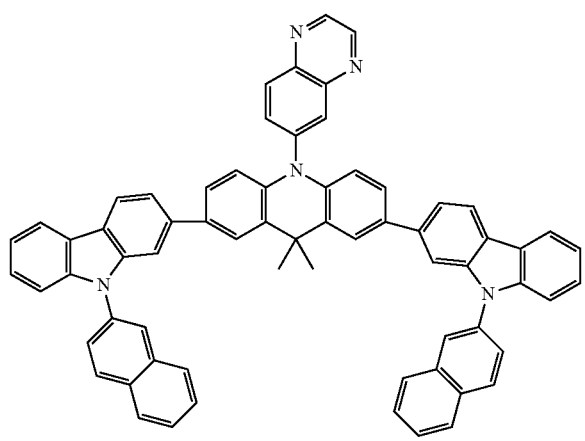
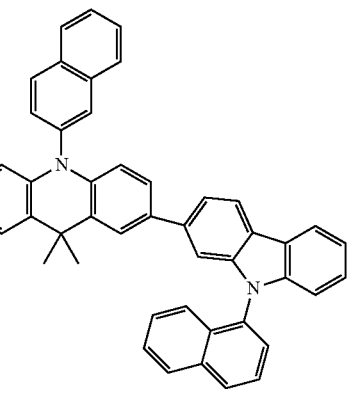

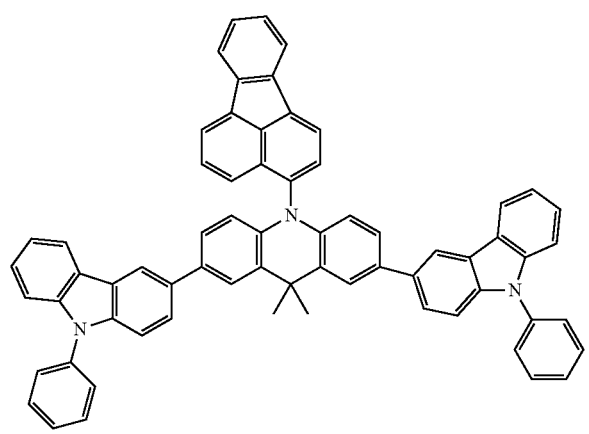
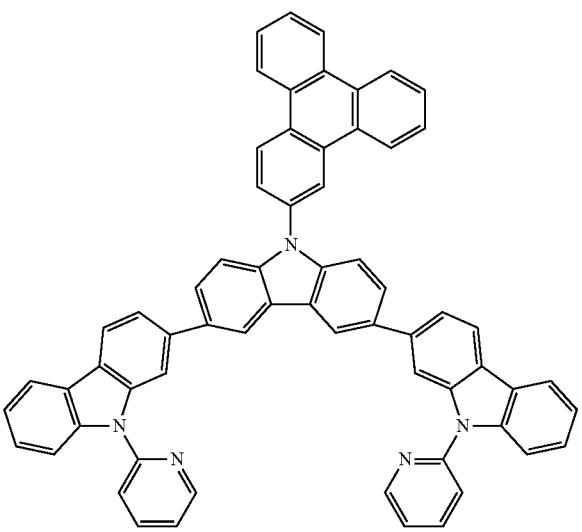
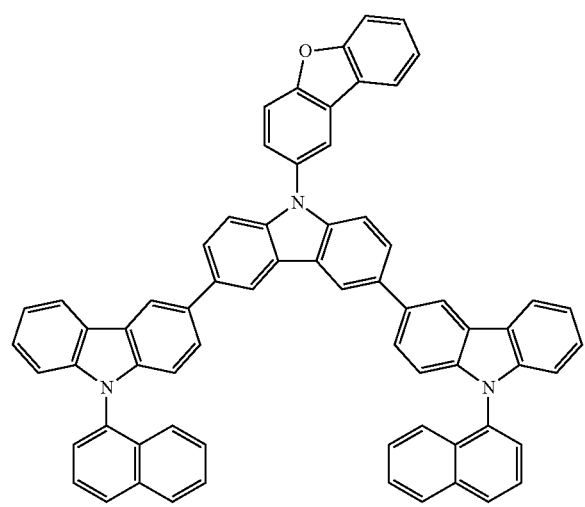
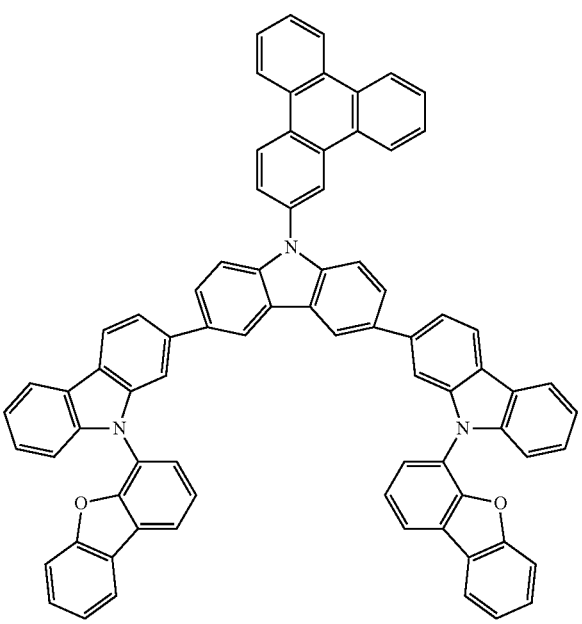
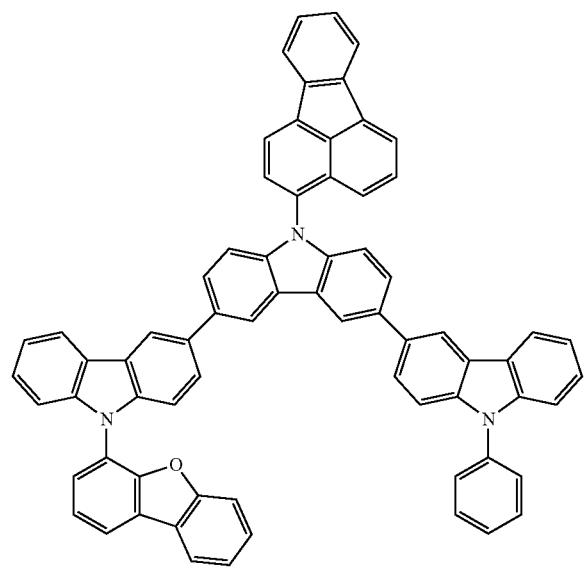
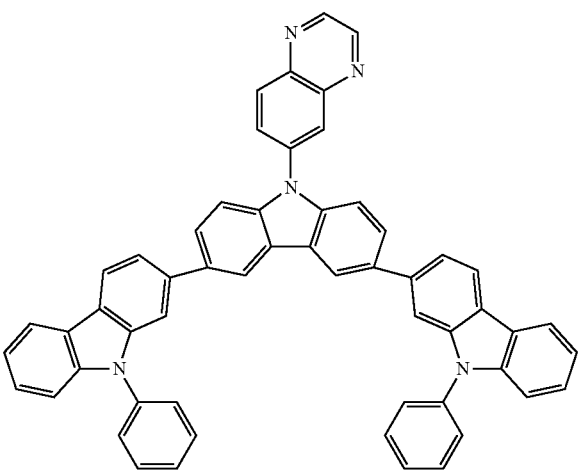

-continued
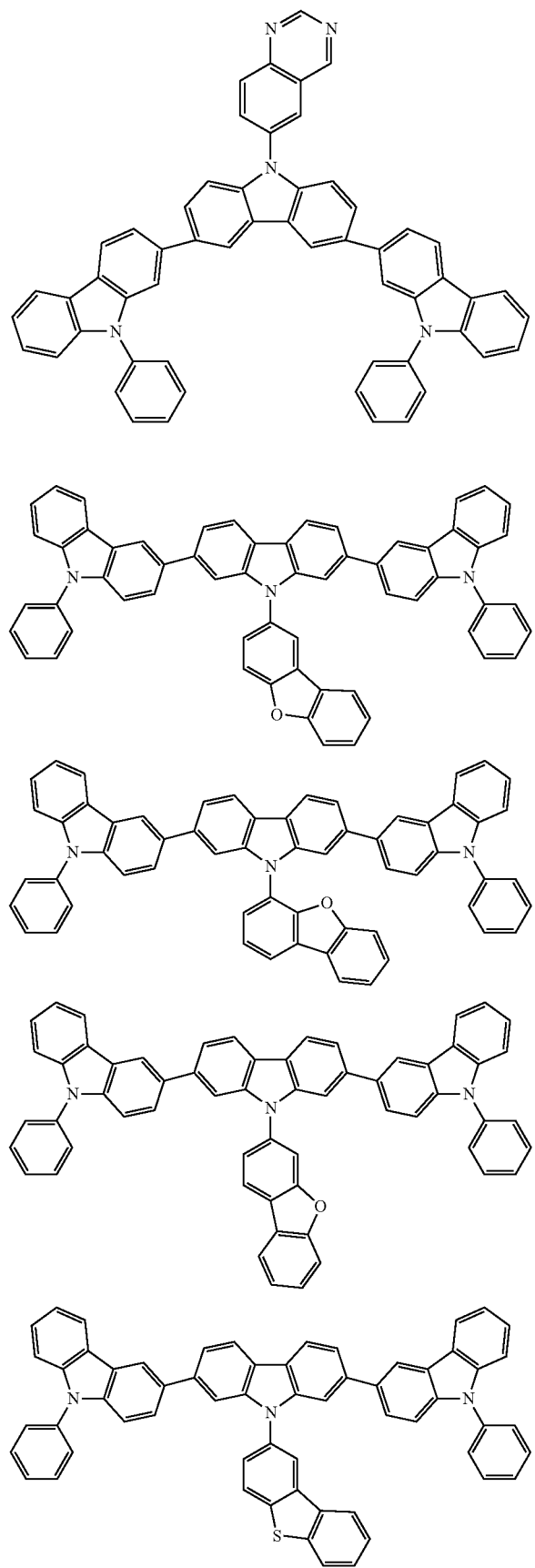
-continued
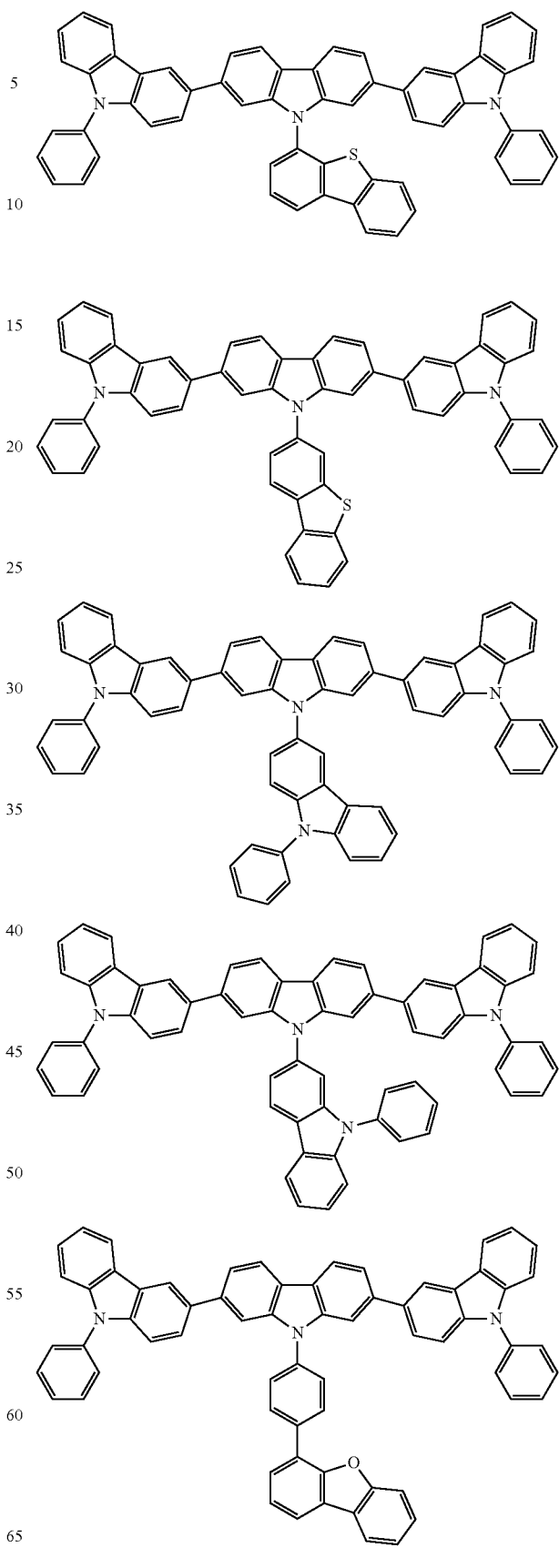

-continued
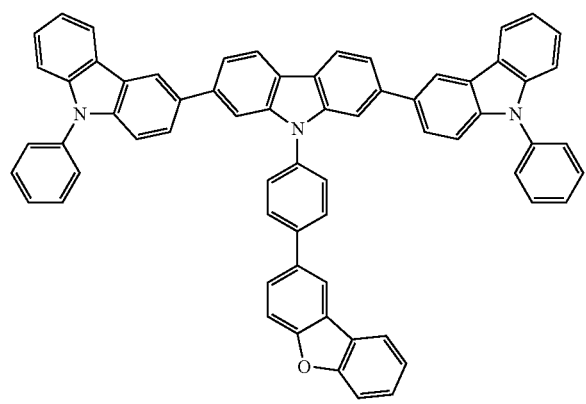
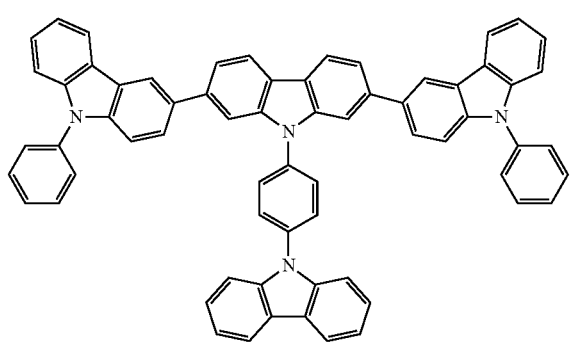
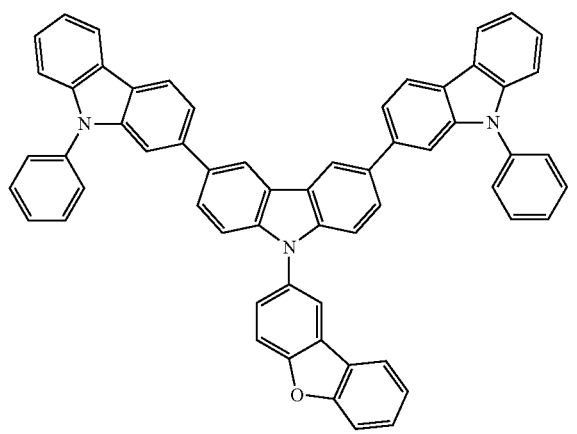
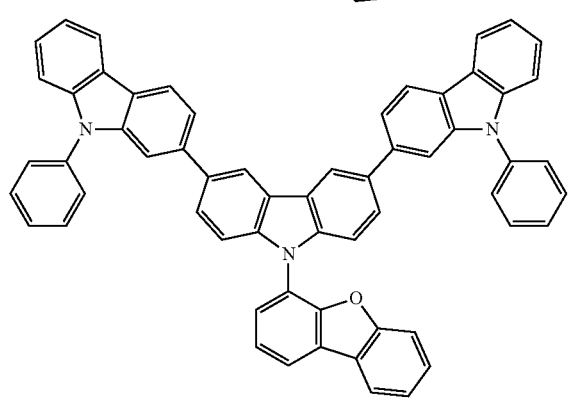
-continued
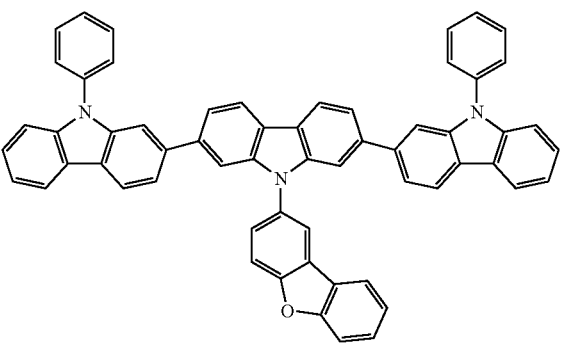
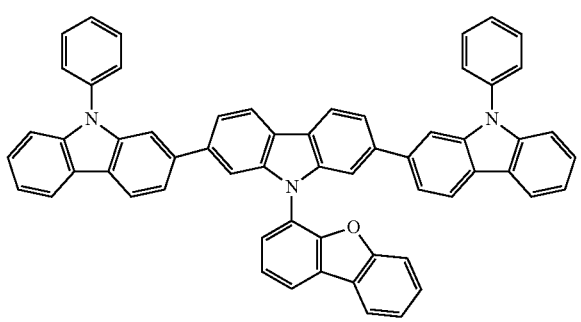
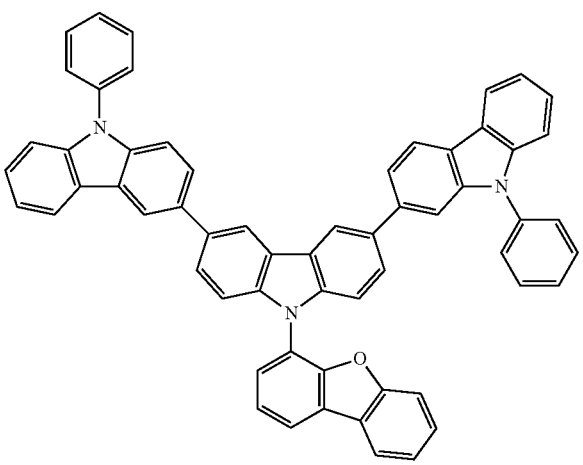
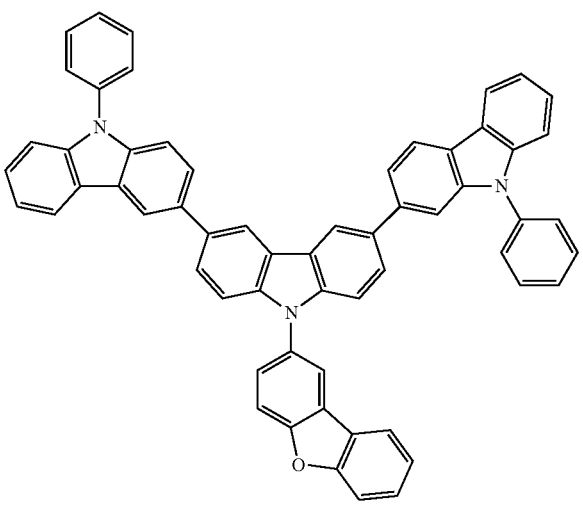

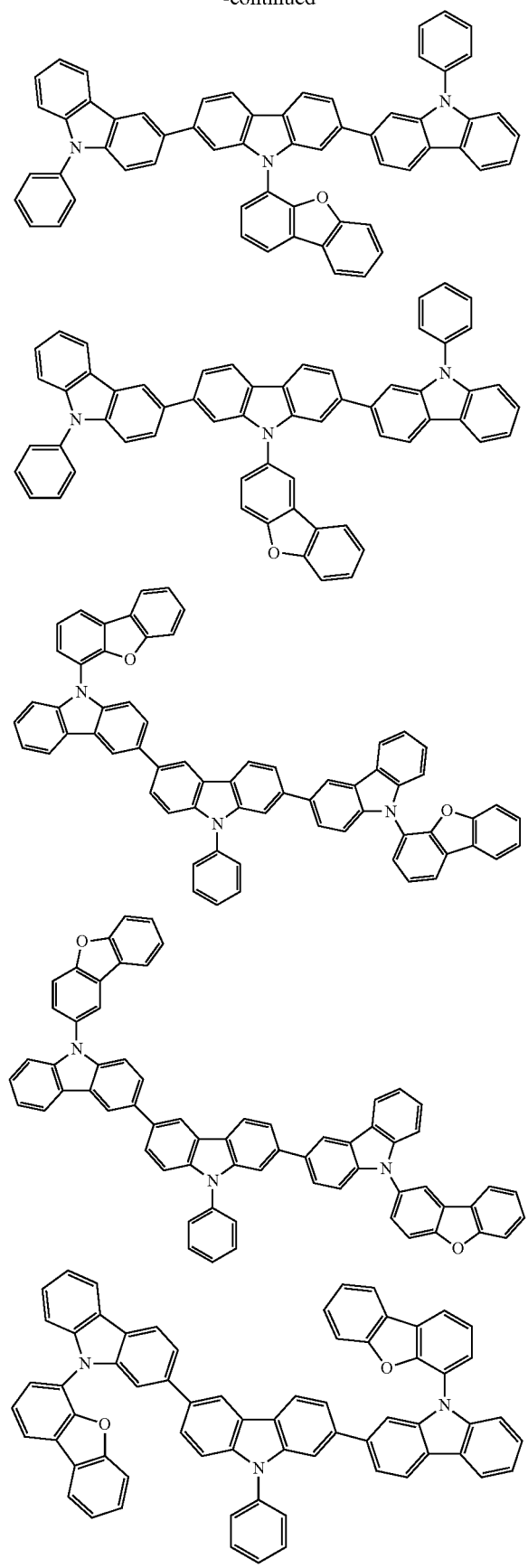
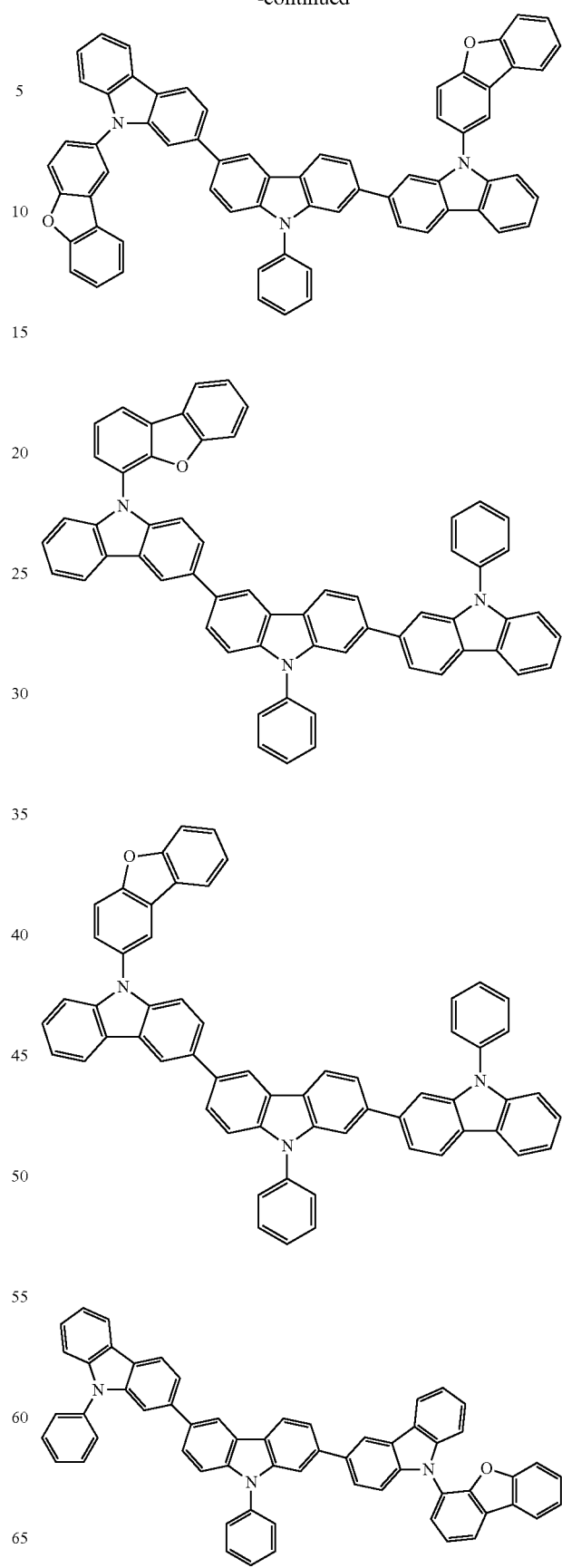

49
-continued
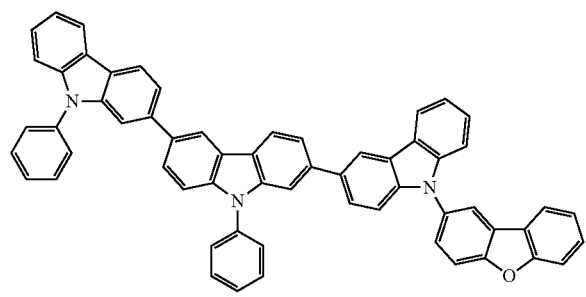
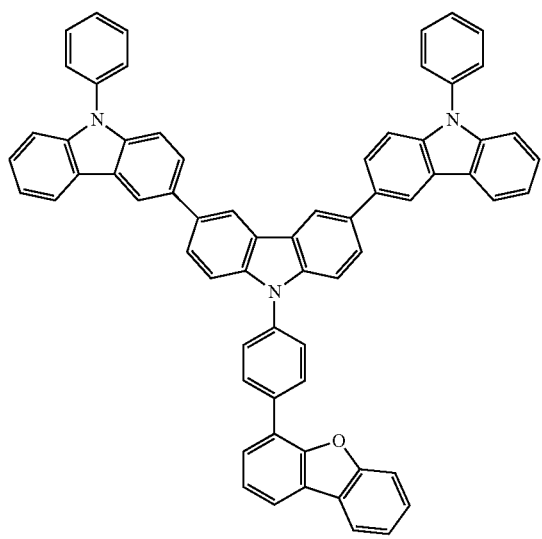
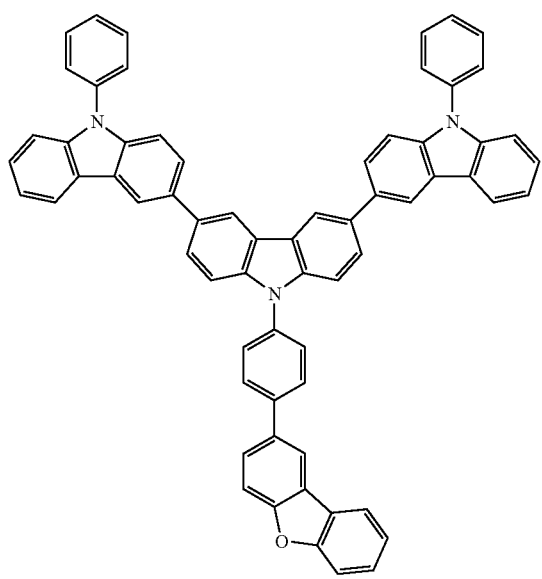
50
-continued
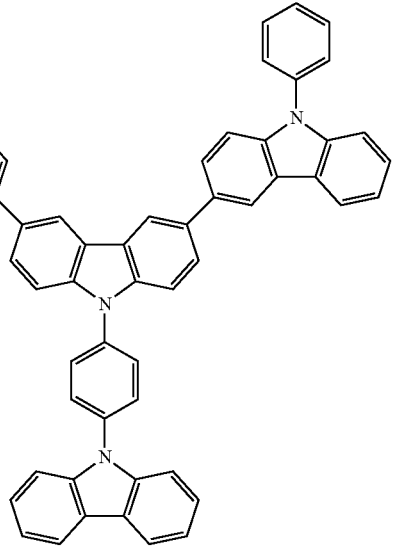
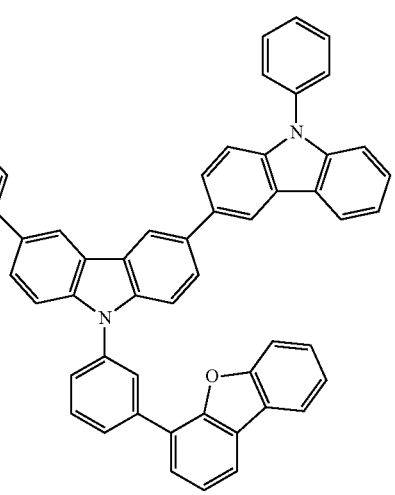
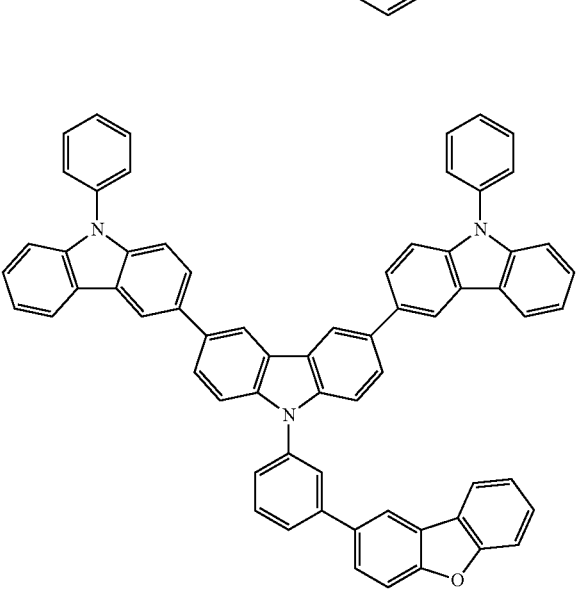

51 52
-continued -continued
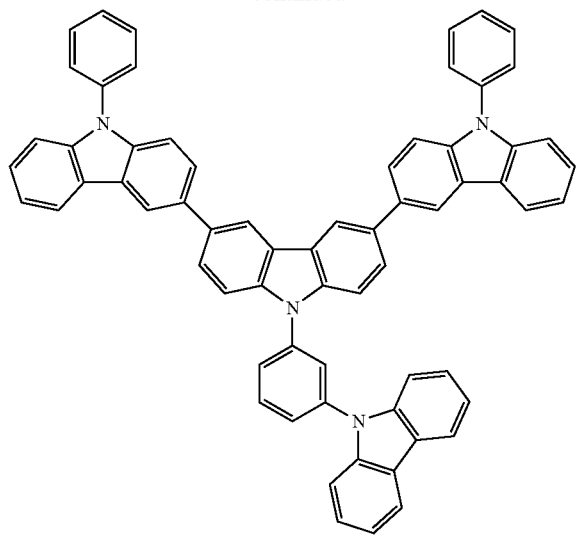
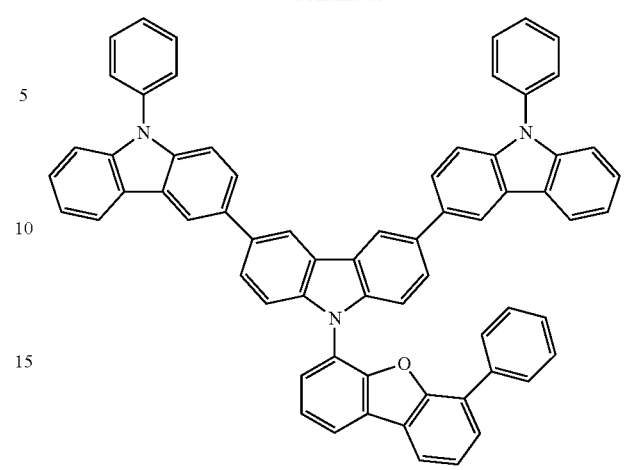
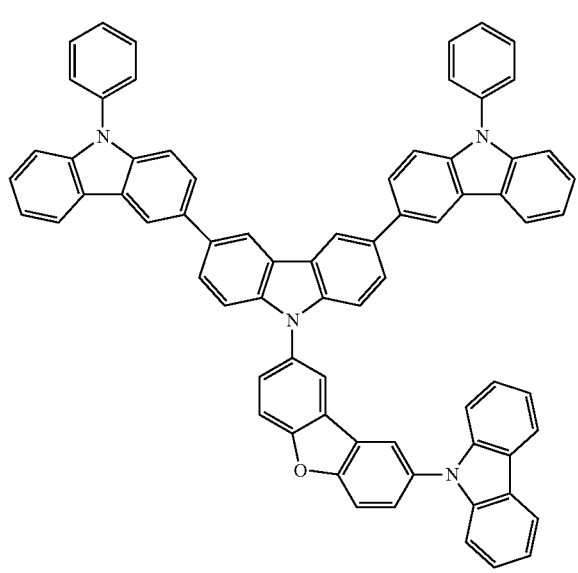
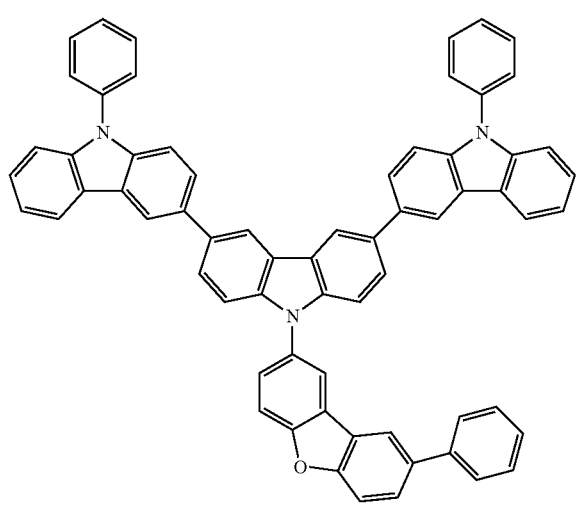
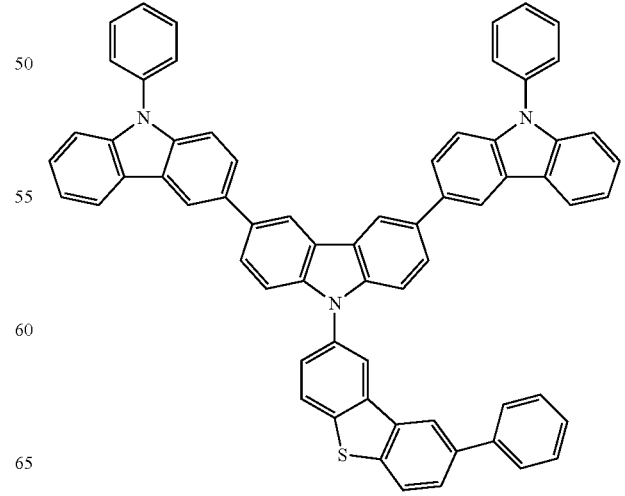

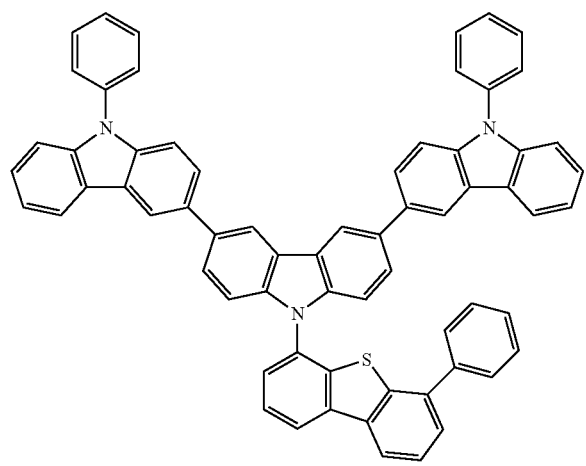
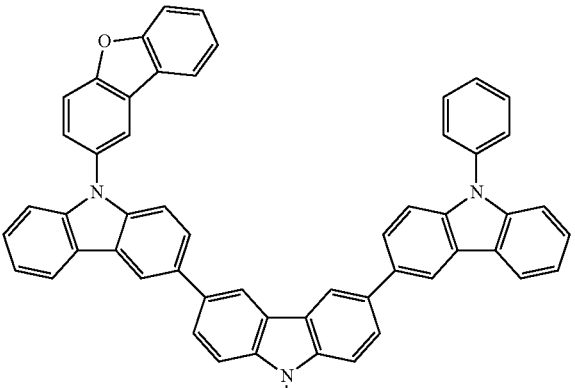
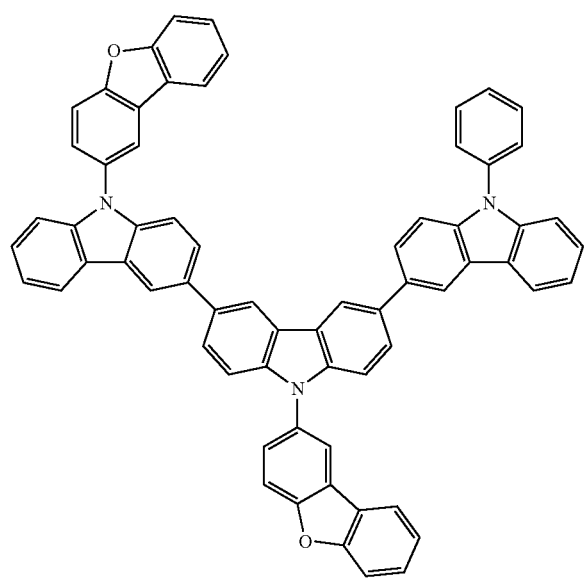
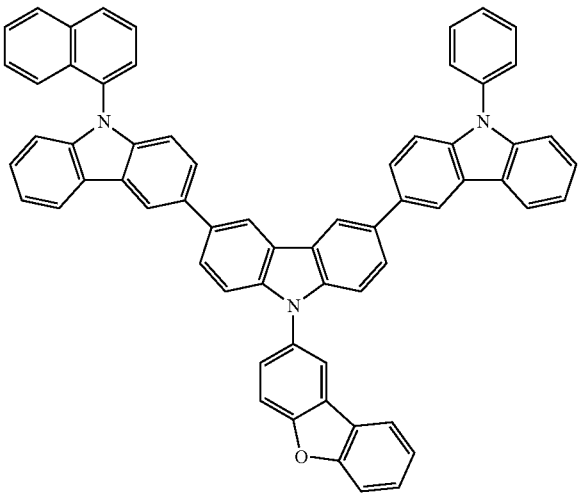
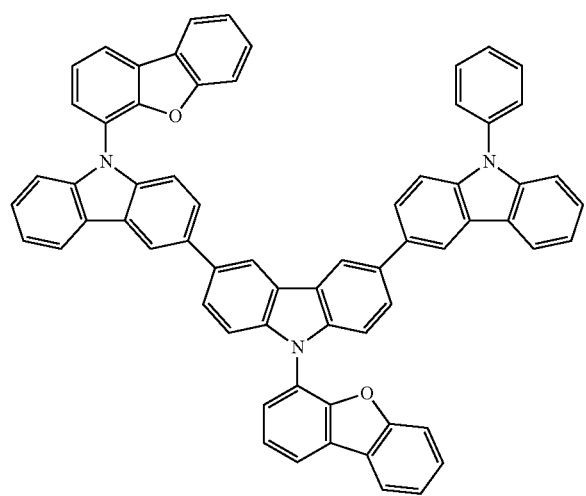
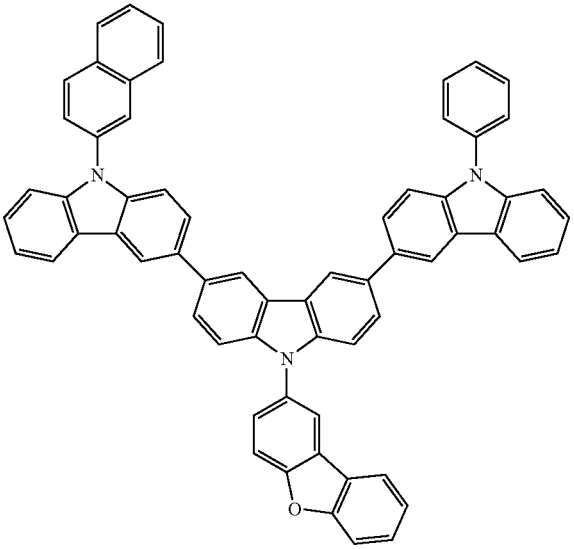

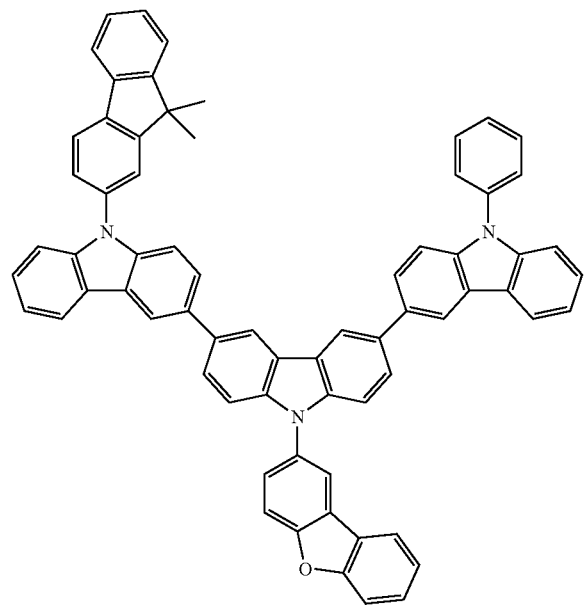
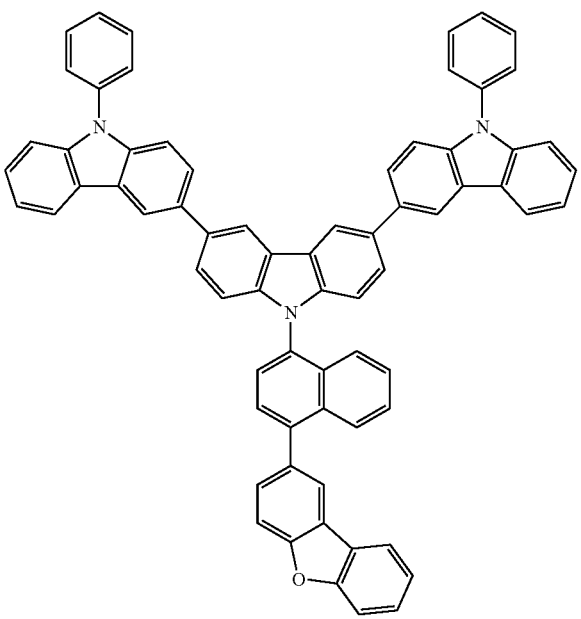
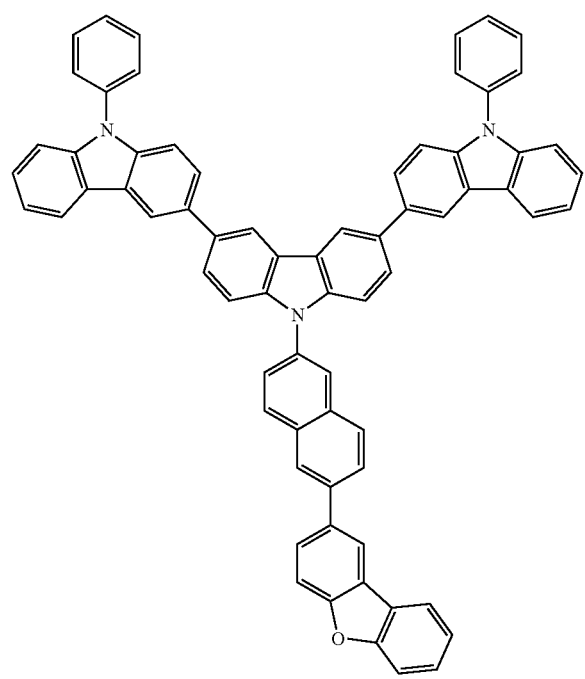
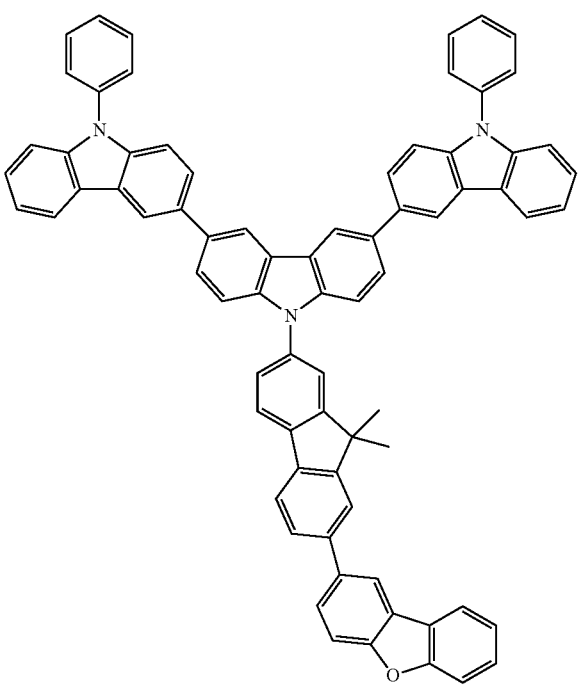

57
-continued
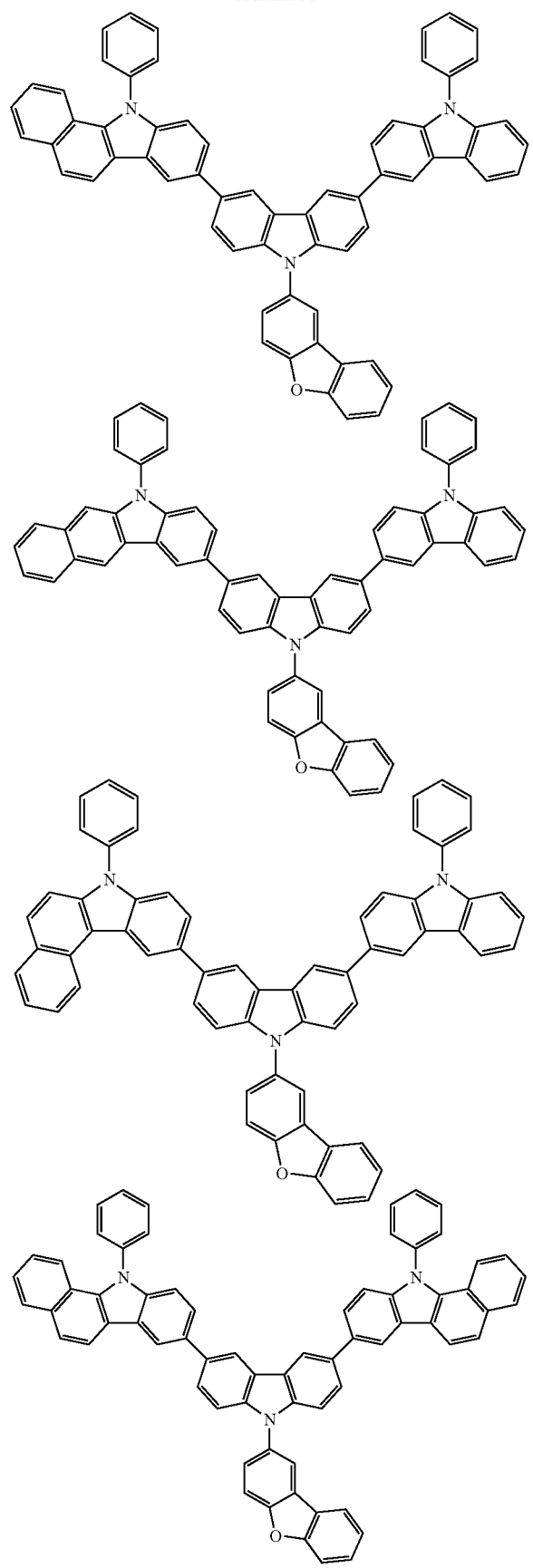
58
-continued
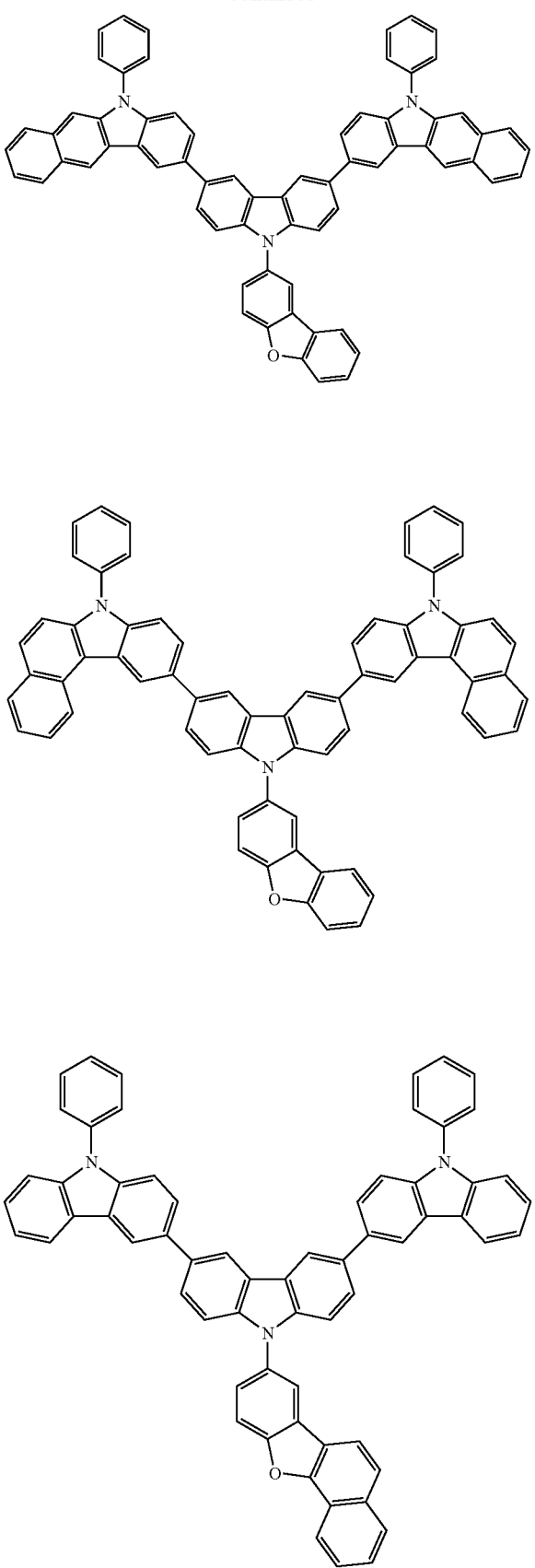

59
-continued
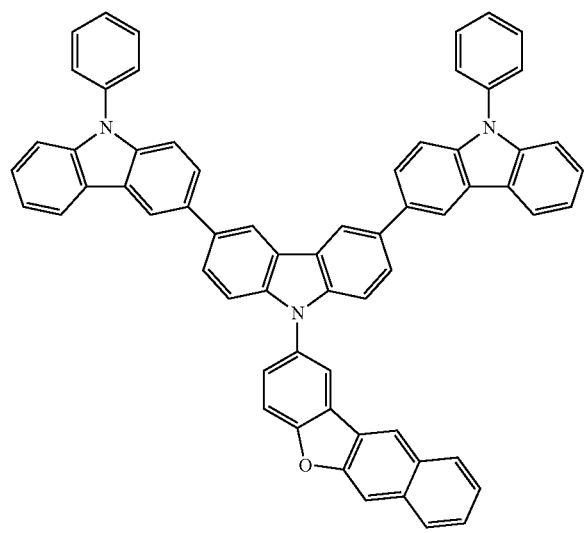
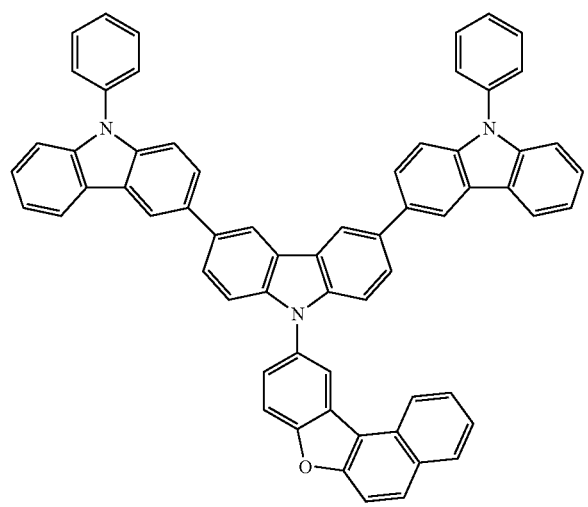
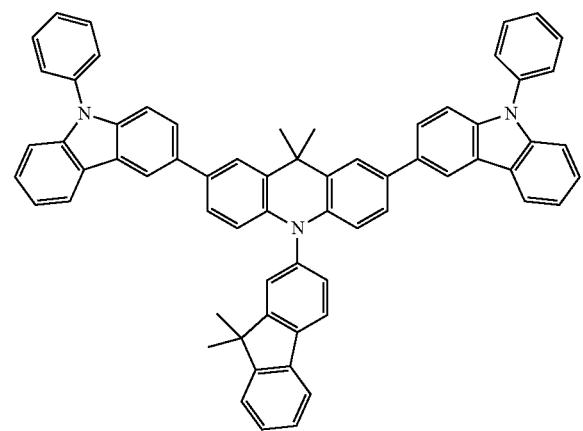
60
-continued
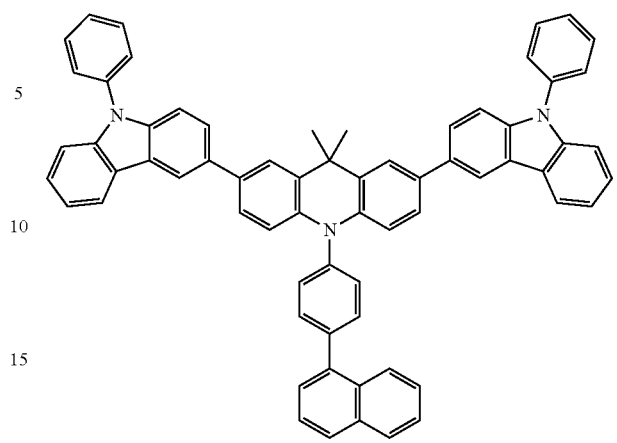
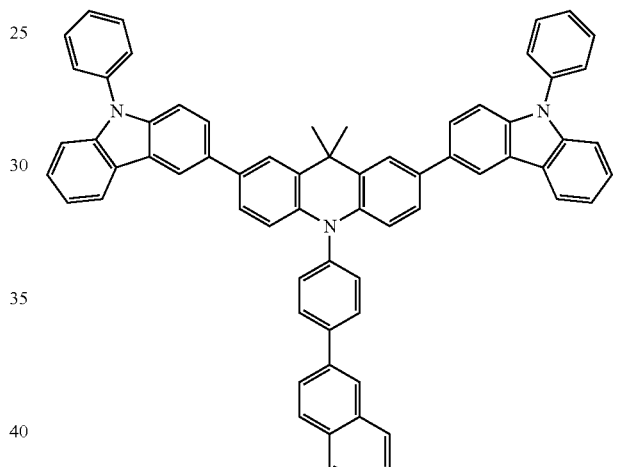
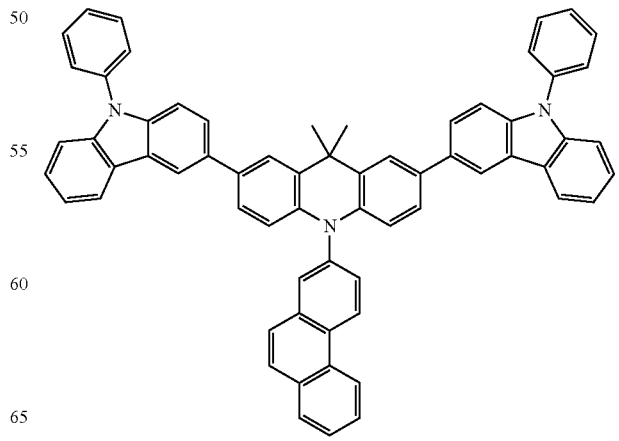

61
-continued
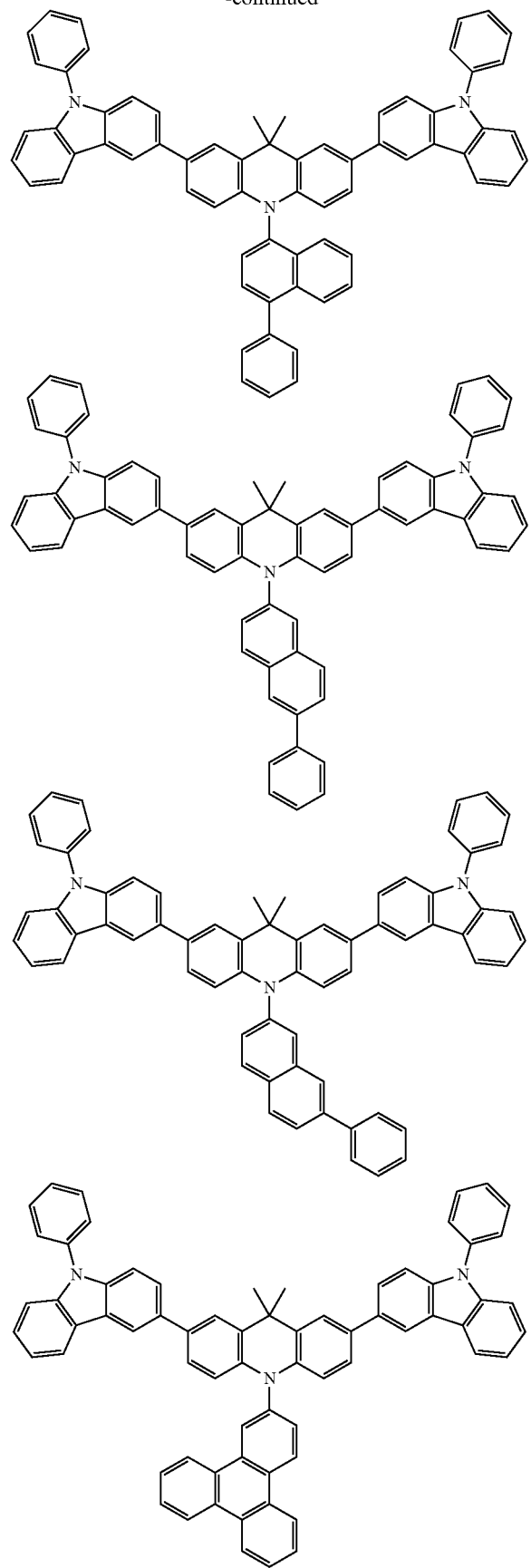
62
-continued
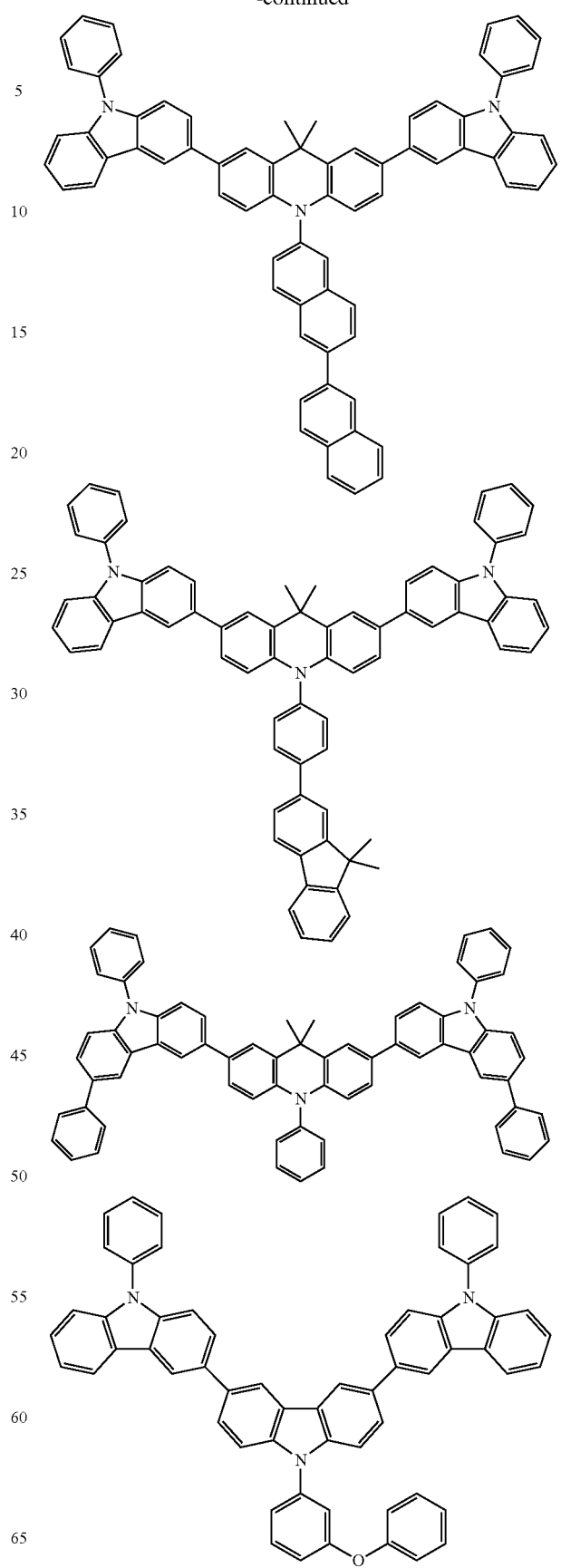

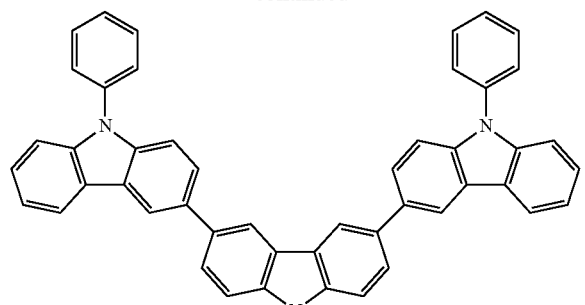
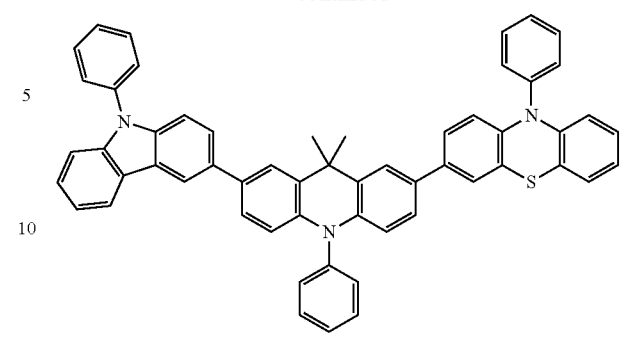
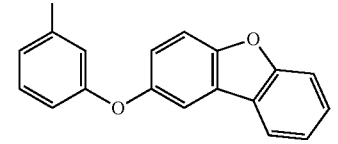
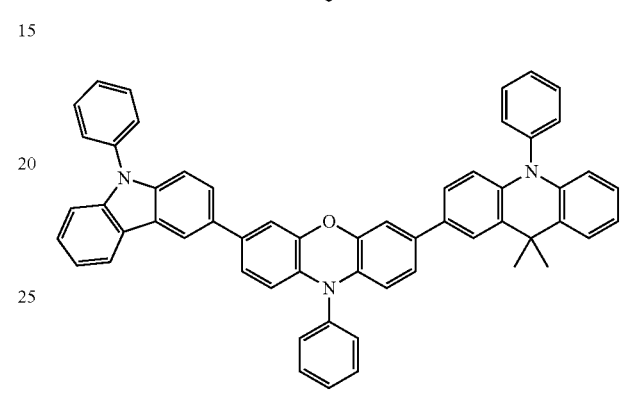
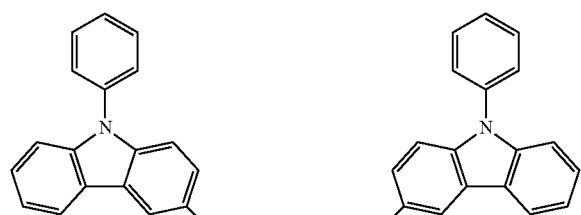
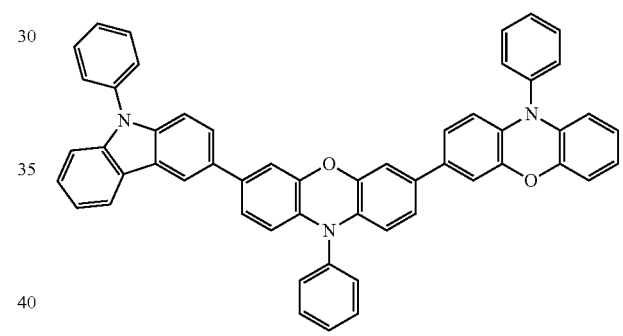
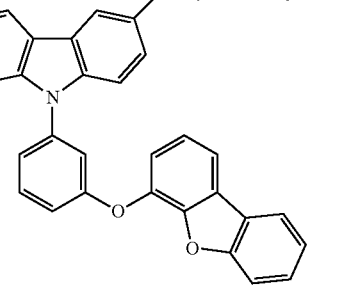
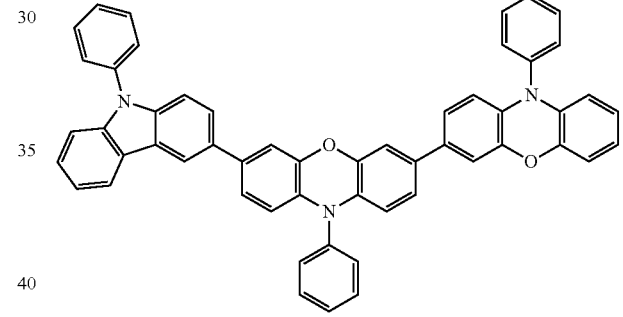
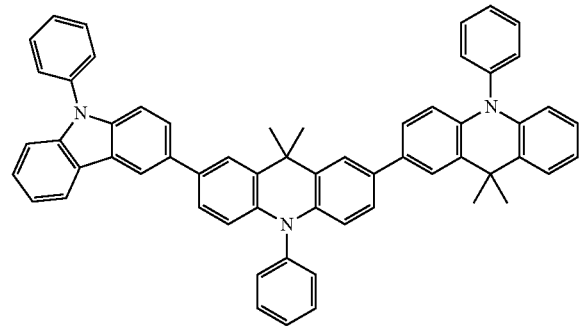
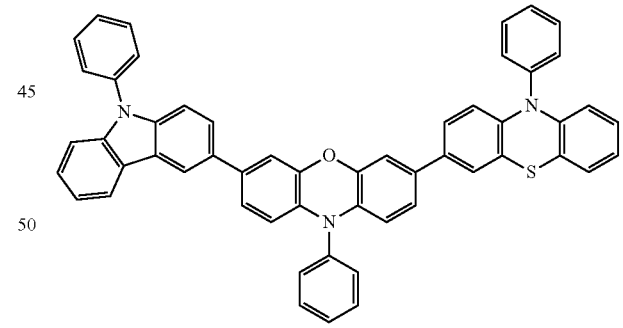
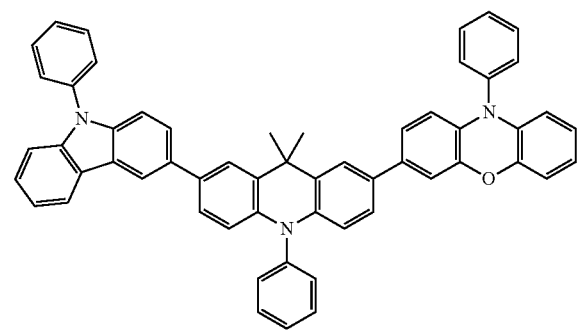
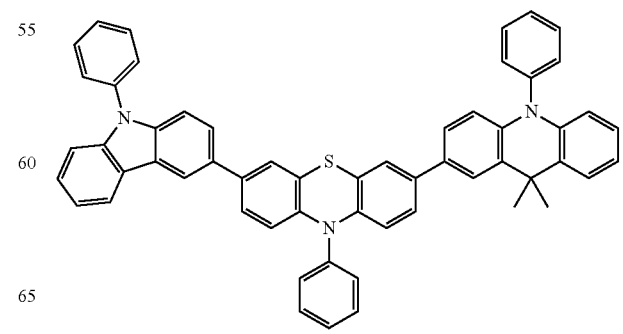

65
-continued
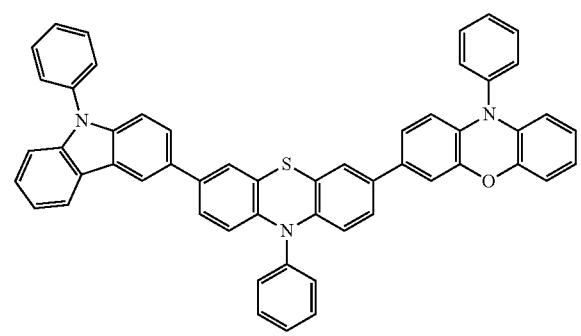
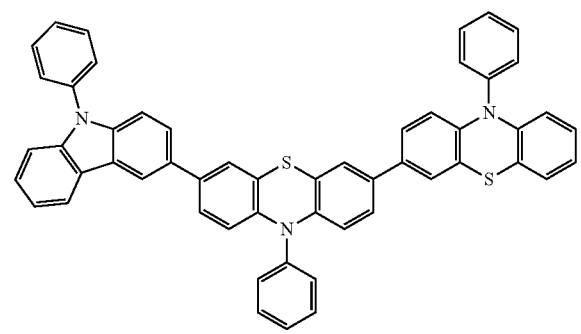
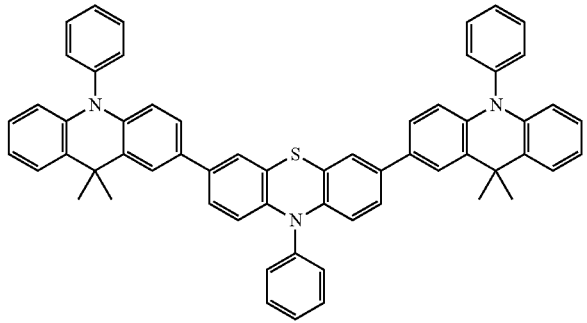
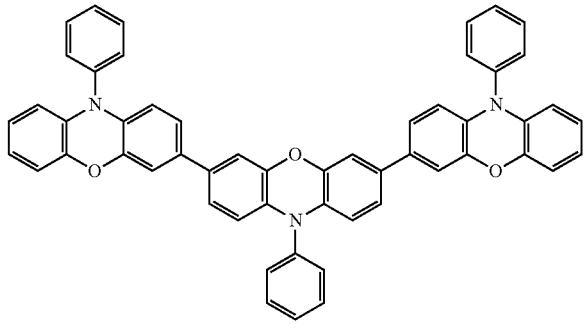
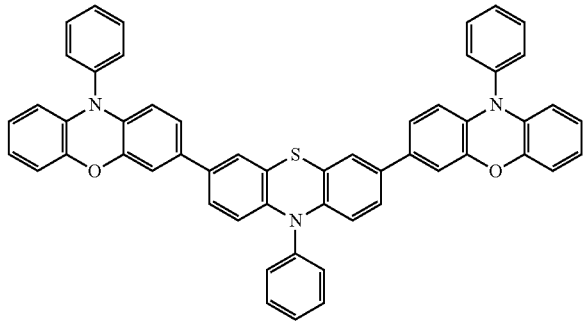
66
-continued
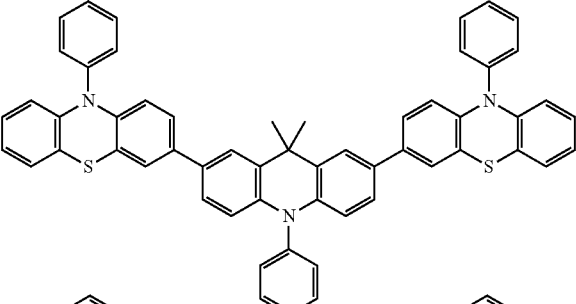
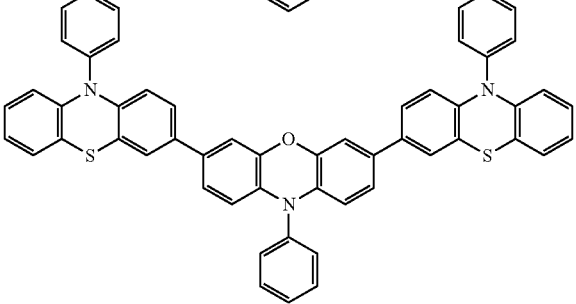
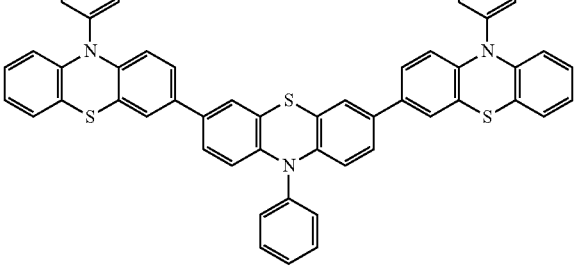
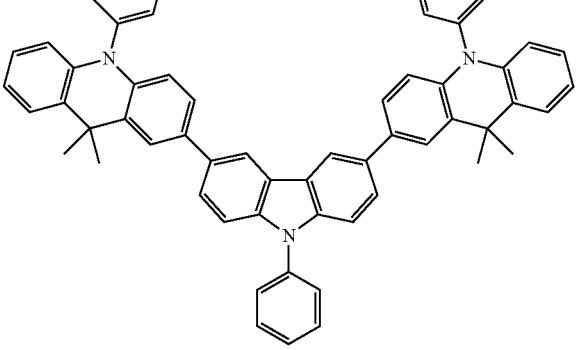
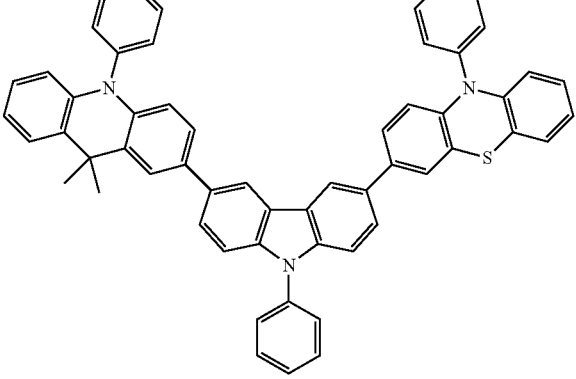

67
-continued
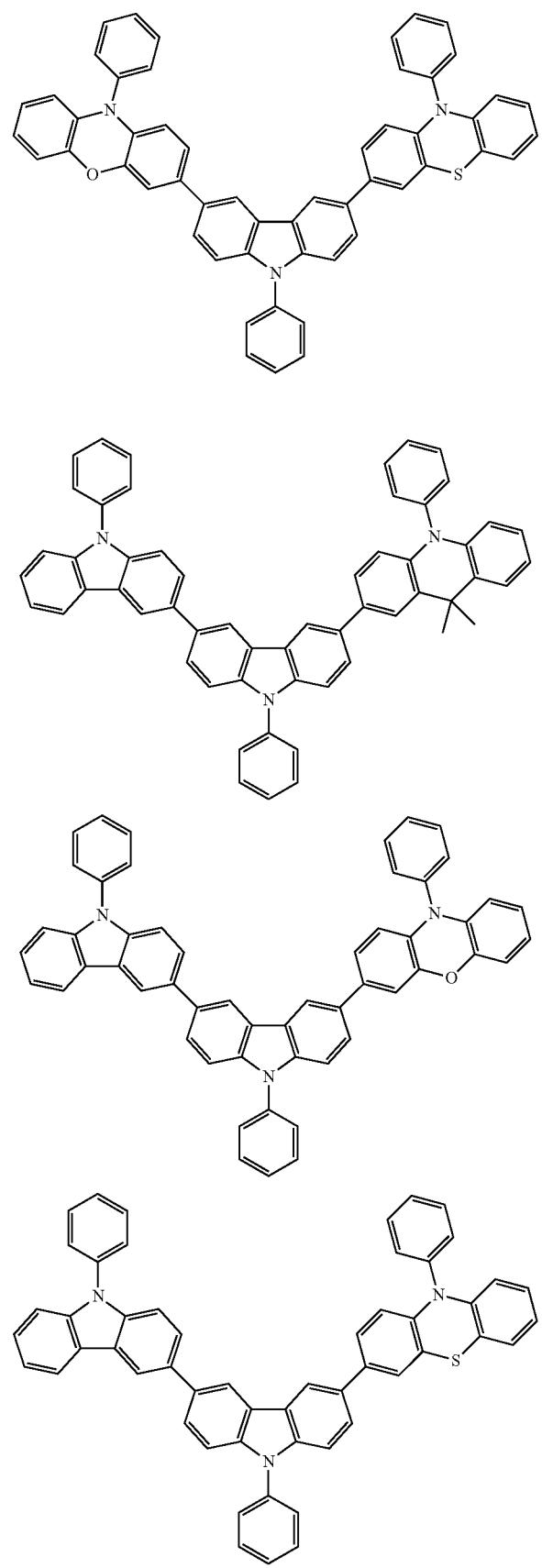
68
-continued
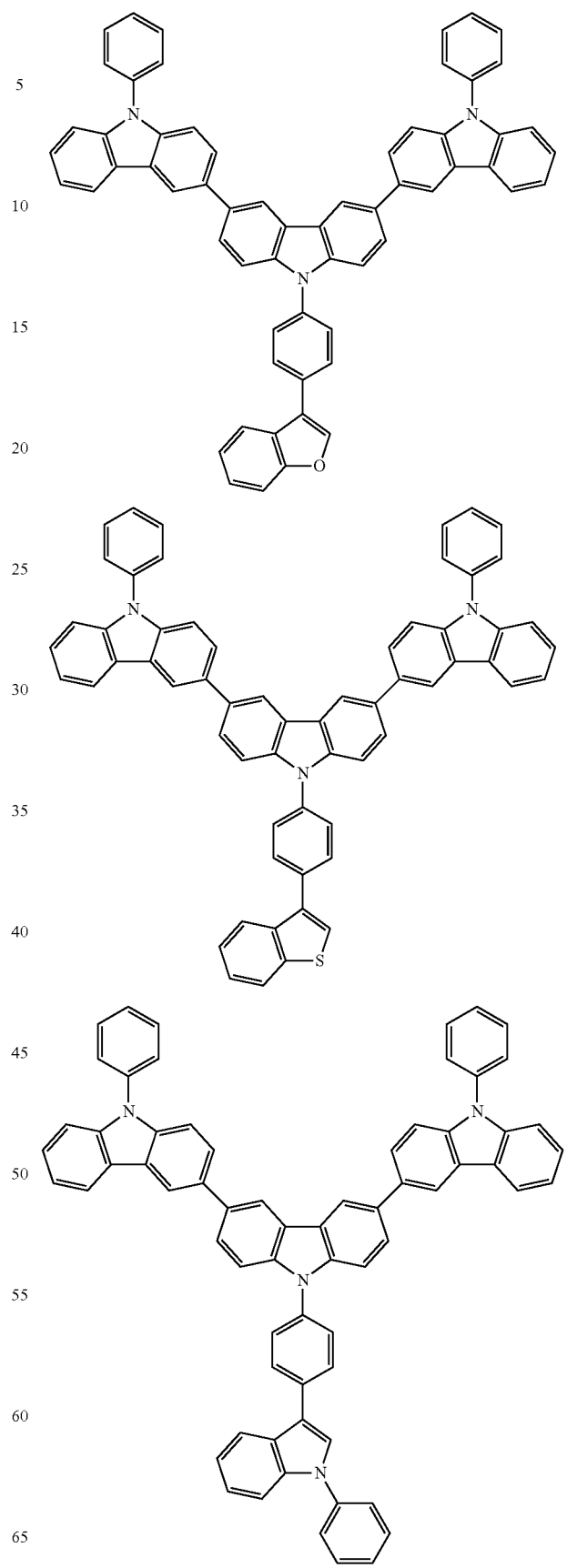

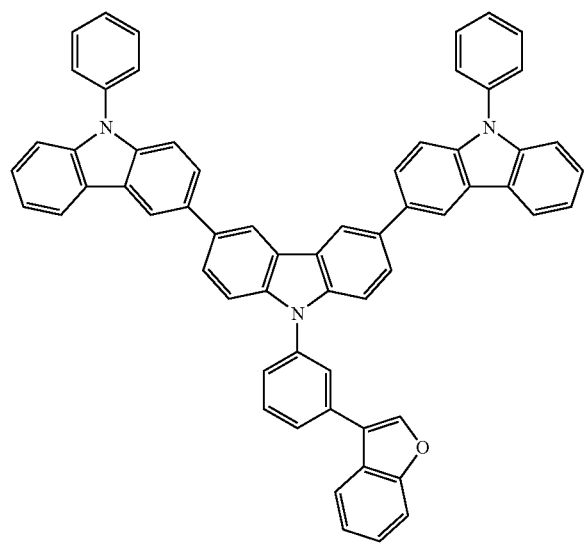
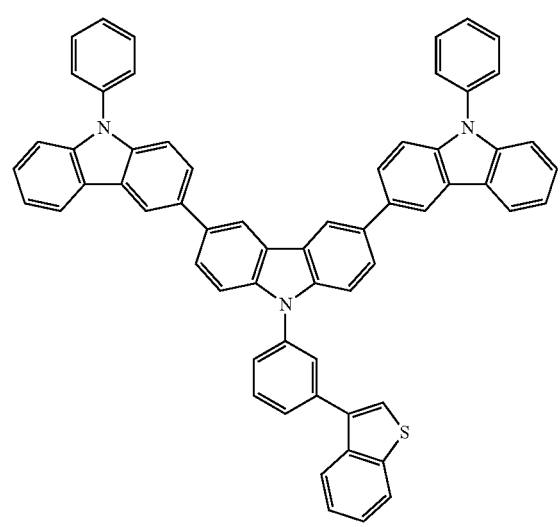
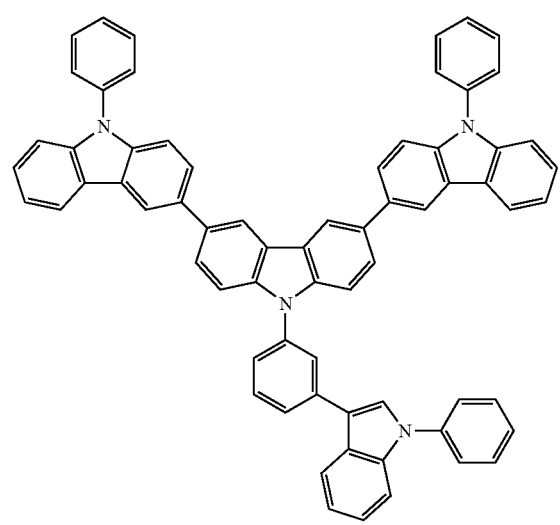
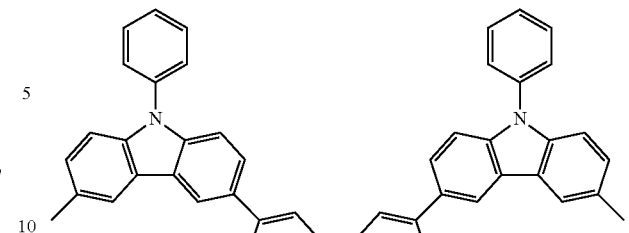
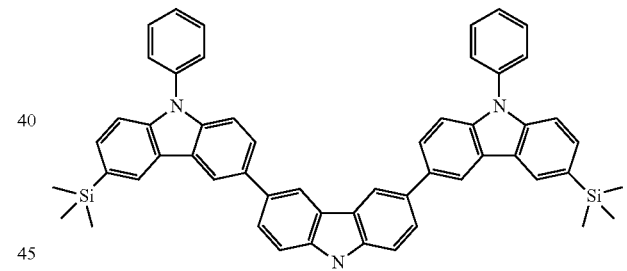
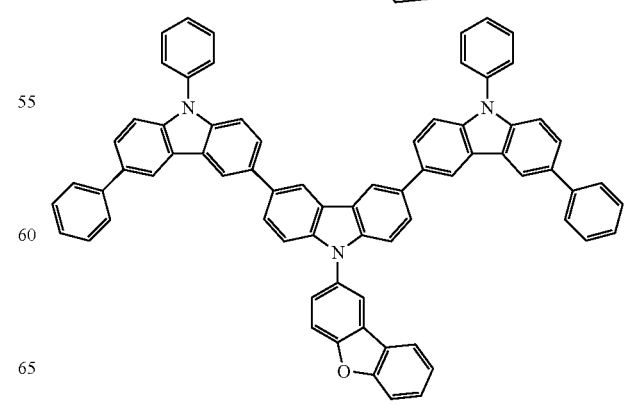

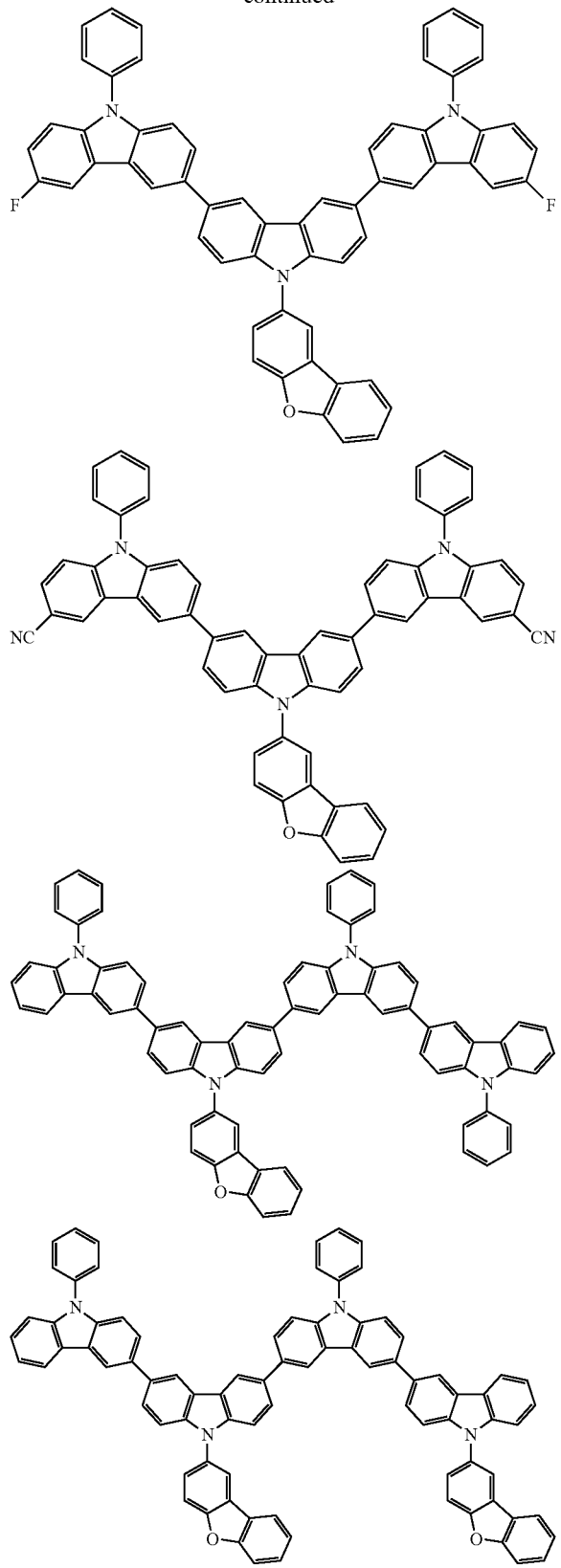

The nitrogen-containing aromatic heterocyclic derivative of the invention can be used as a material for an organic EL device, and preferably as a hole-transporting material.

The organic EL device of the invention comprises one or more organic thin film layers comprising at least an emitting layer between an anode and a cathode, and at least one layer of the organic thin film layers contains the above-mentioned nitrogen-containing aromatic heterocyclic derivative. The emitting layer preferably contains a phosphorescent emitting material.

The organic EL device of the invention is not particularly limited as long as it comprises an anode, one or more organic thin film layers, and a cathode in sequence. The organic thin film layer comprises an emitting layer, and may further comprise one or more other organic layers. In addition, the organic EL device may also comprise one or more inorganic layers.

The organic thin film layer preferably comprises a hole-transporting layer and/or a hole-injecting layer, and the nitrogen-containing aromatic heterocyclic derivative is contained in at least one of the hole-transporting layer and the hole-injecting layer. The hole-transporting layer and/or the hole-injecting layer may be constituted to contain the nitrogen-containing aromatic heterocyclic derivative as a main component, or may be constituted by the nitrogen-containing aromatic heterocyclic derivative only.

In addition, the emitting layer may comprise the nitrogen-containing aromatic heterocyclic derivative of the invention as a host material.

As the device structure of the organic EL device, the following first to third embodiments can be exemplified. In these embodiments, the emitting layer may be a stack of plural emitting layers. In addition, a hole-transporting zone is preferably provided between the anode and the emitting layer.

First Embodiment

The organic EL device of this embodiment has a device structure having at least one emitting layer. Specific examples of the structure are provided as follows.

(1) anode/emitting layer/electron-injecting and/or -transporting layer/cathode (2) anode/hole-injecting and/or -transporting layer/emitting layer/electron-injecting and/or -transporting layer/cathode (3) anode/hole-injecting layer/hole-transporting layer/emitting layer/electron-injecting and/or -transporting layer/cathode In this specification, "hole-injecting and/or -transporting layer" means one or both of the hole-injecting layer and the hole-transporting layer, and "electron-injecting and/or -transporting layer" means one or both of the electron-injecting layer and the electron-transporting layer.

Second Embodiment

The organic EL device of this embodiment has a tandem device structure having at least two emitting layers (two units each comprising an emitting layer).

A charge-generating layer (also referred to as CGL) may be provided between the two emitting layers, and an electron-transporting zone may be provided for each of the units.

Specific examples of the tandem device structure are provided as follows.

anode/hole-injecting and/or -transporting layer/fluorescent emitting layer/charge-generating layer/fluorescent emitting layer/electron-injecting and/or -transporting layer/cathode anode/hole-injecting and/or -transporting layer/fluorescent emitting layer/electron-injecting and/or -transporting layer/charge-generating layer/fluorescent emitting layer/cathode anode/hole-injecting and/or -transporting layer/fluorescent emitting layer/electron-injecting and/or -transporting layer/charge-generating layer/fluorescent emitting layer/blocking layer/cathode anode/hole-injecting and/or -transporting layer/phosphorescent emitting layer/charge-generating layer/fluorescent emitting layer/electron-injecting and/or -transporting layer/cathode anode/hole-injecting and/or -transporting layer/fluorescent emitting layer/electron-injecting and/or -transporting layer/charge-generating layer/phosphorescent emitting layer/cathode Third Embodiment The organic EL device of this embodiment comprises plural emitting layers and a charge-blocking layer between any two of the plural emitting layers.

As a preferable structure of the organic EL device of the third embodiment, such a structure as described in Japanese Patent Publication No. 4134280 B, US 2007/0273270 A1, and WO 2008/023623 A1 can be given wherein an anode, a first emitting layer, a charge-blocking layer, a second emitting layer and a cathode are stacked in sequence, and an electron-transporting zone which has a blocking layer for preventing diffusion of a triplet exciton is provided between the second emitting layer and the cathode. The charge-blocking layer is to adjust a carrier balance of the injected electron and hole in the emitting layer by providing the energy barriers of HOMO and LUMO levels between the charge-blocking layer and the adjacent emitting layer thereby to adjust the injection of a carrier into the emitting layer.

Specific examples of the structure are provided as follows.

anode/hole-injecting and/or -transporting layer/first emitting layer/charge-blocking layer/second emitting layer/electron-injecting and/or -transporting layer/cathode anode/hole-injecting and/or -transporting layer/first emitting layer/charge-blocking layer/second emitting layer/third emitting layer/electron-injecting and/or -transporting layer/cathode The hole-injecting layer or the hole-transporting layer which is in contact with the anode preferably contains an acceptor material. Further, it is preferable that the hole-transporting layer and/or the hole-injecting layer containing the nitrogen-containing aromatic heterocyclic derivative of the invention be in contact with the layer containing the compound represented by the following formula (10).

With such a structure, low-voltage driving and highly efficient emission can be attained by the effects described in the patents identified below.

As the acceptor material, in addition to hexaazatriphenylene derivative and the like described in Japanese Patent Publication Nos. 3614405 B, 3571977 B, or U.S. Pat. No. 4,780,536 B, inorganic compounds such as p-type Si, p-type SiC and the like; electron-accepting inorganic oxides such as molybdenum oxide and the like; electron-accepting organic compounds such as TCNQ derivative and the like can also be preferably used.

As the acceptor material, the compound represented by the following formula (10) or (11) is preferably used.

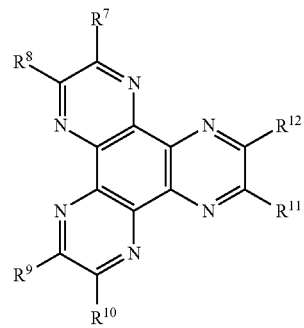

(10)

In the above formula (10), $R^7$ to $R^{12}$ are independently a cyano group, —$CONH_2$, a carboxy group, or —$COOR^{13}$ wherein $R^{13}$ is an alkyl group having 1 to 20 carbon atoms, or $R^7$ and $R^8$, $R^9$ and $R^{10}$, or $R^{11}$ and $R^{12}$ are bonded each other to form —CO—O—CO—.

As the above alkyl group, a straight chain, branched, or cyclic alkyl group can be given, and preferably an alkyl group having 1 to 12 carbon atoms, more preferably an alkyl group having 1 to 8 carbon atoms can be given. Specifically, a methyl group, an ethyl group, a n-propyl group, an isopropyl group, a n-butyl group, a sec-butyl group, a t-butyl group, a n-hexyl group, a n-octyl group, a n-decyl group, a n-hexadecyl group and the like can be given.

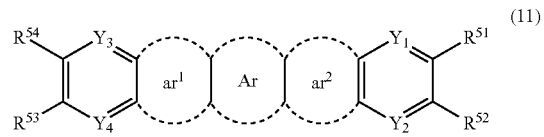

(11)

In the above formula (11), Ar is a hydrocarbon monocyclic ring or fused ring having 6 to 24 ring carbon atoms, or a heterocyclic monocyclic ring or fused ring having 6 to 24 ring atoms. $ar^1$ and $ar^2$ may be the same or different and is represented by the following formula (i) or (ii).

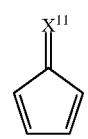

(i)

(ii)

In the above formulas, $X^{11}$ and $X^{12}$ may be the same or different, and may be a divalent group represented by the following formulas (a) to (g).

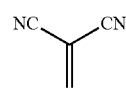

(a)

-continued

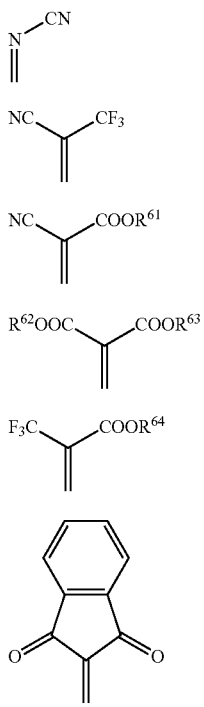

(b)

(c)

(d)

(e)

(f)

(g)

In the above formulas, $R^{61}$ to $R^{64}$ may be the same or different, and is a hydrogen atom, a substituted or unsubstituted fluoroalkyl group having 1 to 20 carbon atoms, a substituted or unsubstituted alkyl group having 1 to 20 carbon atoms, a substituted or unsubstituted aryl group having 6 to 50 carbon atoms, or a substituted or unsubstituted heterocyclic group having 3 to 50 ring atoms. $R^{62}$ and $R^{63}$ may be bonded each other to form a ring.

$R^{51}$ to $R^{54}$ in the formula (11) may be the same or different, and is a hydrogen atom, a substituted or unsubstituted alkyl group having 1 to 20 carbon atoms, a substituted or unsubstituted aryl group having 6 to 50 carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 carbon atoms, or a cyano group. Among $R^{51}$ to $R^{54}$, the adjacent two may be bonded each other to form a ring. $Y^1$ to $Y^4$ may be the same or different, and is N, CH, or $C(R^{55})$. $R^{55}$ is a substituted or unsubstituted alkyl group having 1 to 20 carbon atoms, a substituted or unsubstituted aryl group having 6 to 50 carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 carbon atoms, or a cyano group.

The organic EL device of the invention preferably contains at least one of the carbazolyl compounds represented by the following formulas (20) and (21) in at least one layer, preferably an emitting layer, of the organic thin film layers. The compounds are preferably used as a host material in the emitting layer.

$$(Cz-)_a A^3 \quad (20)$$

$$Cz(-A^3)_b \quad (21)$$

In the formulas (20) and (21), Cz is a substituted or unsubstituted arylcarbazolyl group, a substituted or unsubstituted carbazolylaryl group, or a substituted or unsubstituted carbazolylalkylene group.

$A^3$ is a group represented by the following formula (A).

a and b are independently an integer of 1 to 3.

$$(M^1)_c\text{-}(L^5)_d\text{-}(M^2)_e \quad (A)$$

In the formula (A), $M^1$ and $M^2$ are independently a substituted or unsubstituted nitrogen-containing aromatic heterocyclic ring having 3 to 40 ring atoms or a substituted or unsubstituted nitrogen-containing fused aromatic heterocyclic ring having 3 to 40 ring atoms, and may be the same or different.

$L^5$ is a single bond, a substituted or unsubstituted aromatic hydrocarbon ring group or fused aromatic hydrocarbon ring group having 6 to 30 carbon atoms, a substituted or unsubstituted cycloalkylene group having 5 to 30 carbon atoms, or a substituted or unsubstituted aromatic heterocyclic group or fused aromatic heterocyclic group having 2 to 30 carbon atoms.

c is an integer of 0 to 2, d is an integer of 1 to 2, and e is an integer of 0 to 2. c+e is 1 or more.

The compounds represented by the formulas (20) and (21) will be explained in detail below.

Cz is a substituted or unsubstituted arylcarbazolyl group, a substituted or unsubstituted carbazolylaryl group, or a substituted or unsubstituted carbazolylalkyl group.

The arylcarbazolyl group is a carbazolyl group having as a substituent at least one aryl group or heteroaryl group, and the position at which the carbazolyl group is substituted with the aryl group or heteroaryl group is not restricted.

Specifically, the following can be given, for example. In the following chemical formulas, Ar is an aryl group or a heteroaryl group, and * represents a position at which another group is connected.

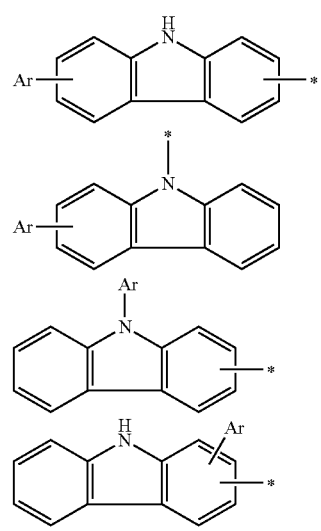

In addition, the carbazolylaryl group is an aryl group having as a substituent at least one carbazolyl group, and the position at which the aryl group is substituted with the carbazolyl group is not restricted.

Specifically, the following can be given, for example. In the following chemical formulas, Ar is an aryl group, and * represents a position at which another group is connected.

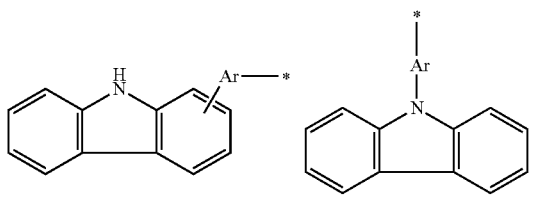

The carbazolylalkyl group is an alkyl group having as a substituent at least one carbazolyl group, and the position at which the alkyl group is substituted with the carbazolyl group is not restricted.

Specifically, in the above-mentioned carbazolylaryl group, a group in which Ar that is an aryl group is replaced with an alkyl group can be given The substituted arylcarbazolyl group is the above-mentioned arylcarbazolyl group having at least one substituent wherein the position of substitution is not restricted, and the substituted carbazolylaryl group is the above-mentioned carbazolylaryl group having at least one substituent wherein the position of substitution is not restricted.

In the formulas (20) and (21), a and b are independently an integer of 1 to 3.

The aryl group of the arylcarbazolyl group or the carbazolylaryl group has preferably 6 to 30 carbon atoms, and a phenyl group, a naphthyl group, an anthryl group, phenanthryl group, a naphthathenyl group, a pyrenyl group, a fluorenyl group, a biphenyl group, a terphenyl group and the like can be given, for example. Of these, a phenyl group, a naphthyl group, a biphenyl group, and a terphenyl group are preferable.

In addition, as the heteroaryl group of the heteroarylcarbazolyl group, pyridine, pyrimidine, pyrazine, triazine, aziridine, azaindolizine, indolizine, imidazole, indole, isoindole, indazole, purine, pteridine, β-carboline, naphthyridine, quinoxaline, terpyridine, bipyridine, acridine, phenanthroline, phenazine, imidazopyridine and the like can be given. In particular, a group formed by a ring of pyridine, terpyridine, pyrimidine, imidazopyridine, or triazine is preferable.

The alkyl group of the carbazolylalkyl group preferably has 1 to 10 carbon atoms, and specifically, a methyl group, an ethyl group, a propyl group, an isopropyl group, a n-butyl group, a s-butyl group, a t-butyl group, an isobutyl group, a n-pentyl group, a n-hexyl group, a n-heptyl group, a n-octyl group, a hydroxymethyl group, a chloromethyl group, an aminomethyl group and the like can be given. Of these, a methyl group, an ethyl group, a propyl group, an isopropyl group, a n-butyl group, a t-butyl group, and a n-pentyl group are preferable.

$A^3$ in the formulas (20) and (21) is a group represented by the formula (A).

In the formula (A), $M^1$ and $M^2$ are preferably independently a substituted or unsubstituted nitrogen-containing heterocyclic group having 3 to 40 ring atoms, and may be the same or different.

As the nitrogen-containing heterocyclic ring, pyridine, pyrimidine, pyrazine, triazine, aziridine, azaindolizine, indolizine, imidazole, indole, isoindole, indazole, purine, pteridine, β-carboline, naphthyridine, quinoxaline, terpyridine, bipyridine, acridine, phenanthroline, phenazine, imidazopyridine and the like can be given, and in particular, a group formed by a ring of pyridine, terpyridine, pyrimidine, imidazopyridine, or triazine is preferable.

$L^5$ is a single bond, a substituted or unsubstituted aromatic hydrocarbon ring group or fused aromatic hydrocarbon ring group having 6 to 30 carbon atoms, a substituted or unsubstituted cycloalkylene group having 5 to 30 carbon atoms, or a substituted or unsubstituted aromatic heterocyclic group or fused aromatic heterocyclic group having 2 to 30 carbon atoms.

c is an integer of 0 to 2, d is an integer of 1 to 2, and e is an integer of 0 to 2. c+e is 1 or more.

Specific examples of the compounds represented by the formula (20) are shown below.

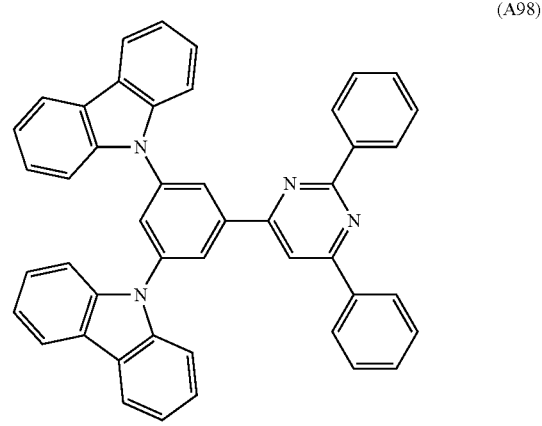

(A98)

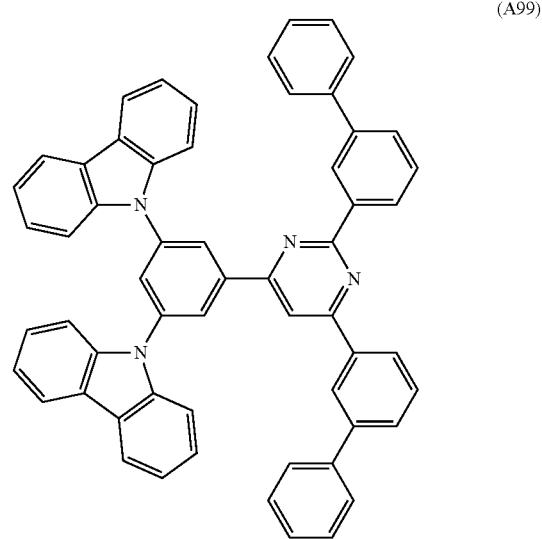

(A99)

-continued
(A100)
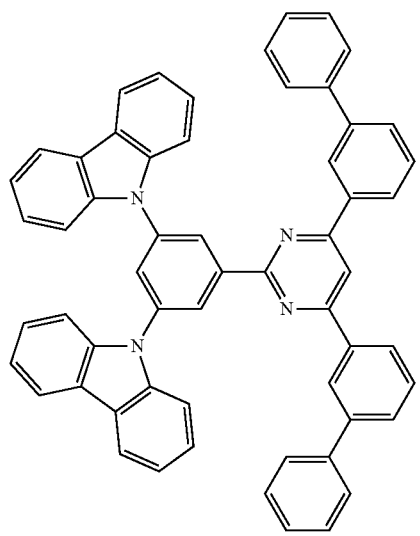
(A101)
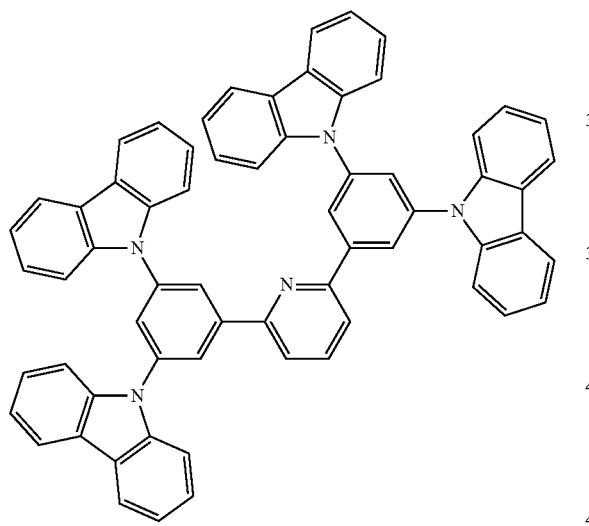
(A102)
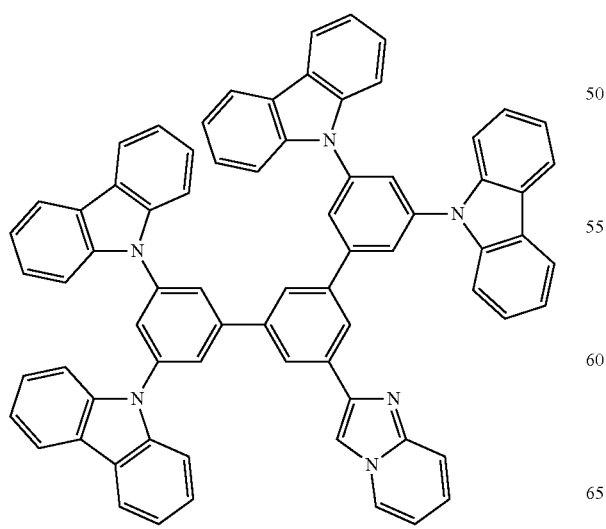
-continued
(A103)
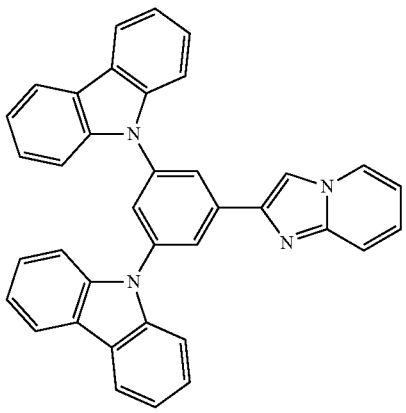
(A104)
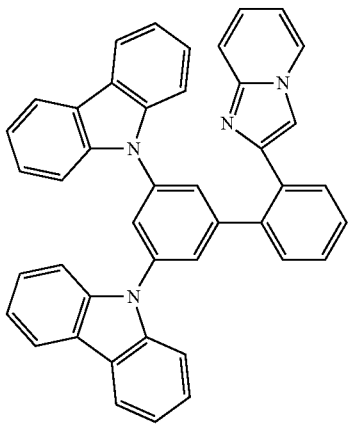
(A105)
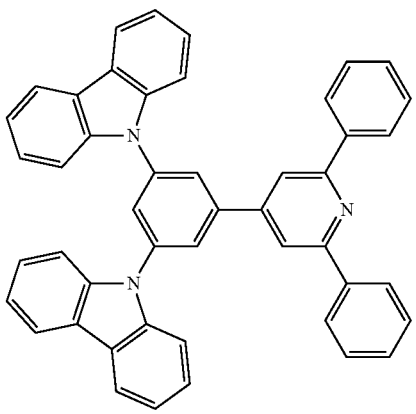

(A106)
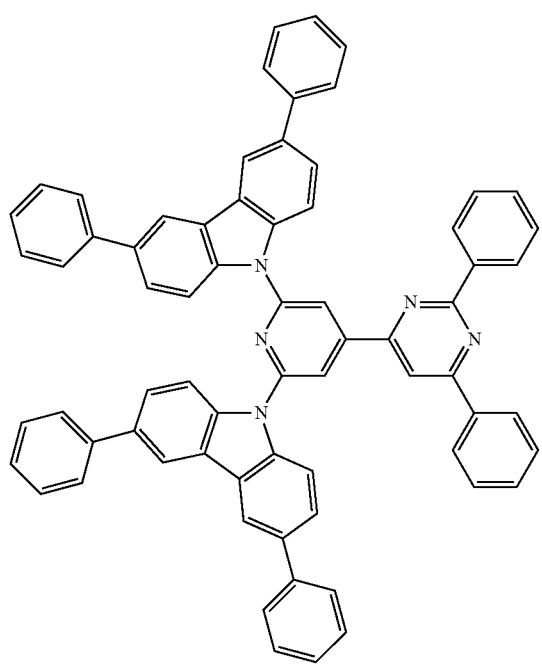
(A107)
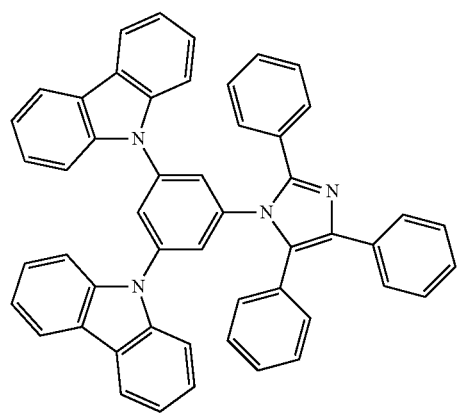
(A108)
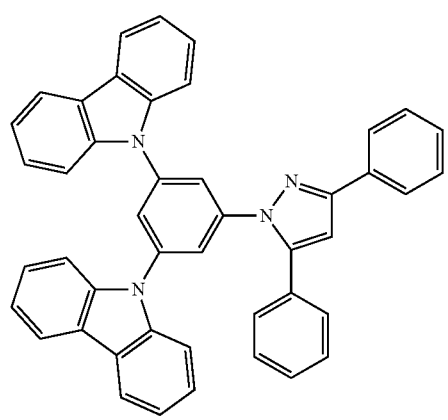
(A109)
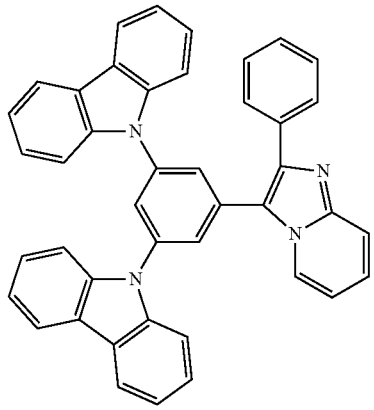
(A110)
(A111)
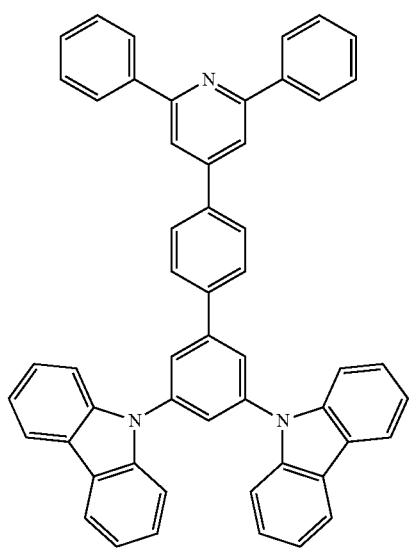

(A112)
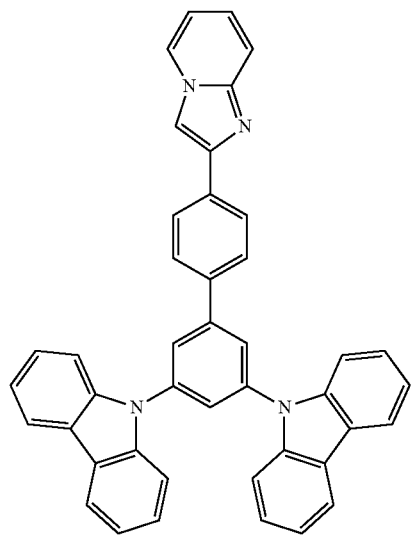
(A113)
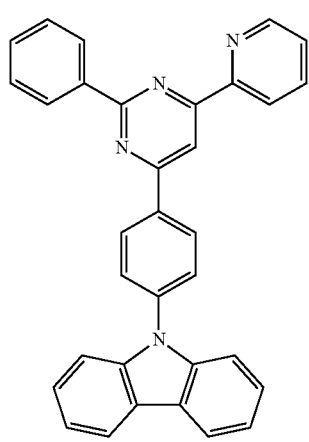
(A114)
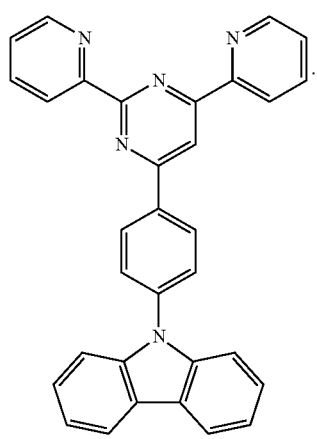
(B1)
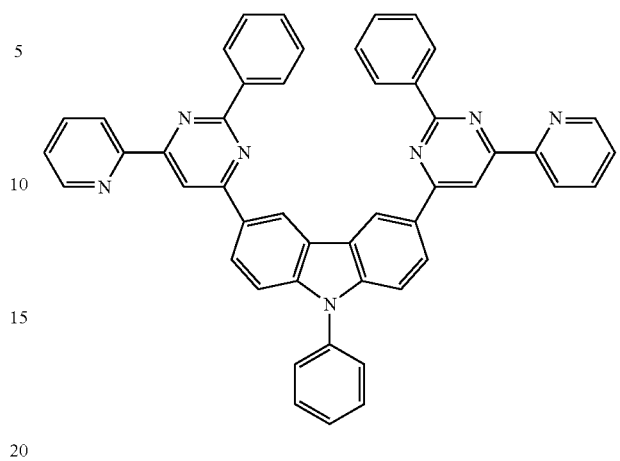
(B2)
(B3)
Specific examples of the compounds represented by the formula (21) are shown below.

-continued
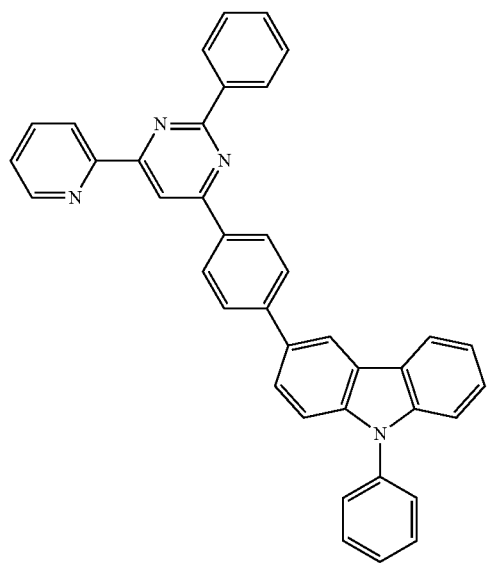
(B4)
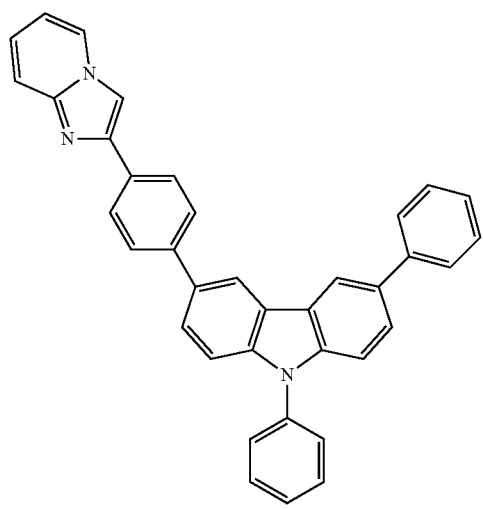
(B5)
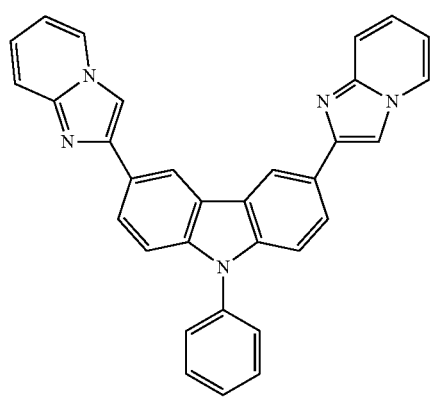
(B6)
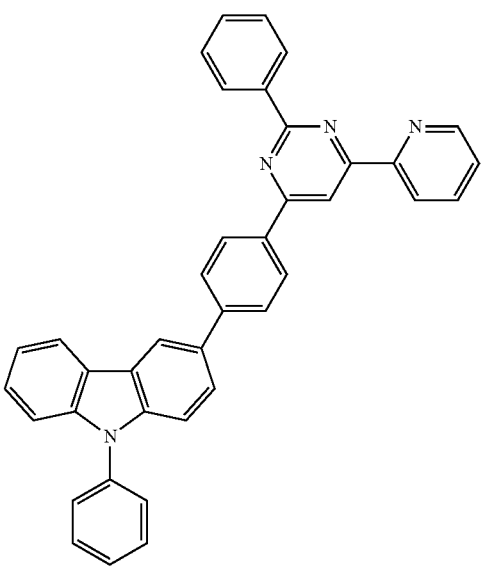
(B7)
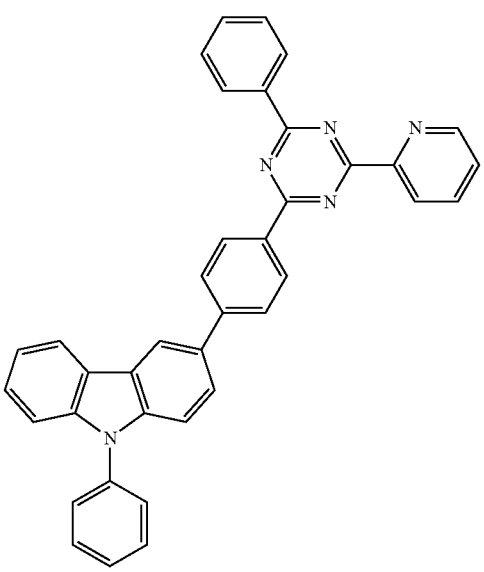
(B8)
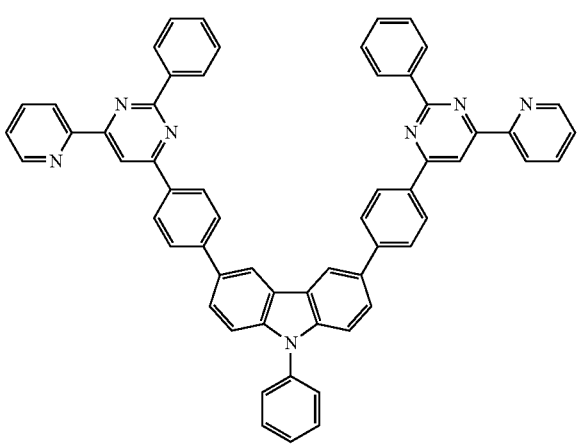
(B9)

(B10)
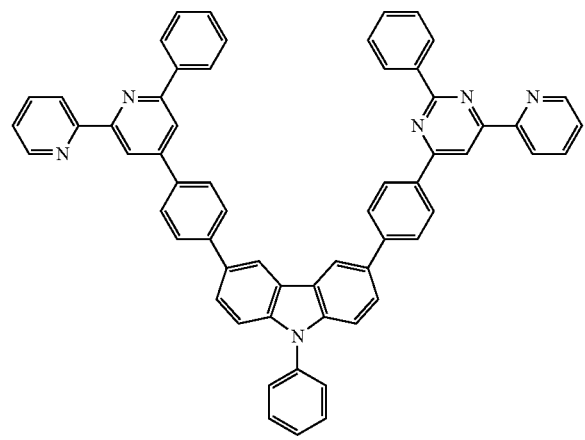
(B11)
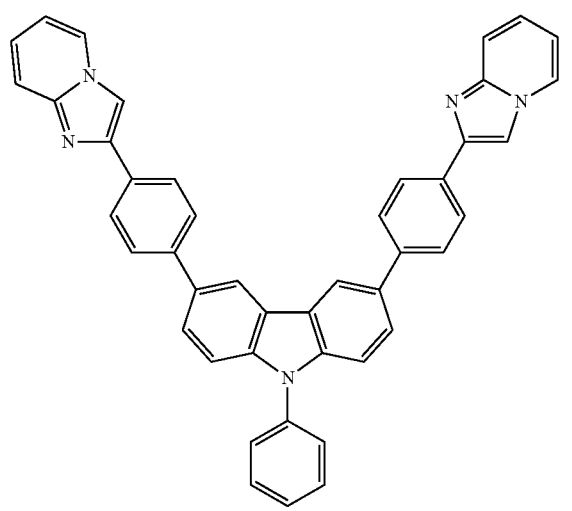
(B12)
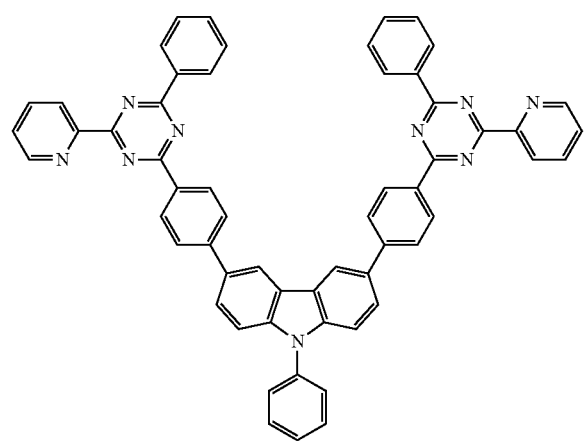
(B13)
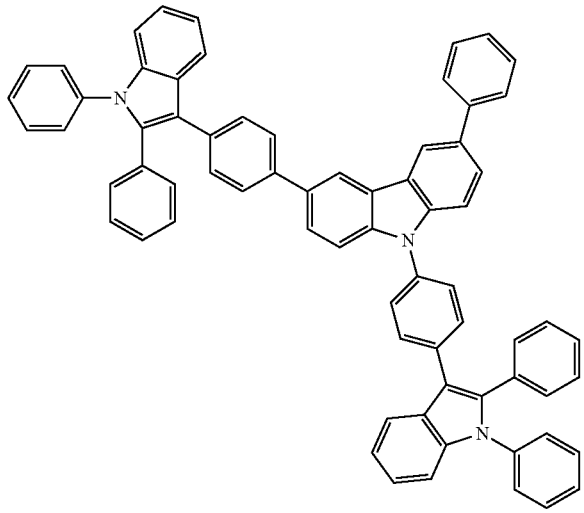
(B14)
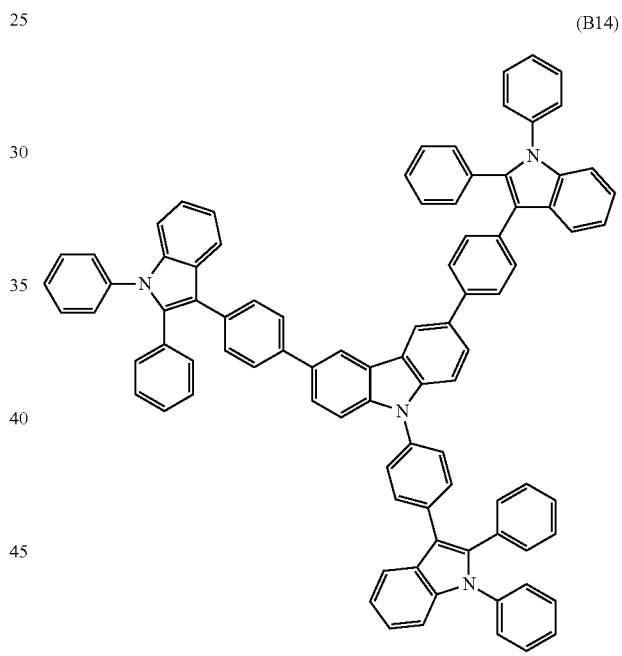
In addition, it is preferable that the compounds represented by the formulas (30) to (33) be contained in at least one layer of the organic thin film layers, preferably in an emitting layer. These compounds are preferably used as a host material in the emitting layer.
(30)
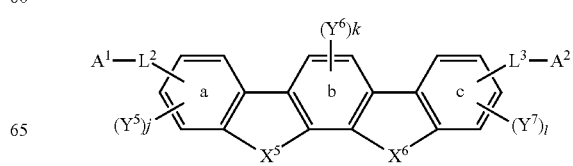

-continued

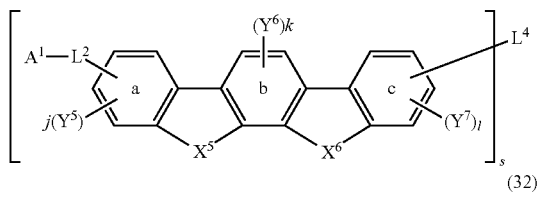

(31)

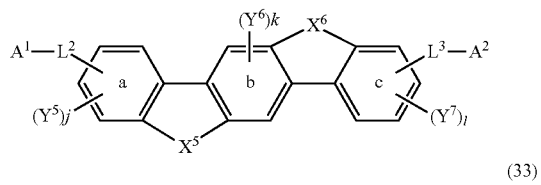

(32)

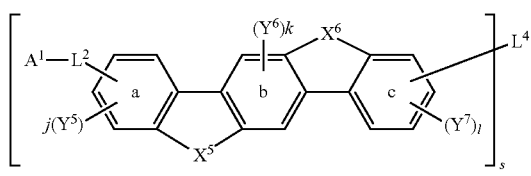

(33)

In the formulas (30) to (33), $X^5$ and $X^6$ are independently oxygen (O), sulfur (S), N—$R^1$ or $CR^2R^3$. $R^1$, $R^2$ and $R^3$ above are independently an alkyl group having 1 to 20 carbon atoms, a substituted or unsubstituted cycloalkyl group having 3 to 20 ring carbon atoms, an aralkyl group having 7 to 24 carbon atoms, a silyl group or a substituted silyl group having 3 to 20 carbon atoms, a substituted or unsubstituted aromatic hydrocarbon ring group or fused aromatic hydrocarbon ring group having 6 to 24 ring carbon atoms, or a substituted or unsubstituted aromatic heterocyclic group or fused aromatic heterocyclic group having 3 to 24 ring carbon atoms. When both $X^5$ and $X^6$ are N—$R^1$, at least one $R^1$ is a substituted or unsubstituted, monovalent fused aromatic heterocyclic group having 8 to 24 ring atoms.

In the formulas (31) and (33), s is 2, 3 or 4 wherein the compound is a dimer, a trimer, or a tetramer having $L^4$ as a linking group.

In the formulas (30) to (33), $L^2$ is a single bond, an alkylene group having 1 to 20 carbon atoms, a substituted or unsubstituted cycloalkylene group having 3 to 20 ring carbon atoms, a substituted or unsubstituted silylene group having 2 to 20 carbon atoms, a substituted or unsubstituted divalent aromatic hydrocarbon ring group or fused aromatic hydrocarbon ring group having 6 to 24 ring carbon atoms, or a substituted or unsubstituted divalent aromatic heterocyclic group or fused aromatic heterocyclic group having 3 to 24 ring carbon atoms.

In the formulas (30) and (32), $L^3$ is a single bond, an alkylene group having 1 to 20 carbon atoms, a substituted or unsubstituted cycloalkylene group having 3 to 20 ring carbon atoms, a substituted or unsubstituted silylene group having 2 to 20 carbon atoms, a substituted or unsubstituted divalent aromatic hydrocarbon ring group or fused aromatic hydrocarbon ring group having 6 to 24 ring carbon atoms, or a substituted or unsubstituted divalent aromatic heterocyclic group or fused aromatic heterocyclic group having 3 to 24 ring carbon atoms.

In the formulas (31) and (33), when s is 2, $L^4$ is a single bond, an alkylene group having 1 to 20 carbon atoms, a substituted or unsubstituted cycloalkylene group having 3 to 20 ring carbon atoms, a substituted or unsubstituted silylene group having 2 to 20 carbon atoms, a substituted or unsubstituted divalent aromatic hydrocarbon ring group or fused aromatic hydrocarbon ring group having 6 to 24 ring carbon atoms, or a substituted or unsubstituted divalent aromatic heterocyclic group or fused aromatic heterocyclic group having 3 to 24 ring carbon atoms. When s is 3, $L^4$ is a trivalent group of the above groups. When s is 4, $L^4$ is a tetravalent group of the above groups.

In the formulas (30) to (33), $A^1$ is a hydrogen atom, a substituted or unsubstituted cycloalkyl group having 3 to 20 ring carbon atoms, a substituted or unsubstituted silyl group having 3 to 20 carbon atoms, a substituted or unsubstituted aromatic hydrocarbon ring group or fused aromatic hydrocarbon ring group having 6 to 24 ring carbon atoms, or a substituted or unsubstituted aromatic heterocyclic group or fused aromatic heterocyclic group having 3 to 24 ring carbon atoms.

In the formulas (30) and (32), $A^2$ is a hydrogen atom, a substituted or unsubstituted cycloalkyl group having 3 to 20 ring carbon atoms, a substituted or unsubstituted silyl group having 3 to 20 carbon atoms, a substituted or unsubstituted aromatic hydrocarbon ring group or fused aromatic hydrocarbon ring group having 6 to 24 ring carbon atoms, or a substituted or unsubstituted aromatic heterocyclic group or fused aromatic heterocyclic group having 3 to 24 ring carbon atoms.

In the formulas (30) to (33), $Y^5$, $Y^6$ and $Y^7$ are an alkyl group having 1 to 20 carbon atoms, a substituted or unsubstituted cycloalkyl group having 3 to 20 ring carbon atoms, an alkoxy group having 1 to 20 carbon atoms, an aralkyl group having 7 to 24 carbon atoms, a substituted or unsubstituted silyl group having 3 to 20 carbon atoms, a substituted or unsubstituted aromatic hydrocarbon ring group or fused aromatic hydrocarbon ring group having 6 to 24 ring carbon atoms, or a substituted or unsubstituted aromatic heterocyclic group or fused aromatic heterocyclic group having 3 to 24 ring carbon atoms. j and l are 0, 1, 2 or 3, and k is 0, 1 or 2.

In the formulas (30) to (33), $A^1$, $A^2$, $L^2$, $L^3$ and $L^4$ contain no carbonyl group.

In addition, it is preferable that the anthracene derivative represented by the following formula (40) or the pyrene derivative represented by the following formula (41) be contained in at least one layer of the organic thin film layers, preferably in an emitting layer. These compounds are preferably used as a host material in the emitting layer.

(Anthracene Derivative)

The anthracene derivative represented by the formula (40) is the following compound.

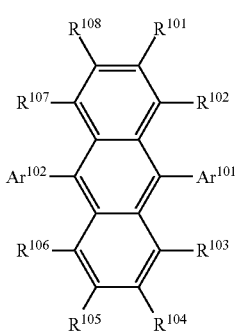

(40)

In the formula (40), $Ar^{101}$ and $Ar^{102}$ are independently a group selected from a substituted or unsubstituted monocyclic group having 5 to 50 ring atoms, a substituted or unsubstituted fused ring group having 8 to 50 ring atoms, or a group formed from a combination of a monocyclic group and a fused ring group. $R^{101}$ to $R^{108}$ are independently a group selected from a hydrogen atom, a substituted or unsubstituted monocyclic group having 5 to 50 ring atoms, a substituted or unsubstituted fused ring group having 8 to 50 ring atoms, a group formed from a combination of a monocyclic group and a fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

As the monocyclic group having 5 to 50 ring atoms (preferably 5 to 30, more preferably 5 to 20 ring atoms), an aromatic group such as a phenyl group, a biphenyl group, a terphenyl group, a quarterphenyl group and the like, and a heterocyclic group such as a pyridyl group, a pyrazyl group, a pyrimidyl group, a triazinyl group, a furyl group, a thienyl group and the like are specifically preferable.

Of these, a phenyl group, a biphenyl group, and a terphenyl group are preferable.

As the fused ring group having 8 to 50 ring atoms (preferably 8 to 30, more preferably 8 to 20 ring atoms), a fused aromatic ring group such as a naphthyl group, a phenanthryl group, an anthryl group, a chrysenyl group, a benzoanthryl group, a benzophenanthryl group, a triphenylenyl group, a benzochrysenyl group, an indenyl group, a fluorenyl group, a 9,9-dimethylfluorenyl group, a benzofluorenyl group, a dibenzofluorenyl group, a fluoranthenyl group, a benzofluoranthenyl group and the like, and a fused heterocyclic group such as a benzofuranyl group, a benzothiophenyl group, an indoryl group, a dibenzofuranyl group, a dibenzothiophenyl group, a carbazolyl group, a quinolyl group, a phenanthrolinyl group and the like are specifically preferable.

Of these, a naphthyl group, a phenanthryl group, an anthryl group, a 9,9-dimethylfluorenyl group, a fluoranthenyl group, a benzoanthryl group, a dibenzothiophenyl group, a dibenzofuranyl group, and a carbazolyl group are preferable.

Specific examples of an alkyl group, a substituted silyl group, a cycloalkyl group, and a halogen atom of the formula (40) are the same as those of the groups of the above formulas (1) to (3).

The alkoxy group is represented by —OY, and as an example of Y, the examples of the alkyl group above can be given. The alkoxy group is a methoxy group or an ethoxy group, for example.

The aryloxy group is represented by —OZ, and as an example of Z, the examples of the aryl group above can be given. The aryloxy group is a phenoxy group, for example.

The aralkyl group is represented by —Y—Z. As an example of Y, the examples of the alkylene corresponding to the alkyl above can be given, and as an example of Z, the examples of the aryl above can be given. The aralkyl group is preferably an aralkyl group having 7 to 50 carbon atoms (the aryl part has 6 to 49 carbon atoms (preferably 6 to 30, more preferably 6 to 20, particularly preferably 6 to 12 carbon atoms) and the alkyl part has 1 to 44 carbon atoms (preferably 1 to 30, more preferably 1 to 20, further preferably 1 to 10, particularly preferably 1 to 6 carbon atoms)), and is a benzyl group, a phenylethyl group, or a 2-phenylpropane-2-yl group, for example.

Specific preferable examples of the formula (40) are shown below.

As a preferable substituent of the "substituted or unsubstituted" instance of $Ar^{101}$, $Ar^{102}$, and $R^{101}$ to $R^{108}$, a monocyclic group, a fused ring group, an alkyl group, a cycloalkyl group, a silyl group, an alkoxy group, a cyano group, and a halogen atom (particularly fluorine) can be given, and a monocyclic group and a fused ring group are particularly preferable. Specific preferable examples are as shown above.

The anthracene derivative represented by the formula (40) is preferably one of the following anthracene derivatives (A), (B) and (C), and is selected depending on the structure and the desired property of an organic EL device to which the derivative is applied.

(Anthracene Derivative (A))

In the anthracene derivative (A), $Ar^{101}$ and $Ar^{102}$ in the formula (40) are independently a substituted or unsubstituted fused ring group having 8 to 50 ring atoms. The anthracene derivative can be classified into an instance where $Ar^{101}$ and $Ar^{102}$ are the same substituted or unsubstituted fused ring group and an instance where $Ar^{101}$ and $Ar^{102}$ are different substituted or unsubstituted fused ring groups.

It is preferable that $Ar^{101}$ and $Ar^{102}$ in the formula (40) be different substituted or unsubstituted fused ring groups (including the difference in substitution position), and specific preferable examples of the fused ring group are as shown above. Of these, a naphthyl group, a phenanthryl group, a benzanthryl group, a 9,9-dimethylfluorenyl group, and a dibenzofuranyl group are preferable.

(Anthracene Derivative (B))

In the anthracene derivative (B), one of $Ar^{101}$ and $Ar^{102}$ in the formula (40) is a substituted or unsubstituted monocyclic group having 5 to 50 ring atoms, and the other is a substituted or unsubstituted fused ring group having 8 to 50 ring atoms.

As a preferable embodiment, $Ar^{102}$ is a naphthyl group, a phenanthryl group, a benzanthryl group, a 9,9-dimethylfluorenyl group, or a dibenzofuranyl group, and $Ar^{101}$ is a phenyl group substituted with a monocyclic group or a fused ring group.

Specific preferable monocyclic group and fused ring group are as shown above.

As another preferable embodiment, $Ar^{102}$ is a fused ring group and $Ar^{101}$ is a unsubstituted phenyl group. In this case, as the fused ring group, a phenanthryl group, a 9,9-dimethylfluorenyl group, a dibenzofuranyl group, and a benzanthryl group are particularly preferable.

(Anthracene Derivative (C))

In the anthracene derivative (C), $Ar^{101}$ and $Ar^{102}$ in the formula (40) are independently a substituted or unsubstituted monocyclic group having 5 to 50 ring atoms.

As a preferable embodiment, $Ar^{101}$ and $Ar^{102}$ are both a substituted or unsubstituted phenyl group.

As a further preferable embodiment, $Ar^{101}$ is an unsubstituted phenyl group and $Ar^{102}$ is a phenyl group having a monocyclic group and/or a fused ring group as a substituent, or $Ar^{101}$ and $Ar^{102}$ are independently a phenyl group having a monocyclic group and/or a fused ring group as a substituent.

Specific preferable monocyclic group and fused ring group as the substituent are as shown above. More preferably, as a substituent, the monocyclic group may be a phenyl group or a biphenyl group, and the fused ring group may be a naphthyl group, a phenanthryl group, a 9,9-dimethylfluorenyl group, a dibenzofuranyl group, or a benzoanthryl group.

(Pyrene Derivative)

The pyrene derivative represented by the following formula (41) is the following compound.

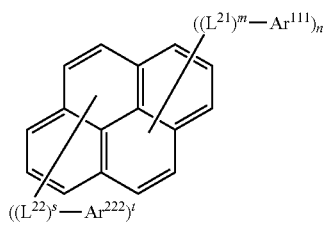

(41)

(50)

In the formula (41), $Ar^{111}$ and $Ar^{222}$ are independently a substituted or unsubstituted aryl group having 6 to 30 ring carbon atoms.

$L^{21}$ and $L^{22}$ are independently a substituted or unsubstituted divalent aryl group or heterocyclic group having 6 to 30 ring carbon atoms.

m is an integer of 0 to 1, n is an integer of 1 to 4, s is an integer of 0 to 1, and t is an integer of 0 to 3.

In addition, $L^{21}$ or $Ar^{111}$ is connected with any of 1st to 5th position of the pyrene, and $L^{22}$ or $Ar^{222}$ is connected with any of 6- to 10-position of the pyrene.

$L^{21}$ and $L^{22}$ of the formula (41) are preferably a substituted or unsubstituted phenylene group, a substituted or unsubstituted biphenylene group, a substituted or unsubstituted naphthylene group, a substituted or unsubstituted terphenylene group, a substituted or unsubstituted fluorenylene group, and a divalent aryl group composed of a combination of these substituent groups.

In addition, examples of the substituent groups are as shown above. The substituent groups of $L^{21}$ and $L^{22}$ are preferably an alkyl group having 1 to 20 carbon atoms.

m in the formula (41) is preferably an integer of 0 to 1. n in the formula (41) is preferably an integer of 1 to 2. s in the formula (41) is preferably an integer of 0 to 1.

t in the formula (41) is preferably an integer of 0 to 2.

The aryl groups of $Ar^{111}$ and $Ar^{222}$ are as shown above.

The aryl group is preferably a substituted or unsubstituted aryl group having 6 to 20 ring carbon atoms, more preferably a substituted or unsubstituted aryl group having 6 to 16 ring carbon atoms, and specific preferable examples of the aryl group include a phenyl group, a naphthyl group, a phenanthryl group, a fluorenyl group, a biphenyl group, an anthryl group, and a pyrenyl group.

When the compounds of the above formulas (20), (21), (30) to (33), (40), and (41) are used as a host material in an emitting layer, two or more of these can be used in combination.

The emitting layer may contain an emitting dopant (a phosphorescent dopant and or a fluorescent dopant) in addition to the emitting material.

The fluorescent dopant is a compound capable of emitting from a singlet exciton. The fluorescent dopant is preferably selected from an amine compound, an aromatic compound, a chelate complex such as tris(8-quinolinolate)aluminum complex, a coumarin derivative, a tetraphenylbutadiene derivative, a bisstyrylarylene derivative, an oxadiazole derivative and the like, depending on the desired emission color. A styrylamine compound, a styryldiamine compound, an arylamine compound, and an aryldiamine compound are more preferable, and a fused polycyclic amine derivative is further preferable. These fluorescent dopants may be used alone or in combination.

It is preferable that the fused polycyclic amine derivative be one represented by the following formula (50).

In the formula (50), Y is a substituted or unsubstituted fused aryl group having 10 to 50 ring carbon atoms.

$Ar_{201}$ and $Ar_{202}$ are independently a substituted or unsubstituted aryl group having 6 to 50 ring carbon atoms, or a substituted or unsubstituted heterocyclic group having 5 to 50 ring atoms.

The fused aryl group is a group composed by fusion of two or more ring structures, among the aryl groups above.

The fused aryl group is a fused aryl group having 10 to 50 ring carbon atoms (preferably 10 to 30, more preferably 10 to 20 ring carbon atoms), and among specific examples of the aryl group above, a naphthyl group, an anthryl group, a pyrenyl group, a phenanthryl group, a fluorenyl group, a fluoranthenyl group, a naphthacenyl group and the like can preferably be given.

As specific examples of Y, the fused aryl group above can be given, and a substituted or unsubstituted anthryl group, a substituted or unsubstituted pyrenyl group, and a substituted or unsubstituted chrysenyl group are preferable.

As a preferable example of $Ar_a$), and $Ar_{202}$, a substituted or unsubstituted phenyl group, a substituted or unsubstituted dibenzofuranyl group and the like can be given. As a preferable example of the substituent of $Ar_{201}$ and $Ar_{202}$, an alkyl group, a cyano group, and a substituted or unsubstituted silyl group can be given.

n is an integer of 1 to 4, and is preferably an integer of 1 to 2.

As the styrylamine compound and the styryldiamine compound, compounds represented by the following formulas (51) and (52) are preferable.

(51)

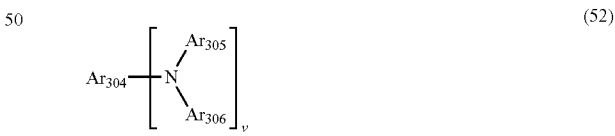

(52)

In the formula (51), $Ar_{301}$ is a group having a valence of k, and is a group having a valence of k corresponding to a phenyl group, a naphthyl group, a biphenyl group, a terphenyl group, a stilbene group, a styrylaryl group, or a distyrylaryl group. $Ar_{302}$ and $Ar_{303}$ are independently an aryl group having 6 to 20 ring carbon atoms, and $Ar_{301}$, $Ar_{302}$ and $Ar_{303}$ may be substituted.

k is an integer of 1 to 4, and is preferably an integer of 1 to 2. Any one of $Ar_{301}$ to $Ar_{303}$ is a group comprising a styryl group. More preferably, at least one of $Ar_{302}$ and $Ar_{303}$ is substituted with a styryl group.

As the aryl group having 6 to 20 ring carbon atoms, the aryl groups shown above can specifically be given, and a phenyl group, a naphthyl group, an anthranyl group, a phenanthryl group, a terpenyl group and the like can preferably be given.

In the formula (52), $Ar_{304}$ to $Ar_{306}$ are a substituted or unsubstituted aryl group having 6 to 40 ring carbon atoms and a valence of v. v is an integer of 1 to 4, and is preferably an integer of 1 to 2.

As the aryl group having 6 to 40 ring carbon atoms of the formula (52), the aryl groups shown above can specifically be given, and an aryl group represented by a naphthyl group, an anthranyl group, a chrysenyl group, or a pyrenyl group is preferable.

As a preferable substituent on the aryl group above, an alkyl group having 1 to 6 carbon atoms, an alkoxy group having 1 to 6 carbon atoms, an aryl group having 6 to 40 ring carbon atoms, an amino group substituted with an aryl group having 6 to 40 ring carbon atoms, an ester group which has an aryl group having 5 to 40 ring carbon atoms, an ester group which has an alkyl group having 1 to 6 carbon atoms, a cyano group, a nitro group, a halogen atom and the like can be given.

The phosphorescent dopant is a compound capable of emitting from a triplet exciton.

The phosphorescent dopant contains a metal complex, and the metal complex preferably has a metal atom selected from Ir, Pt, Os, Au, Cu, Re and Ru, and a ligand. In particular, the ligand preferably has an ortho-metal bond.

The compound containing the metal atom selected from Ir, Os and Pt is preferable in that phosphorescent quantum efficiency is high so that external quantum efficiency of a light emitting device can be more improved. The metal complex such as an iridium complex, an osmium complex, a platinum complex and the like is further preferable, and of these, an iridium complex and a platinum complex are more preferable with an ortho-metalated iridium complex being most preferable.

Specific preferable examples of the metal complex are shown below.

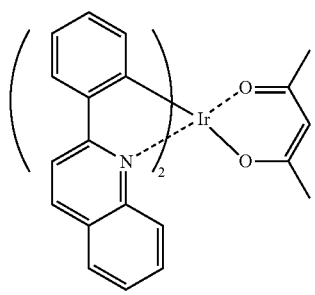

PQIr

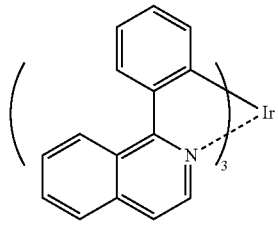

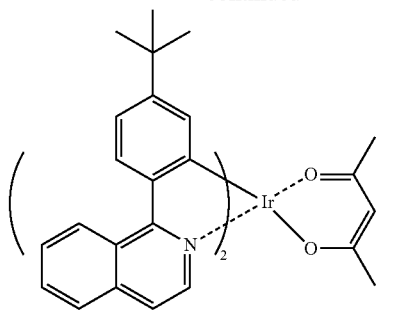

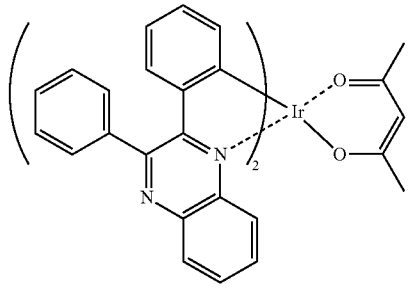

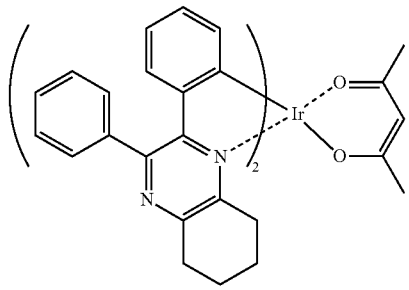

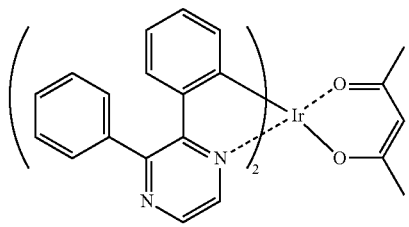

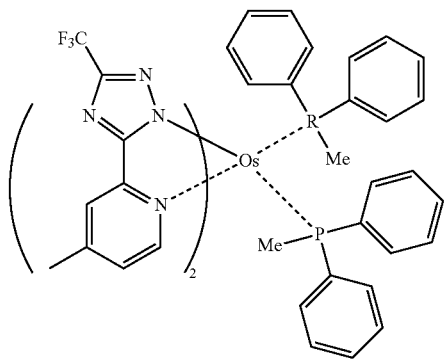

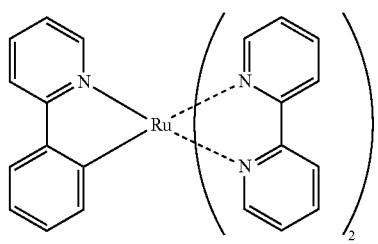

97
-continued
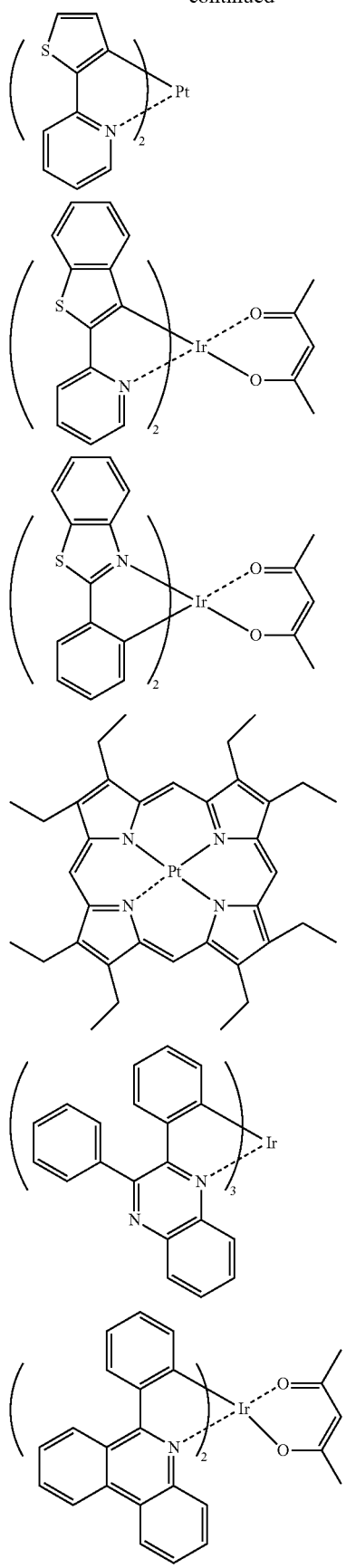
98
-continued
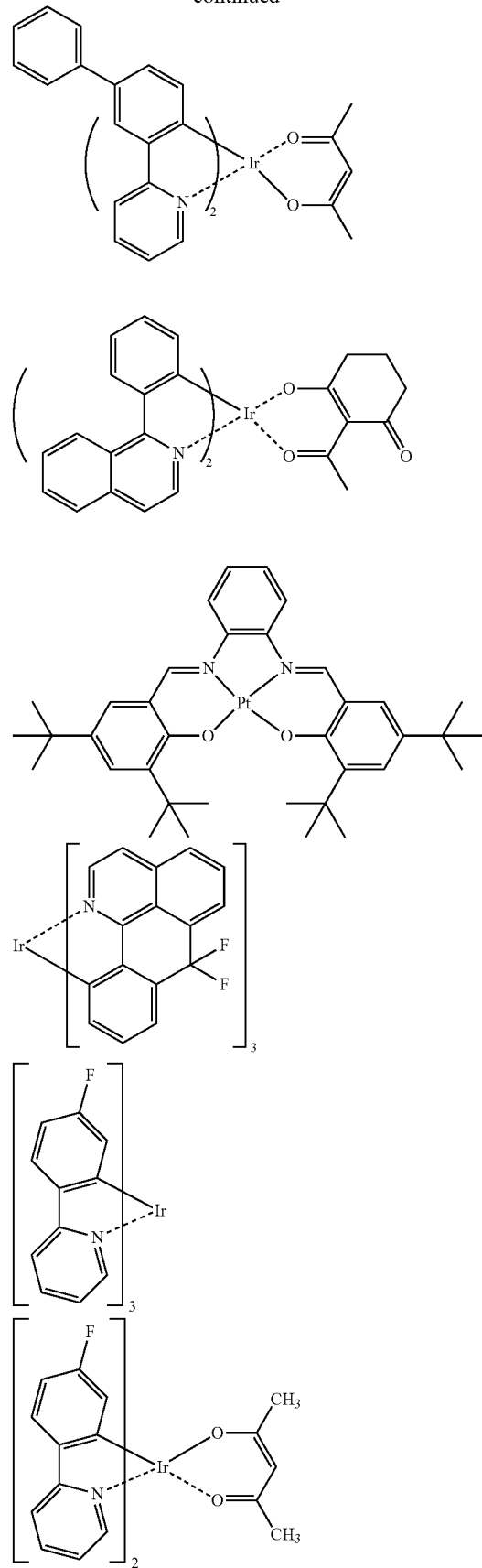

-continued
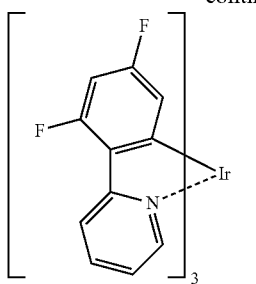
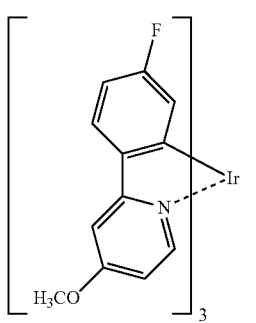
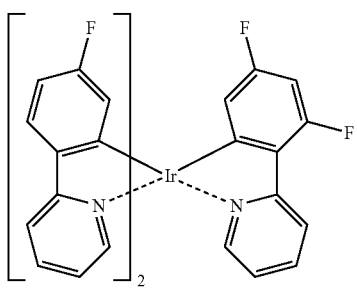
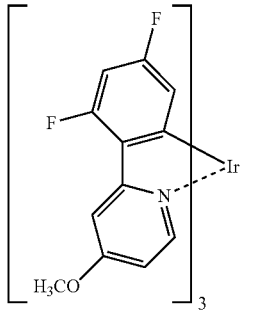
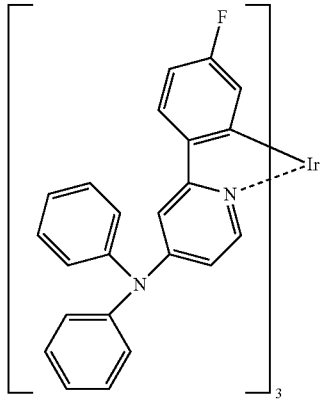
-continued
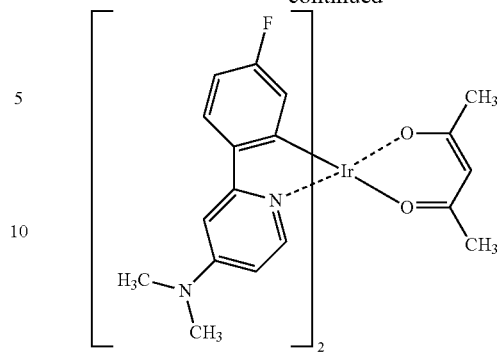
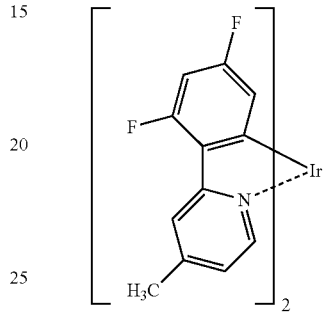
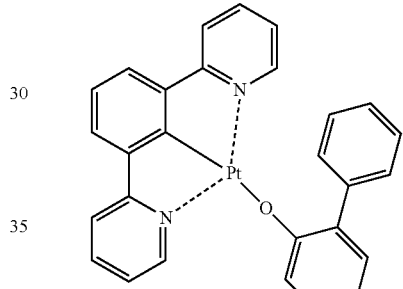
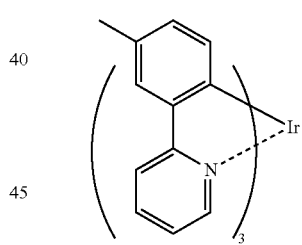
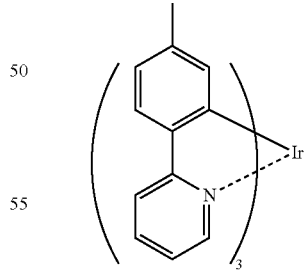
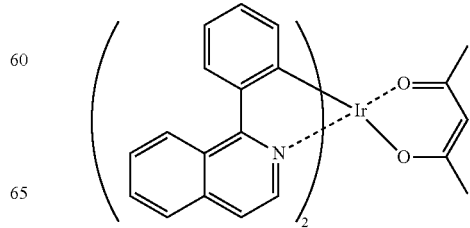

101
-continued
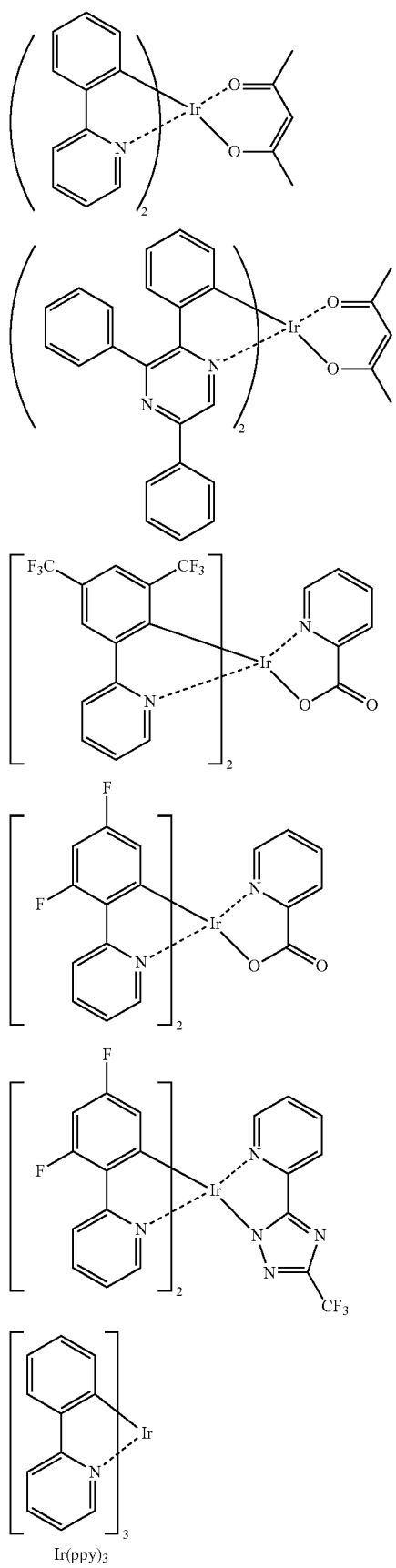
102
-continued
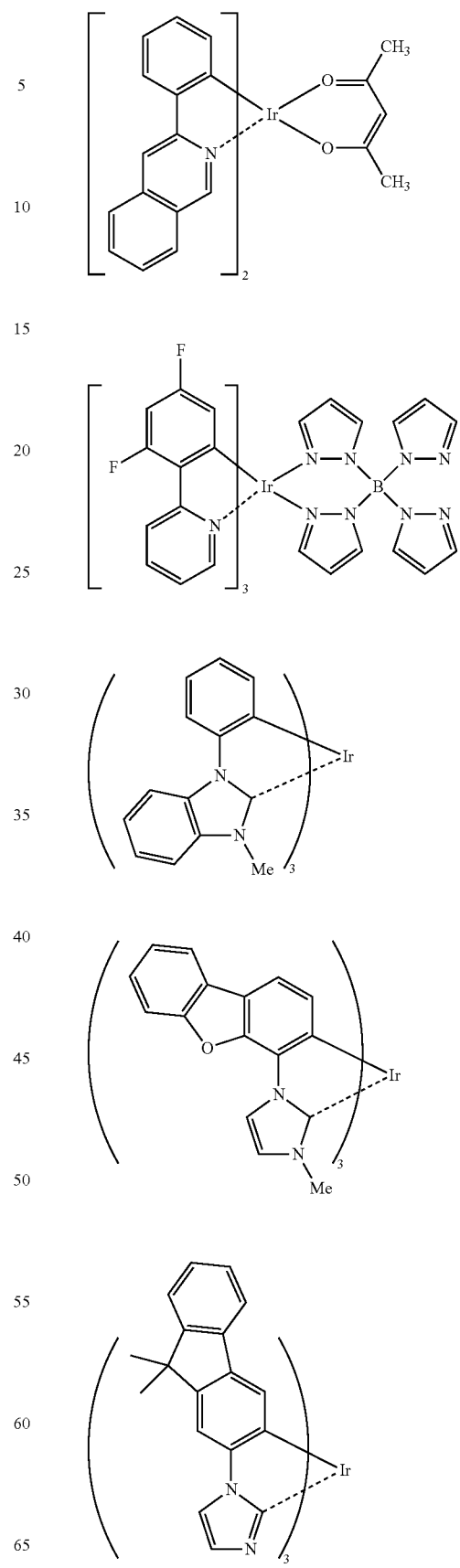

103
-continued
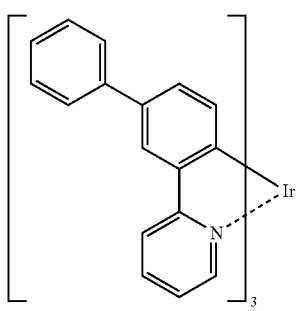
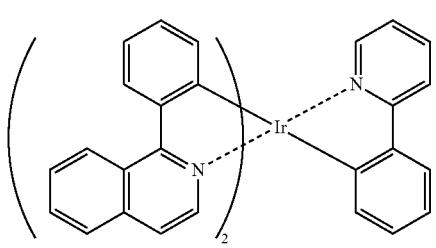
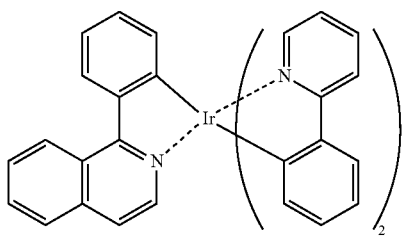
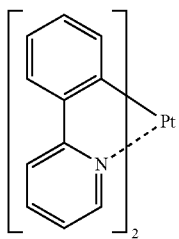
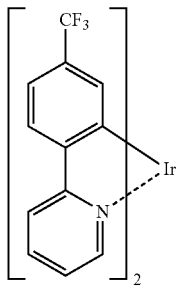
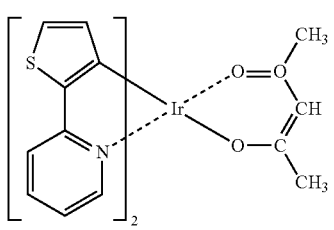
104
-continued
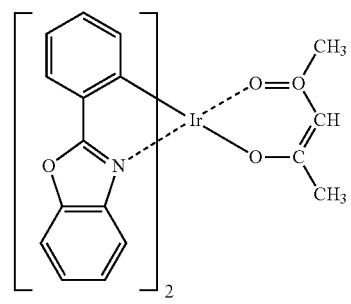
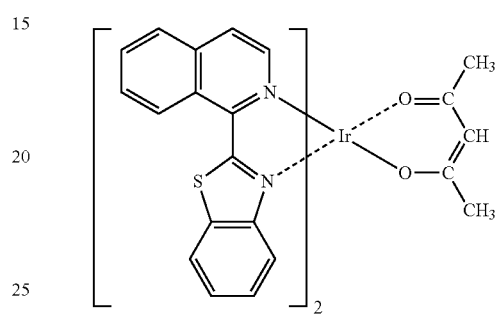
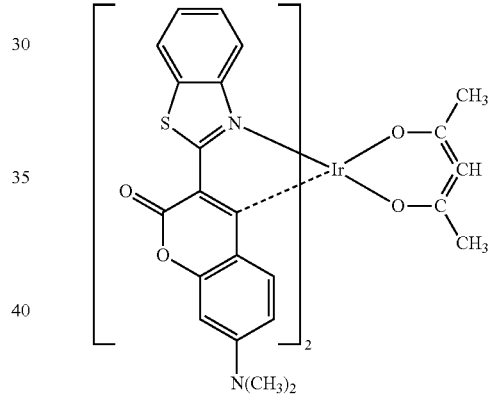
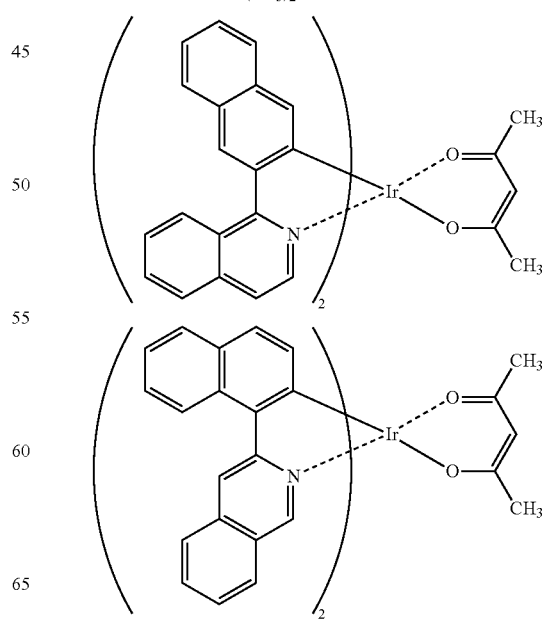
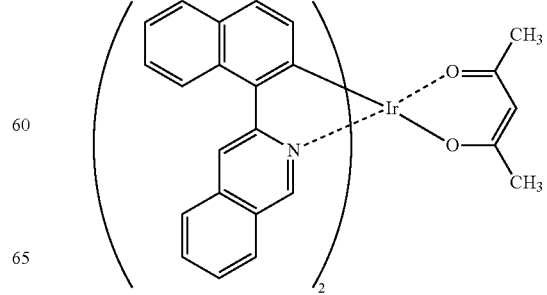

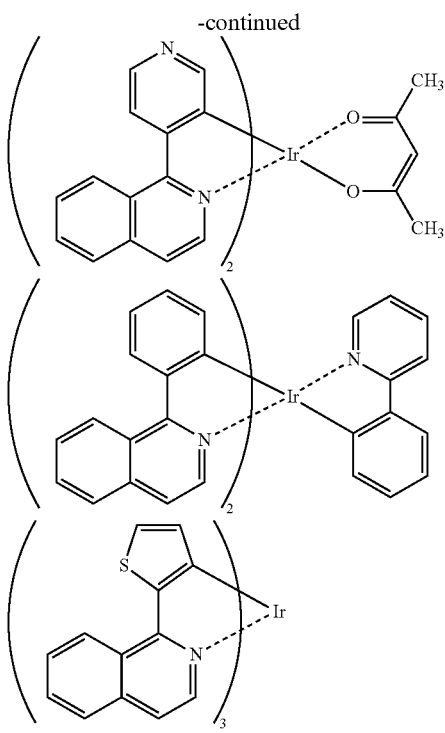

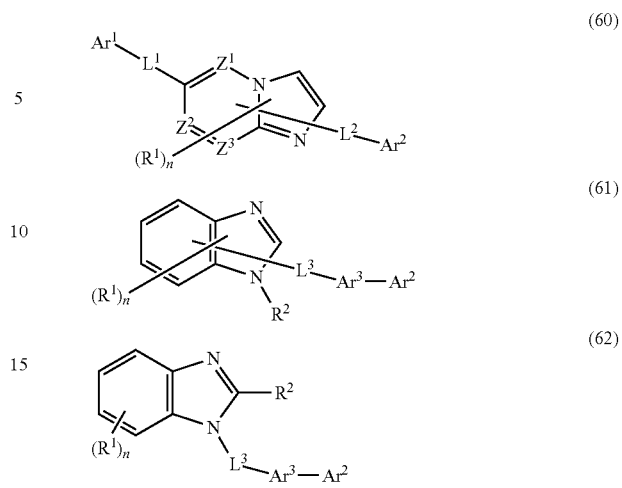

As an electron-injecting and/or -transporting material, a compound having a capability of transporting an electron, an electron-injecting effect from a cathode, an excellent electron-injecting effect against an emitting layer or an emitting material, and an excellent capability of forming a thin film is preferable.

In the organic EL device of the invention, a more effective electron-injecting material is a metal complex compound and a nitrogen-containing heterocyclic derivative.

As the metal complex compound, although not being limited thereto, 8-hydroxyquinolinate lithium, bis(8-hydroxyquinolinate) zinc, tris(8-hydroxyquinolinate)aluminum, tris (8-hydroxyquinolinato) gallium, bis(10-hydroxybenzo[h] quinolinato) beryllium, bis(10-hydroxybenzo[h]quinolinato) zinc and the like can be given, for example.

As the nitrogen-containing heterocyclic derivative, oxazole, thiazole, oxadiazole, thiadiazole, triazole, pyridine, pyrimidine, triazine, phenanthroline, benzimidazole, imidazopyridine and the like are preferable, for example. Of these, a benzimidazole derivative, a phenanthroline derivative, and an imidazopyridine derivative are preferable.

As a preferable embodiment, these electron-injecting materials further contain a dopant, and it is more preferable that a dopant represented by an alkali metal be contained near the boundary face between an organic layer and a cathode so as to facilitate receipt of an electron from a cathode.

As the dopant, a donating metal, a donating metal compound, and a donating metal complex can be given, and these reducing dopants may be used alone or in combination of two or more.

In addition, in the organic EL device of the invention, it is preferable that the device have at least an electron-transporting layer as an organic thin film layer and that the nitrogen-containing heterocyclic derivative represented by any of the following formulas (60) to (62) be contained in the electron-transporting layer.

In the formulas (60) to (62), $Z^1$, $Z^2$ and $Z^3$ are independently a nitrogen atom or a carbon atom.

$R^1$ and $R^2$ are independently a substituted or unsubstituted aryl group having 6 to 50 ring carbon atoms, a substituted or unsubstituted heteroaryl group having 3 to 50 ring atoms, an alkyl group having 1 to 20 carbon atoms, an alkyl group substituted with a halogen atom having 1 to 20 carbon atoms, or an alkoxy group substituted having 1 to 20 carbon atoms. The aryl group such as a substituted or unsubstituted phenyl group having 6 to 50 ring carbon atoms and the like is preferable.

n is an integer of 0 to 4, and when n is an integer of 2 or more, plural R's may be the same or different each other. In addition, adjacent two R's may be bonded each other to form a substituted or unsubstituted aromatic hydrocarbon ring.

$Ar^1$ is a substituted or unsubstituted aryl group having 6 to 50 ring carbon atoms, or a substituted or unsubstituted heteroaryl group having 3 to 50 ring atoms.

$Ar^2$ is a hydrogen atom, an alkyl group having 1 to 20 carbon atoms, an alkyl group substituted with a halogen atom having 1 to 20 carbon atoms, an alkoxy group having 1 to 20 carbon atoms, a substituted or unsubstituted aryl group having 6 to 50 ring carbon atoms, or a substituted or unsubstituted heteroaryl group having 3 to 50 ring atoms.

In the formula (60), one of $Ar^1$ and $Ar^2$ is a substituted or unsubstituted fused aromatic hydrocarbon ring group having 10 to 50 ring carbon atoms (for example, a naphthyl group), or a substituted or unsubstituted fused aromatic heterocyclic group having 9 to 50 ring atoms.

$Ar^3$ is a substituted or unsubstituted arylene group having 6 to 50 ring carbon atoms (for example, an anthracenylene group), or a substituted or unsubstituted heteroarylene group having 3 to 50 ring atoms.

$L^1$, $L^2$ and $L^3$ are independently a single bond, a substituted or unsubstituted arylene group having 6 to 50 ring carbon atoms (for example, a phenylene group and a fluorenylene group), or a substituted or unsubstituted hetero fused ring group having 9 to 50 ring atoms.

For the members such as a substrate, an anode and a cathode of the organic EL device, in addition to those described above, it is possible to select appropriately and use known materials described in documents such as WO 2009/107596 A1, WO 2009/081857 A1, US 2009/0243473 A1, US 2008/0014464 A1 and US 2009/0021160 A1.

EXAMPLES

Although the present invention will be explained more specifically with the following examples, it shall not be limited thereto.

The structures of intermediates produced in Intermediate Synthesis Examples 1 to 9 are as follows:

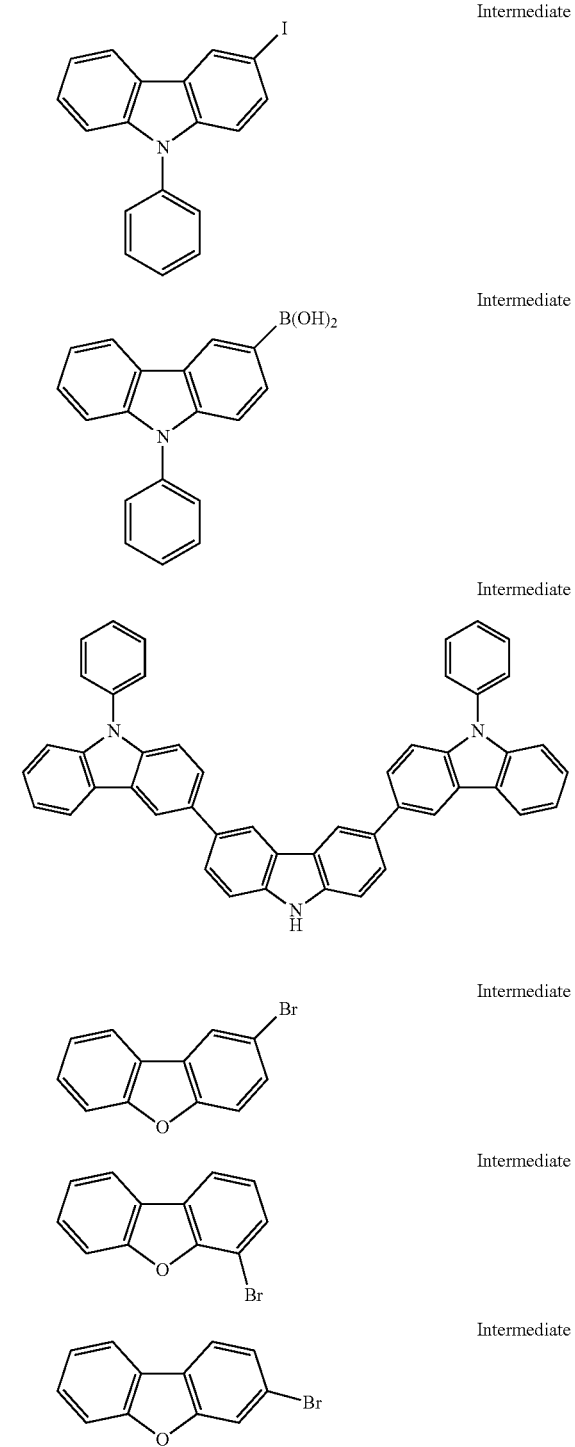

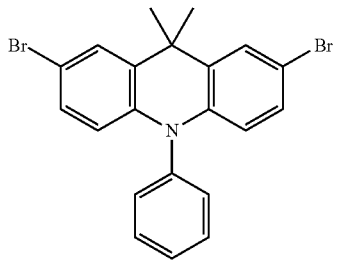

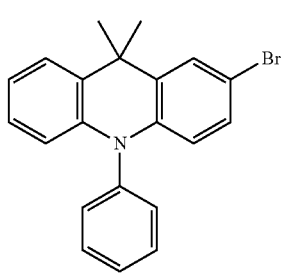

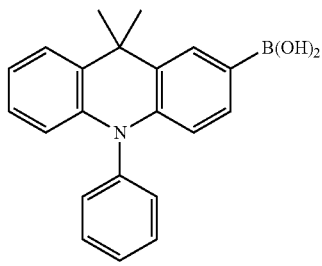

Intermediate Synthesis Example 1

Synthesis of Intermediate 1

17.7 g of 9-phenylcarbazole, 6.03 g of potassium iodide, 7.78 g of potassium iodate, 5.90 mL of sulfuric acid and ethanol were placed and reacted at 75° C. for 2 hours.

After cooling, water and ethyl acetate were added thereto to be separated into a water phase and an organic phase. The organic phase was extracted, washed with sodium bicarbonate water and water, and concentrated to obtain a crude product. The crude product was purified with silica gel chromatography (with toluene), and the resultant solids were dried under reduced pressure to obtain 21.8 g of white solids. The solids were identified as Intermediate 1 by FD-MS analysis.

Intermediate Synthesis Example 2

Synthesis of Intermediate 2

Under a flow of argon, dehydrated toluene and dehydrated ether were added to 13.1 g of Intermediate 1 and the mixture was cooled to −45° C. 25 mL of n-butyllithium hexane solution (1.58 M) was dropped to the mixture, the temperature of which was raised over 1 hour to −5° C. under stirring. The resultant mixture was cooled again to −45° C., and was reacted for 2 hours after 25 mL of boronic acid triisopropyl ester was slowly dropped thereto.

After the mixture was allowed to be at a room temperature, 10% dilute hydrochloric solution was added and stirred therewith, and the resultant organic phase was extracted. After being washed with saturated saline, the organic phase was dried with anhydrous magnesium sulfate and subjected to separation and concentration. The solids obtained were purified with silica gel chromatography (with toluene), and the resultant was washed with n-hexane and dried under reduced pressure to obtain 7.10 g of solids. The solids were identified as Intermediate 2 by FD-MS analysis.

Intermediate Synthesis Example 3

Synthesis of Intermediate 3

Under an argon atmosphere, 100 mL of toluene, 100 mL of 1,2-dimethoxyethane, and 50 mL of 2 M sodium carbonate aqueous solution were added to 32.5 g of 3,6-dibromocarbazole, 63.2 g of Intermediate 2, and 0.92 g of tetrakis(triphenylphosphine)palladium (0), and the mixture was heated under reflux for 10 hours.

After completion of a reaction, the reacted mixture was immediately subjected to filtration and the water phase was then removed. The organic phase was dried with sodium sulfate and concentrated. The residual concentrate was purified with silica gel column chromatography to obtain 45.5 g of white crystals. The crystals were identified as Intermediate 3 by FD-MS analysis.

Intermediate Synthesis Example 4

Synthesis of Intermediate 4

150 g of dibenzofuran (892 millimoles) and 1 liter of acetic acid were placed in a flask, which was then replaced with nitrogen and the contents of which were dissolved under heating. After 188 g of bromine (1.18 moles) were dropped while being occasionally cooled with water, the mixture was stirred for 20 hours under cooling with air. The precipitated crystals were filtrated, washed sequentially with acetic acid and water, and dried under reduced pressure. After the crystals obtained were purified by distillation under reduced pressure, recrystallization from methanol was performed several times to obtain 66.8 g of 2-bromodibenzofuran (yield 31%). The resultant was identified as Intermediate 4 by FD-MS analysis.

Intermediate Synthesis Example 5

Synthesis of Intermediate 5

Under an argon atmosphere, 600 mL of dehydrated tetrahydrofuran was added to 78.0 g of dibenzofuran and the mixture was cooled to −30° C. 300 mL of n-butyllithiumhexane solution (1.65 M) was then dropped and the mixture was heated to a room temperature over 1 hour under stirring. After being stirred for 5 hours at a room temperature, the mixture was cooled to −60° C., and 60 mL of 1,2-dibromoethane was dropped thereto over 1 hour.

After being stirred for 15 hours at a room temperature, the mixture was poured into 1000 mL of ice water, and the organic phase was extracted with dichloromethane. The extracted organic phase was washed with saturated saline, dried with anhydrous magnesium sulfate, and subjected to filtration and concentration. The solids obtained were purified with silica gel chromatography (with toluene), washed with tetrahydrofuran/methanol, and dried under reduced pressure to obtain 70 g of solids. The solids were identified as Intermediate 5 by FD-MS analysis.

Intermediate Synthesis Example 6

Synthesis of Intermediate 6

Under an argon atmosphere, 1000 mL of toluene and 500 mL of 2 M sodium carbonate aqueous solution were added to 120.0 g of 1-buromo-3-fluoro-4-iodobenzene (399 millimoles), 72.7 g of 2-methoxyphenylboronic acid (479 millimoles) and 9.2 g of tetrakis(triphenylphosphine)palladium (0) (7.96 millimoles), and the mixture was heated under reflux for 10 hours.

After completion of a reaction, the reacted mixture was immediately subjected to filtration and the water phase was then removed. The organic phase was dried with sodium sulfate and concentrated. The residual concentrate was purified with silica gel column chromatography to obtain 89.6 g of 4-buromo-2-fluoro-2'-methoxybiphenyl white crystals (yield 80%).

Under an argon atmosphere, 900 mL of dichloromethane was added to 89.6 g of 4-buromo-2-fluoro-2'-methoxybiphenyl (319 millimoles), and the mixture was stirred under cooling with ice. 95.9 g of boron tribromide (382 millimoles) was then dropped and the mixture was stirred at a room temperature for 12 hours. After completion of a reaction, 200 mL of water was added, the mixture was stirred for 1 hour, and the water phase was removed. The organic phase was dried with sodium sulfate and concentrated. The residual concentrate was purified with silica gel column chromatography to obtain 68.1 g of 4-buromo-2-fluoro-2'-hydroxybiphenyl white crystals (yield 70%).

1500 mL of N-methylpyrrolidone was added to 68.1 g of 4-buromo-2-fluoro-2'-hydroxybiphenyl (255 millimoles) and 70.4 g of potassium carbonate (510 millimoles), and the mixture was stirred for 3 hours at 180° C. After completion of a reaction, water was added and the mixture was subjected to extraction with toluene. The organic phase was dried with sodium sulfate and concentrated. The residual concentrate was purified by recrystallization from toluene to obtain 44.2 g of 3-buromodibenzofuran white crystals (yield 60%). The crystals were identified as Intermediate 6 by FD-MS analysis.

Intermediate Synthesis Example 7

Synthesis of Intermediate 7

Under an argon atmosphere, 350 mL of dimethylformamide (DMF) was added to 28.5 g of 9,9-dimethyl-10-phenyl-9,10-dihydroacridine (100 millimoles) and 35.6 g of N-buromosuccinimide (NBS) (200 millimoles), and the mixture was stirred at a room temperature for 8 hours. After completion of a reaction, the reacted mixture was transferred to a separatory funnel, water (500 mL) was added thereto, and the mixture was subjected to extraction with ethyl acetate. The extract was purified with column chromatography to obtain 35.4 g of white solids. The solids were identified as Intermediate 7 by FD-MS analysis.

Intermediate Synthesis Example 8

Synthesis of Intermediate 8

Under an argon atmosphere, 350 mL of DMF was added to 28.5 g of 9,9-dimethyl-10-phenyl-9,10-dihydroacridine (100 millimoles) and 17.8 g of NBS (100 millimoles), and the mixture was stirred at a room temperature for 8 hours. After completion of a reaction, the reacted mixture was transferred to a separatory funnel, water (500 mL) was added thereto, and the mixture was subjected to extraction with ethyl acetate. The extract was purified with column chromatography to obtain 18.4 g of white solids. The solids were identified as Intermediate 8 by FD-MS analysis.

Intermediate Synthesis Example 9

Synthesis of Intermediate 9

Reaction was conducted in a similar way to Intermediate Synthesis Example 2 except that 12.9 g of Intermediate 8 was used instead of Intermediate 1 to obtain 8.2 g of white solids. The solids were identified as Intermediate 9 by FD-MS analysis.

The structures of the nitrogen-containing aromatic heterocyclic derivatives according to the present invention prepared in Intermediate Synthesis Examples 1 to 7 are as follows:

H1

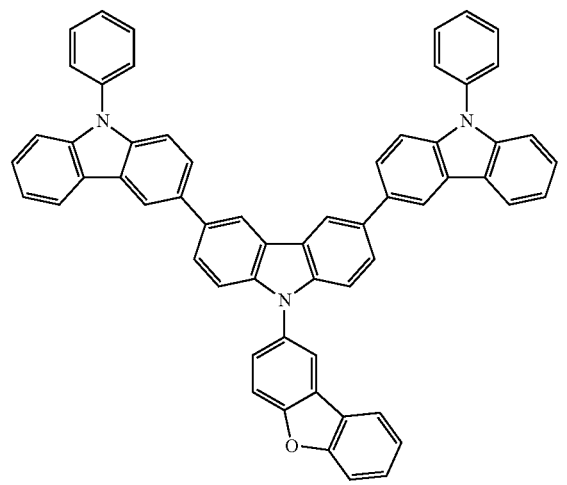

H2

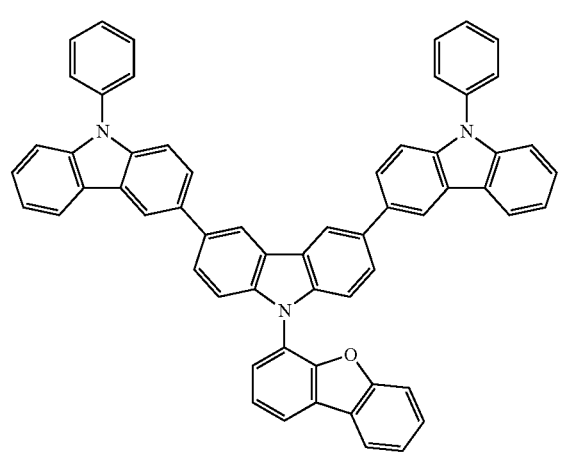

H3

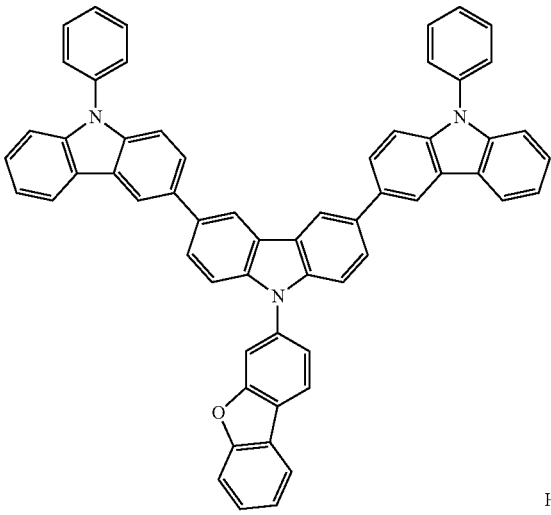

H4

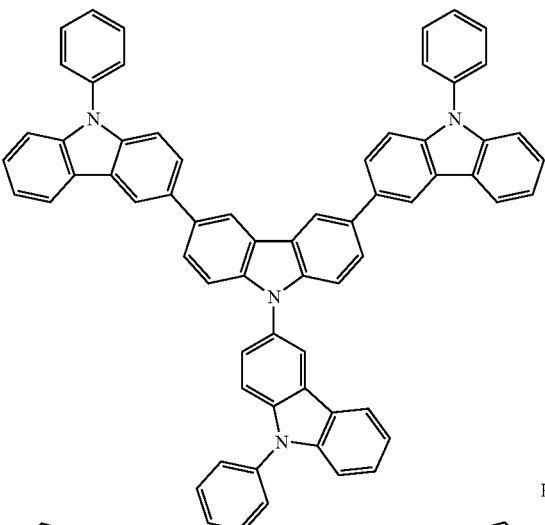

H5

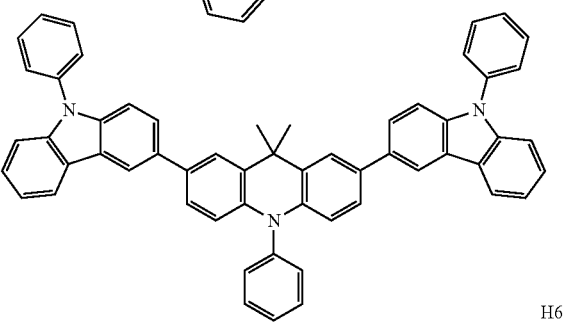

H6

-continued

H7

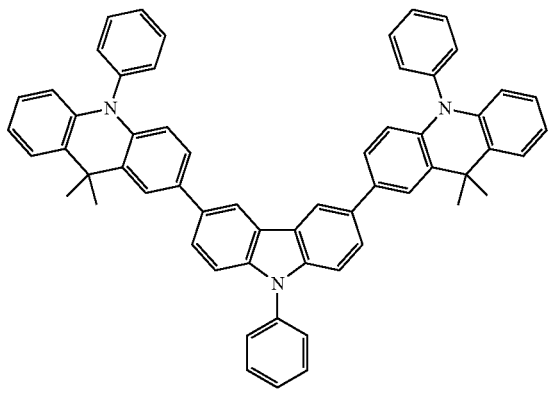

Synthesis Example 1

Preparation of Nitrogen-Containing Aromatic Heterocyclic Derivative (H1)

Under a flow of argon, 6.5 g of Intermediate 3, 2.5 g of Intermediate 4, 1.3 g of sodium t-butoxide (manufactured by Hiroshima Wako Ltd.), 46 mg of tris(dibenzylideneacetone) dipalladium (manufactured by Aldrich Corp.), 29 mg of tri-tert-butylphosphoniumtetrafluoroborate, and 50 mL of dehydrated toluene were mixed and reacted for 8 hours at 80° C.

After cooling, 500 mL of water was added and the mixture was filtrated with cellite. The filtrate was extracted with toluene and the extract was dried with anhydrous magnesium sulfate. The dried extract was concentrated under reduced pressure, and the crude product obtained was purified with column chromatography and recrystallized from toluene. The recrystallized product was filtrated and dried to obtain 5.6 g of white powder. The white powder was identified as Nitrogen-containing aromatic heterocyclic derivative (H1) by FD-MS analysis.

Synthesis Example 2

Preparation of Nitrogen-Containing Aromatic Heterocyclic Derivative (H2)

Reaction was conducted in a similar way to Synthesis Example 1 except that 2.5 g of Intermediate 5 was used instead of Intermediate 4 to obtain 5.3 g of white powder. The white powder was identified as Nitrogen-containing aromatic heterocyclic derivative (H2) by FD-MS analysis.

Synthesis Example 3

Preparation of Nitrogen-Containing Aromatic Heterocyclic Derivative (H3)

Reaction was conducted in a similar way to Synthesis Example 1 except that 2.5 g of Intermediate 6 was used instead of Intermediate 4 to obtain 5.7 g of white powder. The white powder was identified as Nitrogen-containing aromatic heterocyclic derivative (H3) by FD-MS analysis.

Synthesis Example 4

Preparation of Nitrogen-Containing Aromatic Heterocyclic Derivative (H4)

Reaction was conducted in a similar way to Synthesis Example 1 except that 3.7 g of Intermediate 1 was used instead of Intermediate 4 to obtain 6.3 g of white powder. The white powder was identified as Nitrogen-containing aromatic heterocyclic derivative (H4) by FD-MS analysis.

Synthesis Example 5

Preparation of Nitrogen-Containing Aromatic Heterocyclic Derivative (H5)

Under an argon atmosphere, 10 mL of toluene and 10 mL of 1,2-dimethoxyethane, and 5 mL of 2M sodium carbonate aqueous solution were added to 4.4 g of Intermediate 7, 6.3 g of Intermediate 2, and 92 mg of tetrakis(triphenylphosphine) palladium (0), and the mixture was heated under reflux for 10 hours.

After completion of a reaction, the reacted mixture was immediately subjected to filtration and the water phase was then removed. The organic phase was dried with sodium sulfate and concentrated. The residual concentrate was purified with silica gel column chromatography to obtain 5.4 g of white powder. The white powder was identified as Nitrogen-containing aromatic heterocyclic derivative (H5) by FD-MS analysis.

Synthesis Example 6

Preparation of Nitrogen-Containing Aromatic Heterocyclic Derivative (H6)

Reaction was conducted in a similar way to Synthesis Example 5 except that 7.2 g of Intermediate 9 was used instead of Intermediate 2 to obtain 6.0 g of white powder. The white powder was identified as Nitrogen-containing aromatic heterocyclic derivative (H6) by FD-MS analysis.

Synthesis Example 7

Preparation of Nitrogen-Containing Aromatic Heterocyclic Derivative (H7)

Reaction was conducted in a similar way to Synthesis Example 5 except that 4.0 g of 3,6-dibromo-9-phenylcarbazole was used instead of Intermediate 7 and 7.2 g of Intermediate 9 was used instead of Intermediate 2 to obtain 5.4 g of white powder. The white powder was identified as Nitrogen-containing aromatic heterocyclic derivative (H7) by FD-MS analysis.

Example 1-1

Production of Organic EL Device

A glass substrate of 25 mm by 75 mm by 1.1 mm with an ITO transparent electrode (manufactured by GEOMATEC CO., LTD.) was subjected to ultrasonic cleaning in isopropyl alcohol for 5 minutes, and cleaning with ultraviolet rays and ozone for 30 minutes.

The resultant glass substrate with transparent electrode lines was mounted on a substrate holder in a vacuum deposition device. First, the following electron-acceptor compound (A) was deposited to form a 5 nm-thick A film so as to cover the surface of the transparent electrode on which the transparent electrode lines were formed. The following aromatic amine derivative (X1) was deposited as a first hole-transporting material on the A film to form a 120 nm-thick first hole-transporting layer. Then, the nitrogen-containing aromatic heterocyclic derivative (H1) obtained in Synthesis Example 1 was deposited as a second hole-transporting material to form a 47 nm-thick second hole-transporting layer. Onto the second hole-transporting layer, a compound (B) as a phosphorescent host and Ir(ppy)₃ as a phosphorescent dopant were co-deposited to obtain a 40 nm-thick phosphorescent layer. The concentration of Ir(ppy)₃ was 10 mass %.

Subsequently, a 20 nm-thick compound (C) layer was formed on the phosphorescent layer as an electron-transporting layer, and a 1 nm-thick LiF layer and a 80 nm-thick Al metal layer were sequentially formed to obtain a cathode. The LiF layer, which was an electron-injecting electrode, was formed at a speed of 1 Å/min.

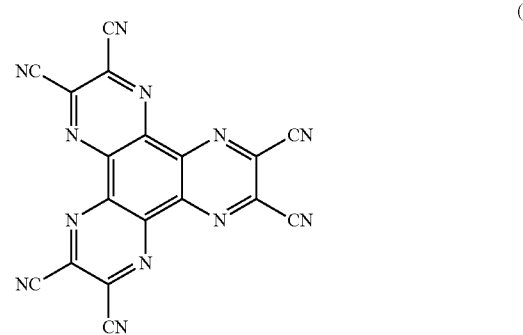

(A)

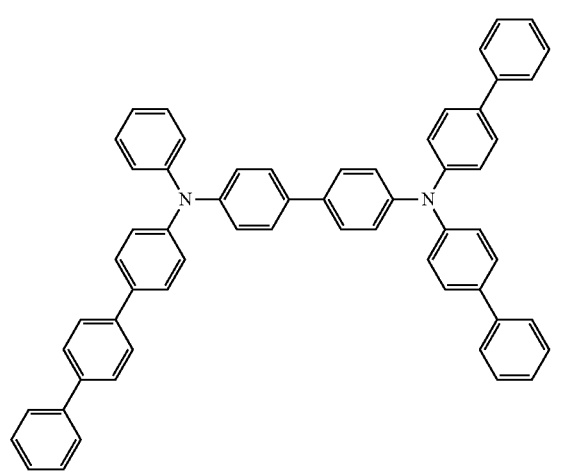

(B)

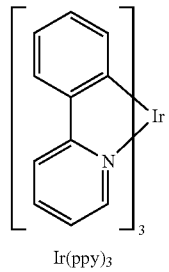

Ir(ppy)₃

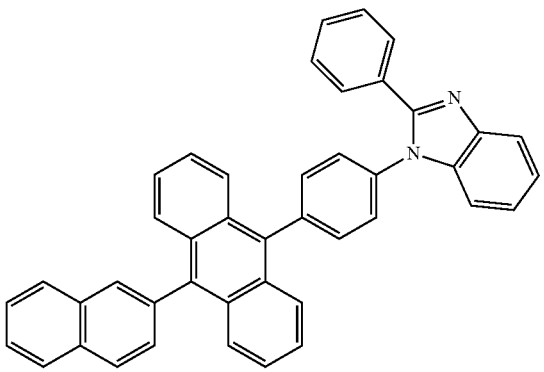

(C)

(Evaluation of Luminescent Performance of Organic EL Device)

The organic EL device obtained was made to emit light with DC driving, and was measured for luminance (L) and a current density to determine luminous efficiency (L/J) and driving voltage (V) at a current density of 1 mA/cm².

In addition, half life at an initial luminance of 20000 cd/m² was determined. The results were shown in Table 1.

Example 1-2

Production and Evaluation of Luminescent Performance of Organic EL Device

Except that Nitrogen-containing aromatic heterocyclic derivative (H2) was used instead of Nitrogen-containing aromatic heterocyclic derivative (H1) as the second hole-transporting material, an organic EL device was produced and evaluation was performed in the same manner as in Example 1-1. The results were shown in Table 1.

Comparative Examples 1-1 to 1-3

Production and Evaluation of Luminescent Performance of Organic EL Device

Except that the following Comparative Compounds 1 to 3 were used instead of Nitrogen-containing aromatic heterocyclic derivative (H1) as the second hole-transporting material, an organic EL device was produced and evaluation was performed in the same manner as in Example 1-1. The results were shown in Table 1.

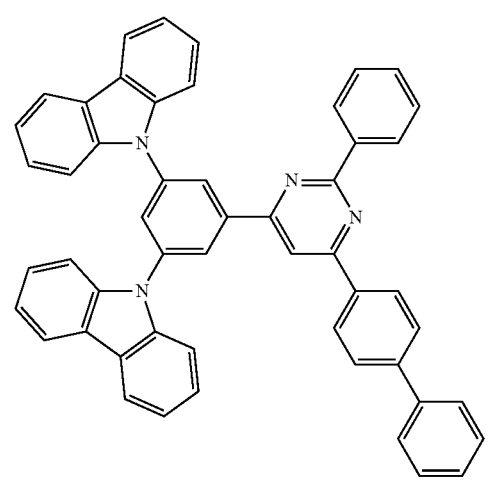

TABLE 1

| | | Hole-transporting material | Luminous efficiency [cd/A] @ 1 mA/cm² | Driving voltage [V] @ 1 mA/cm² | Half life [hour] |
|---|---|---|---|---|---|
| Examples | 1-1 | H1 | 58.7 | 3.4 | 700 |
| | 1-2 | H2 | 58.1 | 3.4 | 720 |
| Comparative Examples | 1-1 | Comparative compound 1 | 58.0 | 3.7 | 500 |
| | 1-2 | Comparative compound 2 | 57.5 | 4.0 | 450 |
| | 1-3 | Comparative compound 3 | 53.5 | 3.4 | 150 |

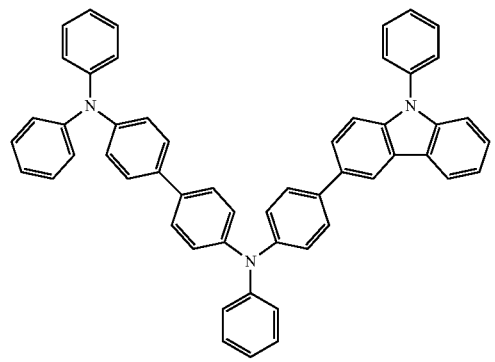

Comparative Compound 1

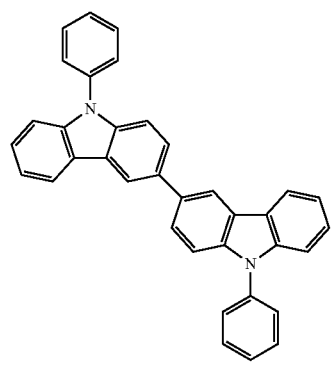

Comparative Compound 2

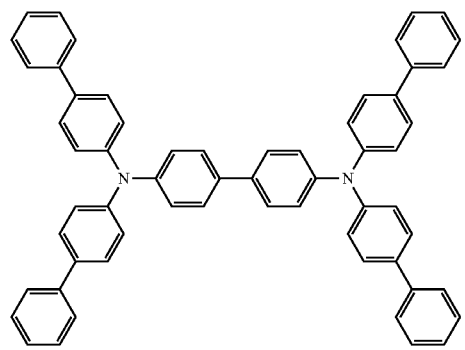

Comparative Compound 3

As shown in Table 1, the organic EL devices using the nitrogen-containing aromatic heterocyclic derivative according to the invention as the hole-transporting material could have a higher luminous efficiency, a lower driving voltage and a longer device life compared with the organic EL devices using the comparative compounds.

Example 2-1

Production of Organic EL Device

A glass substrate of 25 mm by 75 mm by 1.1 mm with an ITO transparent electrode (GEOMATEC CO., LTD.) was subjected to ultrasonic cleaning in isopropyl alcohol for 5 minutes, and cleaning with ultraviolet rays and ozone for 30 minutes.

The resultant substrate with transparent electrode lines was mounted on a substrate holder in a vacuum deposition device. First, the above aromatic amine derivative (X1) was deposited as a hole-injecting material to form a 90 nm-thick hole-injecting layer so as to cover the surface of the transparent electrode on which the transparent electrode lines were formed. Subsequent to the forming of the hole-injecting layer, the following aromatic amine derivative (X2) was deposited as a hole-transporting material to form a 20 nm-thick hole-transporting layer.

Nitrogen-containing aromatic heterocyclic derivative (H1) as a host for phosphorescence and FIrpic as a dopant for phosphorescence were co-deposited on the hole-transporting layer to form a 40 nm-thick phosphorescent layer. The concentration of FIrpic was 10 mass %.

Next, on the phosphorescent layer, a 10 nm-thick BCP layer was formed as a hole-blocking layer. Furthermore, a 20 nm-thick compound (C) layer was formed as an electron-transporting layer, and a 1 nm-thick LiF layer and a 80 nm-thick Al metal layer were sequentially formed to obtain a cathode. The LiF layer, which was an electron-injecting electrode, was formed at a speed of 1 Å/min.

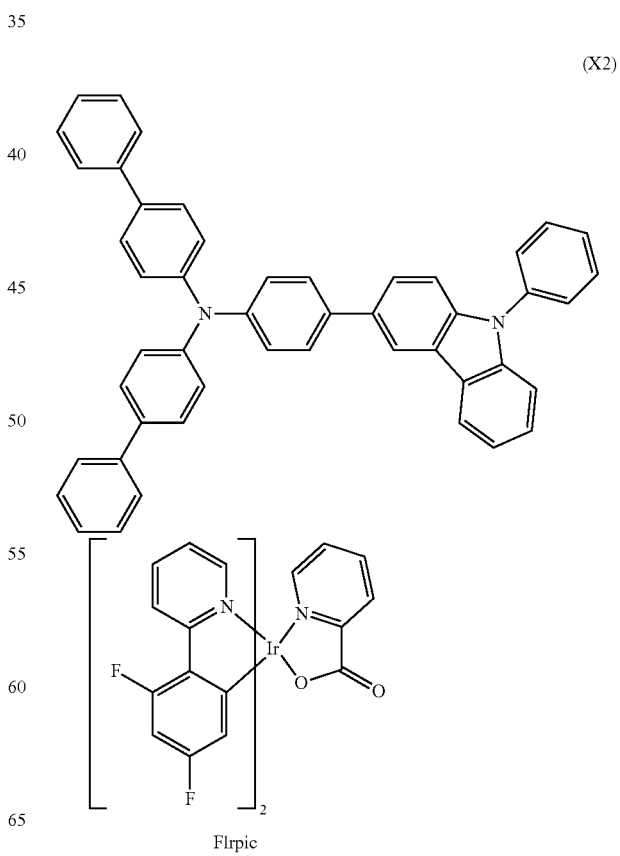

-continued

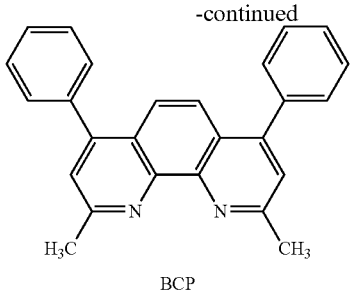

BCP (Evaluation of Luminescent Performance of Organic EL Device)

The organic EL device obtained was made to emit light with DC driving, and was measured for luminance (L) and a current density to determine luminous efficiency (L/J) at a current density of 1 mA/cm² and driving voltage (V).

In addition, half life at an initial luminance of 1000 cd/m² was determined. The results were shown in Table 2.

Example 2-2

Production of Organic EL Device

Except that Nitrogen-containing aromatic heterocyclic derivative (H2) was used instead of Nitrogen-containing aromatic heterocyclic derivative (H1) as a phosphorescent host material, an organic EL device was produced and evaluation was performed in the same manner as in Example 2-1. The results were shown in Table 2.

Comparative Examples 2-1 and 2-2

Production of Organic EL device and Evaluation of Luminescent Performance

Except that the above Comparative Compounds 1 and 2 were used instead of Nitrogen-containing aromatic heterocyclic derivative (H1) as a phosphorescent host material, an organic EL device was produced and evaluation was performed in the same manner as in Example 2-1. The results were shown in Table 2.

TABLE 2

| | | Phosphorescent host material | Luminous efficiency [cd/A] @1 mA/cm² | Driving voltage [V] @1 mA/cm² | Half life [hour] |
|---|---|---|---|---|---|
| Examples | 2-1 | H1 | 17.9 | 4.7 | 50 |
| | 2-2 | H2 | 17.5 | 4.7 | 50 |
| Comparative Examples | 2-1 | Comparative compound 1 | 3.4 | 5.0 | 3 |
| | 2-2 | Comparative compound 2 | 3.5 | 5.3 | 3 |

As shown in Table 2, the organic EL devices using in the phosphorescent emitting layer the nitrogen-containing aromatic heterocyclic derivatives according to the invention could have a higher luminous efficiency, a lower driving voltage and longer life compared with the organic EL devices using the comparative compounds.

INDUSTRIAL APPLICABILITY

The compound of the present invention can be used for an organic EL device. The organic EL device of the invention can be used as a planar emitting body such as a flat panel display of a wall-hanging television, backlight of a copier, a printer or a liquid crystal display, light sources for instruments, a display panel, a navigation light, and the like.

Although only some exemplary embodiments and/or examples of this invention have been described in detail above, those skilled in the art will readily appreciated that many modifications are possible in the exemplary embodiments and/or examples without materially departing from the novel teachings and advantages of this invention. Accordingly, all such modifications are intended to be included within the scope of this invention.

The contents of the above-described documents are herein incorporated by reference in its entirety.

The invention claimed is:

1. A nitrogen-comprising aromatic heterocyclic compound of formula (1):

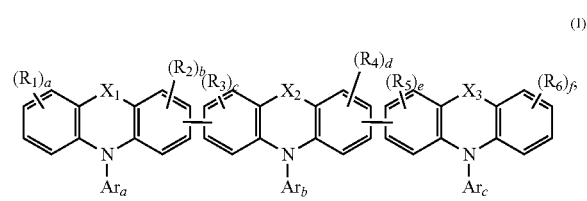

wherein
$X_1$ to $X_3$ are each independently a single bond, CRaRb, NRc, an oxygen atom, or a sulfur atom,
Ra, Rb, and Rc are each independently a linear or branched alkyl group comprising 1 to 15 carbon atoms, a cycloalkyl group comprising 3 to 15 carbon atoms, an aryl group comprising 6 to 20 ring carbon atoms, or a heteroaryl group comprising 5 to 20 ring atoms,
$Ar_a$, and $Ar_c$ are each independently a substituted or unsubstituted aryl group comprising 6 to 20 ring carbon atoms or a substituted or unsubstituted heteroaryl group comprising 5 to 20 ring atoms,
$Ar_b$ is a group having the following formula of (5-3),
when all of $X_1$ to $X_3$ are a single bond, at least one selected from the group consisting of $Ar_a$, $Ar_b$, and $Ar_c$ is an aryl group comprising 6 to 20 ring carbon atoms substituted with a heteroaryl group, an aryloxy group, or a heteroaryloxy group, or a substituted or unsubstituted heteroaryl group comprising 5 to 20 ring atoms,
$R_1$ to $R_6$ are each independently a linear or branched alkyl group comprising 1 to 15 carbon atoms, a cycloalkyl group comprising 3 to 15 carbon atoms, a substituted or unsubstituted silyl group, an aryl group comprising 6 to 20 ring carbon atoms, a heteroaryl group comprising 5 to 20 ring atoms, a halogen atom, or a cyano group, wherein two adjacent groups from $R_1$ to $R_6$ may be saturated or unsaturated divalent groups that are bonded to each other to form a ring,
a and f are each independently an integer of 0 to 4, and
b, c, d, and e are each independently an integer of 0 to 3,

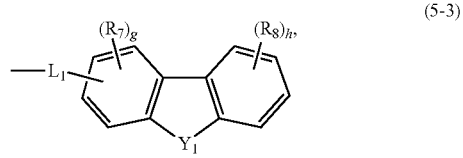

(5-3)

wherein
- $R_7$ and $R_8$ are each independently a linear or branched alkyl group comprising 1 to 15 carbon atoms, a cycloalkyl group comprising 3 to 15 carbon atoms, a substituted or unsubstituted silyl group, an aryl group comprising 6 to 20 ring carbon atoms, a heteroaryl group comprising 5 to 20 ring atoms, a halogen atom, or a cyano group,
- $R_7$ and $R_8$ may be saturated or unsaturated divalent groups that are bonded each to other to form a ring,
- $Y_1$ is an oxygen atom,
- $L_1$ is a single bond,
- h is an integer of 0 to 4, g is an integer of 0 to 3, and i is an integer of 0 to 6.

2. The compound of claim 1, having formula (2):

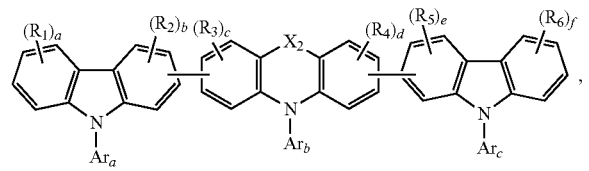

(2)

wherein
- $X_2$ is a single bond, CRaRb, NRc, an oxygen atom, or a sulfur atom,
- Ra, Rb, and Rc are each independently a linear or branched alkyl group comprising 1 to 15 carbon atoms, a cycloalkyl group comprising 3 to 15 carbon atoms, an aryl group comprising 6 to 20 ring carbon atoms, or a heteroaryl group comprising 5 to 20 ring atoms,
- $Ar_a$, and $Ar_c$ are each independently a substituted or unsubstituted aryl group comprising 6 to 20 ring carbon atoms or a substituted or unsubstituted heteroaryl group comprising 5 to 20 ring atoms,
- $Ar_b$ is a group having the following formula of (5-3),
- wherein when $X_2$ is a single bond, at least one selected from the group consisting of $Ar_a$, $Ar_b$, and $Ar_c$ is an aryl group comprising 6 to 20 ring carbon atoms substituted with a heteroaryl group, an aryloxy group, or a heteroaryloxy group, or a substituted or unsubstituted heteroaryl group comprising 5 to 20 ring atoms,
- $R_1$ to $R_6$ are each independently a linear or branched alkyl group comprising 1 to 15 carbon atoms, a cycloalkyl group comprising 3 to 15 carbon atoms, a substituted or unsubstituted silyl group, an aryl group comprising 6 to 20 ring carbon atoms, a heteroaryl group comprising 5 to 20 ring atoms, a halogen atom, or a cyano group, wherein two adjacent groups from $R_1$ to $R_6$ may be saturated or unsaturated divalent groups that are bonded each to other to form a ring,
- a and f are each independently an integer of 0 to 4, and b, c, d, and e are each independently an integer of 0 to 3,

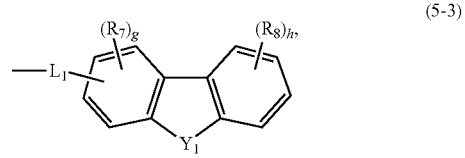

(5-3)

wherein
- $R_7$ and $R_8$ are each independently a linear or branched alkyl group comprising 1 to 15 carbon atoms, a cycloalkyl group comprising 3 to 15 carbon atoms, a substituted or unsubstituted silyl group, an aryl group comprising 6 to 20 ring carbon atoms, a heteroaryl group comprising 5 to 20 ring atoms, a halogen atom, or a cyano group,
- $R_7$ and $R_8$ may be saturated or unsaturated divalent groups that are bonded each to other to form a ring,
- $Y_1$ is an oxygen atom, or a sulfur atom,
- $L_1$ is a single bond,
- h is an integer of 0 to 4, g is an integer of 0 to 3, and i is an integer of 0 to 6.

3. The compound of claim 1, having formula (3):

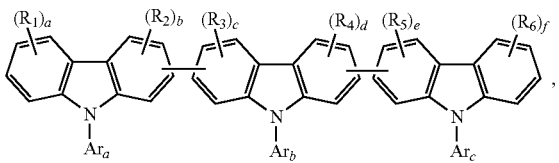

(3)

wherein
- $Ar_a$, and $Ar_c$ are each independently a substituted or unsubstituted aryl group comprising 6 to 20 ring carbon atoms or a substituted or unsubstituted heteroaryl group comprising 5 to 20 ring atoms,
- $Ar_b$ is a group having the following formula of (5-3),
- $R_1$ to $R_6$ are each independently a linear or branched alkyl group comprising 1 to 15 carbon atoms, a cycloalkyl group comprising 3 to 15 carbon atoms, a substituted or unsubstituted silyl group, an aryl group comprising 6 to 20 ring carbon atoms, a heteroaryl group comprising 5 to 20 ring atoms, a halogen atom, or a cyano group, wherein two adjacent groups from $R_1$ to $R_6$ may be saturated or unsaturated divalent groups that are bonded to each other to form a ring,
- a and f are each independently an integer of 0 to 4, and b, c, d, and e are each independently an integer of 0 to 3,

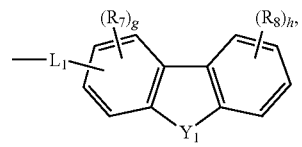

(5-3)

wherein
- $R_7$ and $R_8$ are each independently a linear or branched alkyl group comprising 1 to 15 carbon atoms, a cycloalkyl group comprising 3 to 15 carbon atoms, a substituted or unsubstituted silyl group, an aryl group comprising 6 to 20 ring carbon atoms, a heteroaryl group comprising 5 to 20 ring atoms, a halogen atom, or a cyano group, $R_7$ and $R_8$ may be saturated or unsaturated divalent groups that are bonded each to other to form a ring, $Y_1$ is an oxygen atom, $L_1$ is a single bond, h is an integer of 0 to 4, g is an integer of 0 to 3, and i is an integer of 0 to 6.

4. The compound of claim 1, having formula (4):

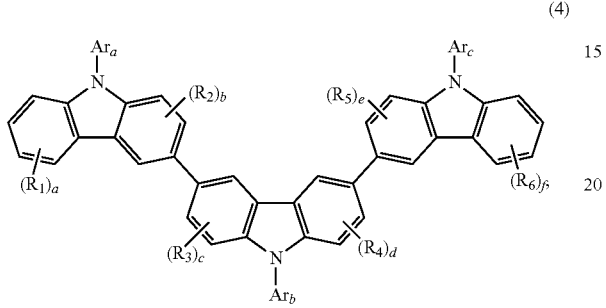

(4)

wherein $Ar_a$, and $Ar_c$ are each independently a substituted or unsubstituted aryl group comprising 6 to 20 ring carbon atoms or a substituted or unsubstituted heteroaryl group comprising 5 to 20 ring atoms, $Ar_b$ is a group having the following formula of (5-3), $R_1$ to $R_6$ are each independently a linear or branched alkyl group comprising 1 to 15 carbon atoms, a cycloalkyl group comprising 3 to 15 carbon atoms, a substituted or unsubstituted silyl group, an aryl group comprising 6 to 20 ring carbon atoms, a heteroaryl group comprising 5 to 20 ring atoms, a halogen atom, or a cyano group, wherein two adjacent groups from $R_1$ to $R_6$ may be saturated or unsaturated divalent groups that are bonded to each other to form a ring, a and f are each independently an integer of 0 to 4, and b, c, d, and e are each independently an integer of 0 to 3,

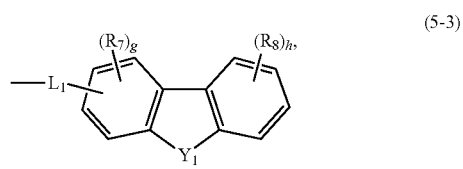

(5-3)

wherein $R_7$ and $R_8$ are each independently a linear or branched alkyl group comprising 1 to 15 carbon atoms, a cycloalkyl group comprising 3 to 15 carbon atoms, a substituted or unsubstituted silyl group, an aryl group comprising 6 to 20 ring carbon atoms, a heteroaryl group comprising 5 to 20 ring atoms, a halogen atom, or a cyano group, $R_7$ and $R_8$ may be saturated or unsaturated divalent groups that are bonded each to other to form a ring, $Y_1$ is an oxygen atom, $L_1$ is a single bond, h is an integer of 0 to 4, g is an integer of 0 to 3, and i is an integer of 0 to 6.

5. The compound of claim 1, wherein $Ar_a$, and $Ar_c$ are each independently a phenyl group or a group having a formula of (5-1) to (5-3):

(5-1)

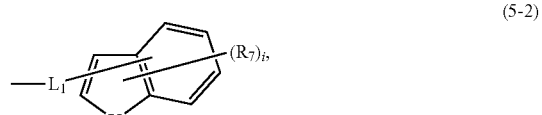

(5-2)

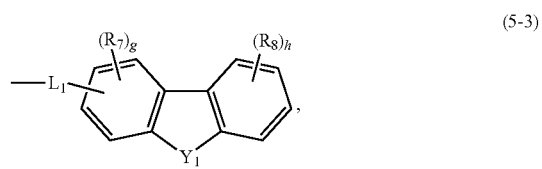

(5-3)

wherein $R_7$ and $R_8$ are each independently a linear or branched alkyl group comprising 1 to 15 carbon atoms, a cycloalkyl group comprising 3 to 15 carbon atoms, a substituted or unsubstituted silyl group, an aryl group comprising 6 to 20 ring carbon atoms, a heteroaryl group comprising 5 to 20 ring atoms, a halogen atom, or a cyano group, $R_7$ and $R_8$ may be saturated or unsaturated divalent groups that are bonded each to other to form a ring, $Y_1$ is an oxygen atom, $L_1$ is a single bond, a substituted or unsubstituted arylene group comprising 6 to 20 ring carbon atoms, or a substituted or unsubstituted heteroarylene group comprising 5 to 20 ring atoms, h is an integer of 0 to 4, g is an integer of 0 to 3, and i is an integer of 0 to 6.

6. The compound of claim 1, which is a material for an organic electroluminescence device.

7. The compound of claim 1, which is a hole-transporting material for an organic electroluminescence device.

8. An organic electroluminescence device, comprising:

a cathode;

an anode; and an organic thin film layer between the cathode and the anode, wherein the organic thin film layer comprises the compound of claim 1.

9. The device of claim 8, wherein the organic thin film layer comprises at least one hole layer selected from the group consisting of a hole-transporting layer and a hole-injecting layer, and at least one hole layer comprises the compound of formula (1).

10. The device of claim 9, wherein the at least one hole layer is in contact with a layer comprising a compound of formula (10):

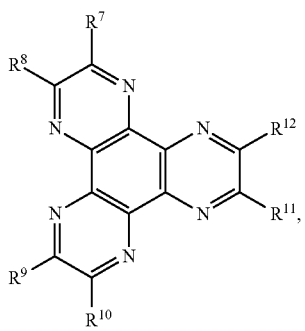

(10)

wherein
$R^7$ to $R^{12}$ are each independently a cyano group, —$CONH_2$, a carboxy group, or —$COOR^{13}$, wherein $R^{13}$ is an alkyl group comprising 1 to 20 carbon atoms, or $R^7$ and $R^8$, $R^9$ and $R^{10}$, or $R^{11}$ and $R^{12}$ are bonded to each other to form —CO—O—CO—.

11. The device of claim 8, wherein the organic thin film layer comprises an emitting layer comprising a phosphorescent emitting material.

12. The device of claim 8, wherein the organic thin film layer comprises an emitting layer comprising a phosphorescent emitting material and the compound of formula (1), as a host material.

13. The device of claim 11, wherein the phosphorescent emitting material is an ortho-metalated complex of iridium (Ir), osmium (Os), or platinum (Pt) metal.

14. The device of claim 8, wherein the organic thin film layer comprises an electron transporting layer comprising a nitrogen-comprising aromatic heterocyclic compound having a formula of (60) to (62):

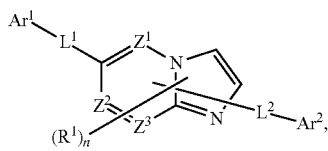

(60)

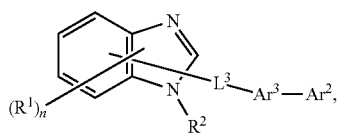

(61)

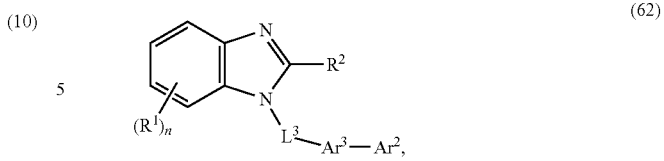

(62)

wherein
$Z^1$, $Z^2$, and $Z^3$ are each independently a nitrogen atom or a carbon atom, $R^1$ and $R^2$ are each independently a substituted or unsubstituted aryl group comprising 6 to 50 ring carbon atoms, a substituted or unsubstituted heteroaryl group comprising 3 to 50 ring atoms, an alkyl group comprising 1 to 20 carbon atoms, an alkyl group comprising 1 to 20 carbon atoms substituted with a halogen atom, or an alkoxy group comprising 1 to 20 carbon atoms, n is an integer of 0 to 4, wherein when n is an integer of 2 or more, each $R^1$ may be the same or different, or two adjacent $R^1$ groups may be bonded to each other to form a substituted or unsubstituted aromatic hydrocarbon ring, $Ar^1$ is a substituted or unsubstituted aryl group comprising 6 to 50 ring carbon atoms, or a substituted or unsubstituted heteroaryl group comprising 3 to 50 ring atoms, $Ar^2$ is a hydrogen atom, an alkyl group comprising 1 to 20 carbon atoms, an alkyl group comprising 1 to 20 carbon atoms substituted with a halogen atom, an alkoxy group comprising 1 to 20 carbon atoms, a substituted or unsubstituted aryl group comprising 6 to 50 ring carbon atoms, or a substituted or unsubstituted heteroaryl group comprising 3 to 50 ring atoms, wherein, in formula (60), one of $Ar^1$ and $Ar^2$ is a substituted or unsubstituted fused aromatic hydrocarbon ring group comprising 10 to 50 ring carbon atoms or a substituted or unsubstituted fused aromatic heterocyclic group comprising 9 to 50 ring atoms, $Ar^3$ is a substituted or unsubstituted arylene group comprising 6 to 50 ring carbon atoms or a substituted or unsubstituted heteroarylene group comprising 3 to 50 ring atoms, and $L^1$, $L^2$, and $L^3$ are each independently a single bond, a substituted or unsubstituted arylene group comprising 6 to 50 ring carbon atoms or a substituted or unsubstituted hetero fused ring group comprising 9 to 50 ring atoms.

15. The device of claim 13, wherein the phosphorescent emitting material is ortho-metalated iridium complex.

16. The device of claim 12, wherein the phosphorescent emitting material is an ortho-metalated complex of iridium (Ir), osmium (Os), or platinum (Pt) metal.

17. The device of claim 16, wherein the phosphorescent emitting material is ortho-metalated iridium complex.

* * * * *